US006613747B2

(12) United States Patent
Henninger et al.

(10) Patent No.: US 6,613,747 B2
(45) Date of Patent: *Sep. 2, 2003

(54) 6-O-CARBAMOYL KETOLIDE ANTIBACTERIALS

(75) Inventors: Todd C. Henninger, Neshanic Station, NJ (US); Xiaodong Xu, Bridgewater, NJ (US)

(73) Assignee: Ortho-McNeil Pharmaceutical, Inc., Raitan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/011,937

(22) Filed: Dec. 5, 2001

(65) Prior Publication Data

US 2002/0115620 A1 Aug. 22, 2002

Related U.S. Application Data

(63) Continuation-in-part of application No. 09/773,788, filed on Feb. 1, 2001, now Pat. No. 6,472,372.
(60) Provisional application No. 60/251,547, filed on Dec. 6, 2000.

(51) Int. Cl.[7] .................. A61K 31/70; C07M 17/08; C07M 1/00

(52) U.S. Cl. .................. 514/29; 536/7.1; 536/18.5

(58) Field of Search .................. 536/7.4, 18.5; 514/29

(56) References Cited

U.S. PATENT DOCUMENTS

| | | | |
|---|---|---|---|
| 4,826,820 A | 5/1989 | Brain | |
| 5,444,051 A | 8/1995 | Agouridas et al. | |
| 5,559,256 A | 9/1996 | Gordon et al. | |
| 5,561,118 A | 10/1996 | Agouridas et al. | |
| 5,770,579 A | 6/1998 | Agouridas et al. | |
| 5,866,549 A | 2/1999 | Or et al. | |
| 6,472,372 B1 * | 10/2002 | Henninger et al. | 514/29 |

FOREIGN PATENT DOCUMENTS

| | | |
|---|---|---|
| EP | 0 216 169 A2 | 4/1987 |
| EP | 0945459 A | 9/1999 |
| EP | 1 146 051 A2 | 10/2001 |
| WO | WO 97/17356 A1 | 5/1997 |
| WO | WO 97/24124 A1 | 7/1997 |
| WO | WO 98/09978 A1 | 3/1998 |
| WO | WO 98/25942 A1 | 6/1998 |
| WO | WO 98/28264 A1 | 7/1998 |
| WO | WO 99/21864 A1 | 5/1999 |
| WO | WO 99/21871 A1 | 5/1999 |
| WO | WO 99/35157 A1 | 7/1999 |
| WO | WO 00/62783 A2 | 10/2000 |
| WO | WO 00/63224 A2 | 10/2000 |
| WO | WO 00/63225 A2 | 10/2000 |
| WO | WO 00/75156 A1 | 12/2000 |
| WO | WO 01/40241 A2 | 6/2001 |

OTHER PUBLICATIONS

Cannon, J.G. et al., "Ring–Opening Reactions of Certain 2–Carbonyl–Substituted Cyclopropylamines", J. Org. Chem. vol. 40, No., 2, 1975, 182–184.

Daubresse, N. et al., "Phase Transfer Wittig Reaction with 1.3–Dioxolan–2–yl–methyltriphenyl phosphonium Salts: an Efficient Method for Vinylogation of Aromatic Aldehydes", Tetrahedron 54 (1998) 10761–10770.

Glase, S.A. et al., "Aryl 1–But–3–ynyl–4–phenyl–1,2,3, 6–tetrahydropyridines as Potential Antipsychotic Agents: Synthesis and Structure–Activity Relationships", J. Med. Chem. 1996, 39, 3179–3187.

Grisegraber, G. et al., "Anhydrolide Macrolides. 2. Synthesis and Antibacterial Activity of 2,3–Anhydro–6–O–methyll 11, 12–Carbazate Erythromycin A Analogues", J. Med. Chem. 1998, 41, No. 10, 1660–1670.

Haukse, J. R. et al., "Synthesis of 10,11–Anhydroerythromycin", J. Org. Chem. 1982, 47, 1595–1596.

Kim, M.S. et al., "Photophysical Properties and Conformational Equilibrium of trans–6–Styrylquinoxaline", Photochemistry and Photobiology, vol. 54, No. 1, pp. 7–15, 1991.

Kingsbury, W.D. et al., "Synthesis of Structural Analogs of Leukotriene $B_4$ and Their Receptor Binding Activity", J. Med. Chem, 1993, 36, 3308–3320.

Mitzutani, T. et al., "Molecular Recognition of Carbohydrates by Zinc Porphyrins: Lewis Acid/Lewis Base Combinations as a Dominant Factor for Their Selectivity", J. Am. Chem. Soc., 1997, 119, 8991–9001.

Mukkala, V. M. et al., "New Heteroaromatic Complexing Agents and Luminescence of Their Europium (III) and Terbium (III) Chelates", Helvetica Chimica Acta, vol. 75, (1992) 1621–1632.

Muri, E.M.F. et al., "Synthesis of New Benzylic Ethers of Oximes Derived From 1–Phenyl–Pyrazole Compounds", Synthetic Communications, 28(7), 1299–1321 (1998).

(List continued on next page.)

Primary Examiner—Elli Peselev
(74) Attorney, Agent, or Firm—Joseph S. Kentoffio

(57) ABSTRACT

6-O-Carbamoyl ketolide antibacterials of the formula:

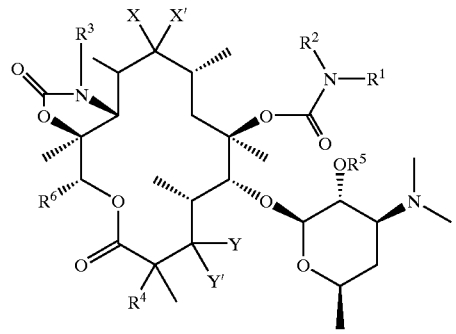

wherein $R^1$, $R^2$, $R^3$, $R^4$, $R^5$, $R^6$, X, X', Y, and Y' are as described herein and in which the substituents have the meaning indicated in the description. These compounds are useful as antibacterial agents.

54 Claims, No Drawings

OTHER PUBLICATIONS

Nerenz, H. et al., "Nonlinear Optical Chromophores with Isoquinolines, thieno[2,3-c]-pyridines and 2-(2+-thienyl)pyridines as Inherently Polarized π-electron bridges", J. Chem. Soc., Perkin Trans., 2, 1998, 437–447.

Sutherland, J.D. et al., "Studies on a Potentially Prebiotic Synthesis of RNA", Tetrahedron, vol. 53, no. 34, 1997, 11595–11626.

Tanaka, A. et al., "Inhibitors of Acyl–CoA:Cholesterol O–Acyltransferase. 2. Identification and Structure–Activity Relationships of a Novel Series of N–Alkyl–N–(heteroaryl–substituted benzyl)–N'–arylureas[1]", J. Med. Chem. 1998, 41, 2390–2410.

Vacher, B. et al., "Design and Synthesis of a Series of 6–Substituted–2–pyridinylmethylamine Derivatives as novel, High–Affinity, Selective Agonists at $5-HT_{1A}$ Receptors", J. Med. Chem. 1998, 41, 5070–5083.

Yamada, A. et al., "Development of Chemical Substances Regulating Biofilm Formation", Bull, Chem. Soc. Jpn., 70, 3061–3069 (1997).

Constantin Agouridas et al., "Synthesis and Antibacterial Activity of Ketolides (6–0–Methyl–3–oxoerythromycin Derivatives): A New Class of Antibacterials Highly Potent Against Macrolide–Resistant and –Susceptible Respiratory Pathogens", J. Med. Chem., vol. 41 No. 21, pp. 4080–4100, (1998).

Alexis Denis et al., "β–Keto–Ester Chemistry and Ketolides. Synthesis and Antibacterial Activity of 2–Halogeno, 2–Methyl and 2,3 Enol–Ether Ketolides", Bioorganic & Medicinal Chemistry Letters, Oxford GB, vol. 10 No. 17, pp. 2019–2022 (Sep. 2000).

* cited by examiner

6-O-CARBAMOYL KETOLIDE ANTIBACTERIALS

CROSS REFERENCE TO RELATED APPLICATIONS

The present application is a continuation-in-part of prior application Ser. No. 09/773,788, filed Feb. 1, 2001, now U.S. Pat. No. 6,472,372. The present application also claims the benefit under 35 U.S.C. §119(e) of prior application Ser. No. 60/251,547, filed Dec. 6, 2000.

FIELD OF THE INVENTION

The present invention relates to the field of macrolide compounds having antibacterial activity, pharmaceutical compositions containing the compounds, and methods of treating bacterial infections with the compounds.

BACKGROUND OF THE INVENTION

Erythromycins are well-known antibacterial agents widely used to treat and prevent bacterial infection caused by Gram-positive and Gram-negative bacteria. However, due to their low stability in acidic environment, they often carry side effects such as poor and erratic oral absorption. As with other antibacterial agents, bacterial strains having resistance or insufficient susceptibility to erythromycin have developed over time and are identified in patients suffering from such ailments as community-acquired pneumonia, upper and lower respiratory tract infections, skin and soft tissue infections, meningitis, hospital-acquired lung infections, and bone and joint infections. Particularly problematic pathogens include methicillin-resistant *Staphylococcus aureus* (MRSA), vancomycin-resistant enterococci (VRE) and penicillin- and macrolide-resistant *Streptococcus pneumoniae*. Therefore, continuing efforts are called for to identify new erythromycin derivative compounds with improved antibacterial activity, and/or unanticipated selectivity against various target microorganisms, particularly erythromycin-resistant strains.

The following references relate to various erythromycin derivatives disclosed as having antibacterial activity:

EP 216,169 and U.S. Pat. No. 4,826,820 to Brain et al. disclose antibacterially active 6-carbamate erythromycin derivatives stated to "have antibacterial properties, in particular against Gram-positive bacteria but also against some Gram-negative bacteria."

U.S. Pat. No. 5,444,051, No. 5,561,118, and No. 5,770,579, all to Agouridas et al., disclose erythromycin compounds such as those of the formulae

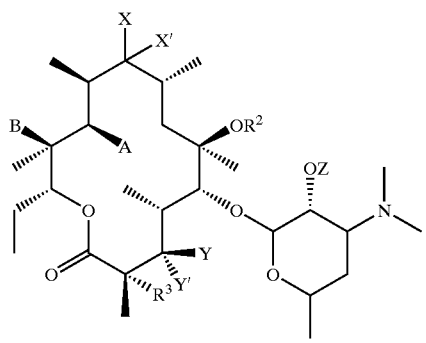

wherein substituents are as described in the respective references, which are all stated to be useful as antibiotics.

U.S. Pat. No. 5,866,549 to Or et al. and WO 98/09978 (Or et al.) disclose 6-O-substituted ketolides stated to have increased acid stability relative to erythromycin A and 6-O-methyl erythromycin A and enhanced activity toward gram negative bacteria and macrolide resistant gram positive bacteria.

WO 97/17356 (Or et al.) discloses tricyclic erythromycin derivatives stated to be useful in the treatment and prevention of bacterial infections.

WO 99/21871 (Phan et al.) discloses 2-halo-6-O-substituted ketolide derivatives of the formula

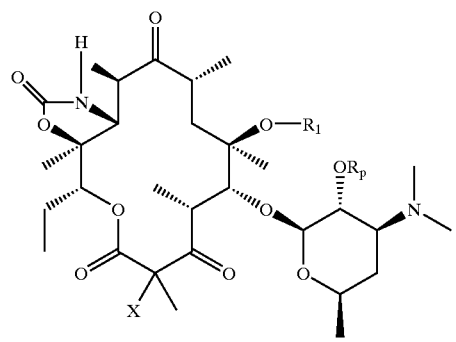

wherein substituents are as described in the respective reference, which are stated to possess antibacterial activity.

WO 99/21864 (Or et al.) discloses 6,11-bridged erythromycin derivatives having antibacterial activity.

EP1146051 to Kaneko et al. discloses macrolide compounds of the following formula that are useful as antibacterial and antiprotozoal agents in mammals,

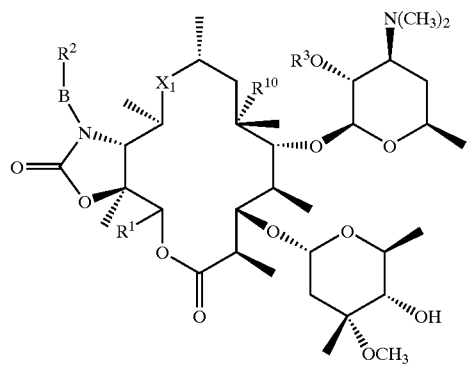

wherein substituents are as described in the reference.

WO 00/75156 (Phan et al.) discloses 6-O-carbamate ketolide derivatives that are useful as antibacterials for the treatment and prevention of infections in a mammal.

SUMMARY OF THE INVENTION

The invention provides compounds of Formula 1:

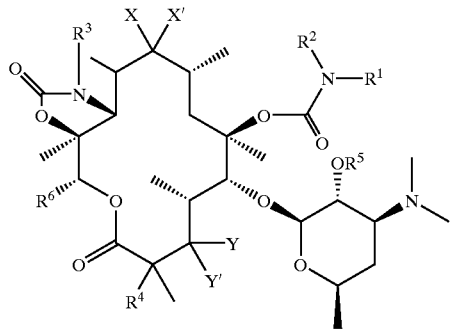

Formula 1

Wherein

R$^1$ and R$^2$ are independently selected from hydrogen, optionally substituted —CR$_f$R$_g$(C$_1$–C$_8$)alkyl, optionally substituted —CR$_f$R$_g$(C$_2$–C$_8$)alkenyl, optionally substituted —CR$_f$R$_g$(C$_2$–C$_8$)alkynyl, optionally substituted cycloalkyl, and optionally substituted (C$_5$–C$_7$)-cycloalkenyl, provided that R$^1$ and R$^2$ are not both hydrogen, wherein the substituents are selected from halogen, alkyl, alkenyl, alkynyl, cycloalkyl, oxo, aryl, heteroaryl, heterocyclo, CN, nitro, —COOR$_a$, —OCOR$_a$, —OR$_a$, —SR$_a$, -SOR$_a$, —SO$_2$R$_a$, —NR$_a$R$_b$, —CONR$_a$R$_b$, —OCONR$_a$R$_b$, —NHCOR$_a$, —NHCOOR$_a$, and —NHCONR$_a$R$_b$, wherein R$_a$ and R$_b$ are independently selected from hydrogen, alkyl, alkenyl, alkynyl, cycloalkyl, aryl, heteroaryl, heterocyclo, aralkyl, heteroaralkyl, and heterocycloalkyl; and R$_f$ and R$_g$ are independently selected from the group consisting of hydrogen, alkyl, alkenyl, alkynyl, cycloalkyl, aryl, heteroaryl, heterocyclo, COOR$_a$, and CONR$_a$R$_b$;

or R$^1$ and R$^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —COOR$_a$, —OCOR$_a$, —OR$_a$, —SR$_a$, —SOR$_a$, —SO$_2$R$_a$, —NR$_a$R$_b$, —CONR$_a$R$_b$, —OCONR$_a$R$_b$, —NHCOR$_a$, —NHCOOR$_a$, and —NHCONR$_a$R$_b$;

R$^3$ is hydrogen or —W—V, wherein

W is selected from the group consisting of (a) —NH—(CH$_2$)$_p$—, (b) —(CH$_2$)$_q$—, (c) —O—(CH$_2$)$_r$—, (d) —NH—C$_1$–C$_6$alkenyl-, (e) —C$_1$–C$_6$alkenyl-, (f) —O—C$_1$–C$_6$alkenyl-, (g) —NH—C$_1$–C$_6$alkynyl-, (h) —C$_1$–C$_6$alkynyl-, and (i) —O—C$_1$–C$_6$alkynyl-;

p is 0 to 5;

q is 0 to 5; and r is 0 to 5;

and

V is selected from the group consisting of (a) hydrogen, (b) aryl, (c) substituted aryl, (d) heteroaryl, (e) substituted heteroaryl, and (f) Ar$_1$—Ar$_2$, wherein Ar$_1$ and Ar$_2$ are independently selected from the group consisting of (i) aryl, (ii) substituted aryl, (iii) heteroaryl, and (iv) substituted heteroaryl;

R$^4$ is selected from hydrogen, halogen, and hydroxy;

R$^5$ is hydrogen or a hydroxy protecting group;

R$^6$ is selected from hydrogen, alkyl, C$_2$–C$_{10}$-alkenyl, C$_2$–C$_{10}$-alkynyl, aryl, heteroaryl, heterocyclo, aryl(C$_1$–C$_{10}$)alkyl, aryl(C$_2$–C$_{10}$)alkenyl, aryl(C$_2$–C$_{10}$)alkynyl, heterocyclo(C$_1$–C$_{10}$)alkyl, heterocyclo(C$_2$–C$_{10}$)alkenyl, and heterocyclo(C$_2$–C$_{10}$)alkynyl, C$_3$–C$_6$-cycloalkyl, C$_5$–C$_8$-cycloalkenyl, alkoxyalkyl containing 1–6 carbon atoms in each alkyl or alkoxy group, and alkylthioalkyl containing 1–6 carbon atoms in each alkyl or thioalkyl group;

X and X', together with the carbon atom to which they are attached, form C=O, C=NR$_c$, or C=NOR$_c$, wherein R$_c$ is independently selected from hydrogen, alkyl, alkenyl and alkynyl; and Y and Y', together with the carbon atom to which they are attached, form C=O, —CHOH, C=NR$_c$, or C=NOR$_c$, wherein R$_c$ is independently selected from hydrogen, alkyl, alkenyl and alkynyl;

or an optical isomer, enantiomer, diastereomer, racemate or racemic mixture thereof, or a pharmaceutically acceptable salt, esters or pro-drugs thereof.

Compounds of the above formula are useful as antibacterial agents for the treatment of bacterial infections in a subject such as human and animal.

The present invention is also directed to a method of treating a subject having a condition caused by or contributed to by bacterial infection, which comprises administering to said subject a therapeutically effective amount of the compound of Formula 1.

The present invention is further directed to a method of preventing a subject from suffering from a condition caused by or contributed to by bacterial infection, which comprises administering to the subject a prophylactically effective amount of the compound of Formula 1.

Other objects and advantages will become apparent to those skilled in the art from a review of the ensuing specification.

DETAILED DESCRIPTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon—carbon double bond. "Alkynyl" refers to a straight or branched chain hydrocarbon with at least one carbon—carbon triple bound. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. "Cycloalkenyl" groups contain 5 to 8 ring carbons and at least one carbon—carbon double bond. The alkyl, alkenyl, alkynyl, cycloalkyl, cycloalkenyl, and alkoxy group may be independently substituted with one or more members of the group including, but not limited to, halogen, alkyl, alkenyl, alkynyl, cycloalkyl, alkoxy, oxo, aryl, heteroaryl, heterocyclo, CN, nitro, —OCOR$_a$, —OR$_a$, —SR$_a$, —SOR$_a$, —SO$_2$R$_a$, —COOR$_a$, —NR$_a$R$_b$, —CON$_a$R$_b$, —OCONR$_a$R$_b$, —NHCOR$_a$, —NHCOOR$_a$, and —NHCONR$_a$R$_b$, wherein R$_a$ and R$_b$ are independently selected from H, alkyl, alkenyl, alkynyl, cycloalkyl, aryl, heteroaryl, heterocyclo, aralkyl, heteroaralkyl, and heterocycloalkyl. "Aralkyl," "heteroaralkyl," and "heterocycloalkyl" are alkyl groups substituted with aryl, heteroaryl, and heterocyclo, respectively. "Arylalkenyl," "heteroarylalkenyl," and "heterocycloalkenyl" are alkenyl groups substituted with aryl, heteroaryl, and heterocyclo, respectively. "Arylalkynyl," "heteroarylalkynyl," and "heterocycloalkynyl" are alkynyl groups substituted with aryl, heteroaryl, and heterocyclo, respectively.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo and iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, C$_1$–C$_8$-alkyl, aryl, heteroaryl, heterocyclo, C$_1$–C$_8$-alkoxyl, C$_1$–C$_8$-alkylthio, C$_1$–C$_8$-alkyl-amino, di(C$_1$–C$_8$-alkyl)amino, (mono-, di-, tri-, and per-) halo-alkyl, formyl, carboxy, alkoxycarbonyl, C$_1$–C$_8$-alkyl-CO—O—, C$_1$–C$_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0–3 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, indazolyl, indolizinyl, benzofuryl, cinnolinyl, quinoxalinyl, pyrrolopyridinyl, furopyridinyl (such as furo[2,3-c]pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with halogen, OH, CN, mercapto, nitro, amino, C$_1$–C$_8$-alkyl, aryl, heteroaryl, heterocyclo, C$_1$–C$_8$-alkoxyl, C$_1$–C$_8$-alkylthio, C$_1$–C$_8$-alkyl-amino, di(C$_1$–C$_8$-alkyl)amino, (mono-, di-, tri-, and per-) halo-alkyl, formyl, carboxy, alkoxycarbonyl, C$_1$–C$_8$-alkyl-CO—O—, C$_1$–C$_8$-alkyl-CO—NH—, or carboxamide. Heteroaryl may be substituted with a mono-oxo to give for example a 4-oxo-1 H-quinoline.

The terms "heterocycle," "heterocyclic," and "heterocyclo" refer to an optionally substituted, fully saturated, partially saturated, or non-aromatic cyclic group which is, for example, a 3- to 7-membered monocyclic, 7- to 11-membered bicyclic, or 10- to 15-membered tricyclic ring system, which has at (east one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzothiopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like. The heterocyclic group may be substituted by independent replacement of 1 to 3 hydrogen atoms thereon with OH, CN, mercapto, nitro, amino, C$_1$–C$_8$-alkyl, aryl, heteroaryl, heterocyclo, C$_1$–C$_8$-alkoxyl, C$_1$–C$_8$-alkylthio, C,-C$_8$-alkyl-amino, di(C$_1$–C$_8$-alkyl)amino, (mono-, di-, tri-, and per-) halo-alkyl, formyl, carboxy, alkoxycarbonyl, C$_1$–C$_8$-alkyl-CO—O—, C$_1$–C$_8$-alkyl-CO—NH—, or carboxamide.

Substituted aryl, substituted heteroaryl, and substituted heterocycle may also be substituted with a second substituted-aryl, a second substituted-heteroaryl, or a second substituted-heterocycle to give, for example, a 4-pyrazol-1-yl-phenyl or 4-pyridin-2-yl-phenyl.

Designated numbers of carbon atoms (e.g., C$_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyidiphenylsilyl, ethyidiphenylsilyl, and t-butyidiphenylsilyl; acyl and aroyl such as acetyl, pivaloylbenzoyl, 4-methoxybenzoyl, and 4-nitrobenzoyl; and alkoxycarbonyl such as methoxycarbonyl, ethoxycarbonyl, benzyloxycarbonyl.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Included within the scope of the invention are the hydrated forms of the compounds which contain various amounts of water, for instance, the hydrate, hemihydrate, and sesquihydrate forms. The present invention also includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" includes, without limitation, any animal or artificially modified animal. As a particular embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals.

In particular, compounds of Formula 1 wherein $R^1$ and $R^2$ are independently selected from hydrogen, substituted $C_1$–$C_8$-alkyl, substituted —$CH_2C_2$–$C_8$-alkenyl, and substituted —$CH_2C_2$–$C_8$-alkynyl, wherein the substituents are selected from CN, nitro, —COOR$_a$, —OCOR$_a$, —OR$_a$, —SR$_a$, —SOR$_a$, —SO$_2$R$_a$, —NR$_a$R$_b$, —CON$_a$R$_b$, —OCONR$_a$R$_b$, —NHCOR$_a$, —NHCOOR$_a$, and —NHCONR$_a$R$_b$, wherein R$_a$ and R$_b$ are independently selected from hydrogen, alkyl, alkenyl, alkynyl, cycloalkyl, aryl, heteroaryl, heterocyclo, aralkyl, heteroaralkyl, and heterocycloalkyl; provided that $R^1$ and $R^2$ are not both hydrogen;

$R^3$ is hydrogen;

$R^4$ is selected from hydrogen, halogen, and hydroxy;

$R^5$ is hydrogen or a hydroxy protecting group;

$R^6$ is selected from hydrogen, alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$)alkenyl, aryl($C_2$–$C_{10}$)alkynyl, heterocyclo($C_1$–$C_{10}$)alkyl, heterocyclo($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

X and X', together with the carbon atom to which they are attached, form C=O, C=NR$_c$, or C=NOR$_c$, wherein R$_c$ is independently selected from hydrogen, alkyl, alkenyl and alkynyl; and Y and Y', together with the carbon atom to which they are attached, form C=O, —CHOH, C=NR$_c$, or C=NOR$_c$, wherein R$_c$ is independently selected from hydrogen, alkyl, alkenyl and alkynyl are embodiments of the present invention for such purposes. More particularly, $R^2$ is hydrogen, $R^4$ is hydrogen or fluorine, X and X' form C=O together with the carbon atom to which they are attached, and Y and Y' form C=O together with the carbon atom to which they are attached.

Compounds of Formula 1, which are represented by Formula 1':

Formula 1'

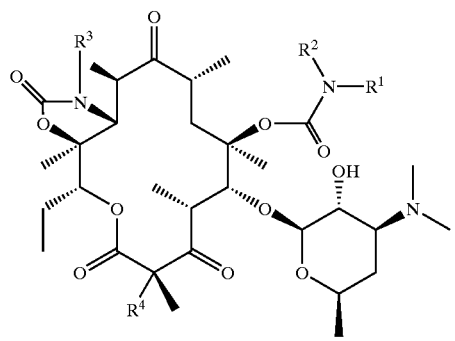

wherein $R^1$, $R^2$, $R^3$, and $R^4$ are as described above are also embodiments of this invention. More particularly, $R^2$ and $R^3$ are hydrogen and $R^4$ is fluorine.

Compounds of Formula 1, which are represented by Formula 1":

Formula 1"

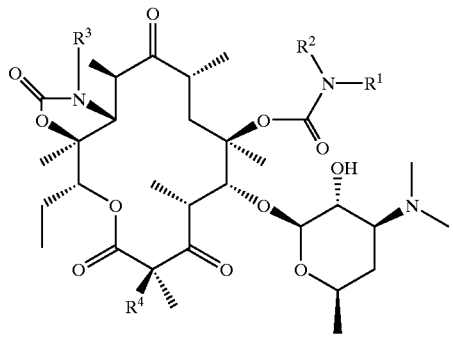

wherein $R^1$, $R^2$, $R^3$, and $R^4$ are as described above, are further embodiments of this invention. More particularly, $R^2$ and $R^3$ are hydrogen and $R^4$ is fluorine.

Compounds of Formula 1 wherein $R^5$ may be selected from acyl and aroyl are further embodiments of this invention.

This invention also provides processes for preparing the instant compounds.

The compounds of Formula I may be prepared from readily available starting materials such as erythromycin and erythromycin derivatives well known in the art. Outlined in Schemes 1 through 18 are representative procedures to prepare the compounds of the instant invention:

Scheme 1

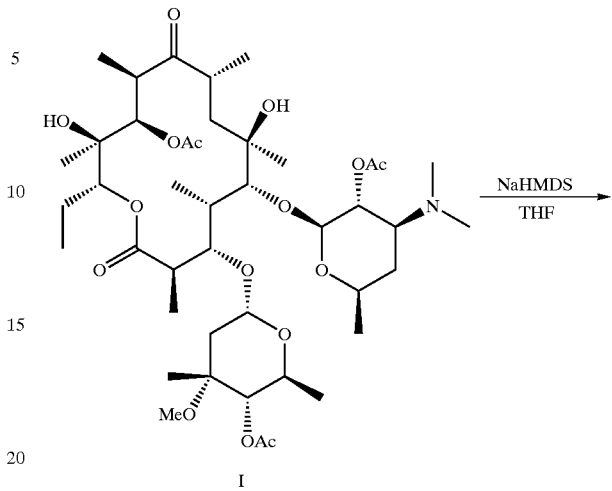

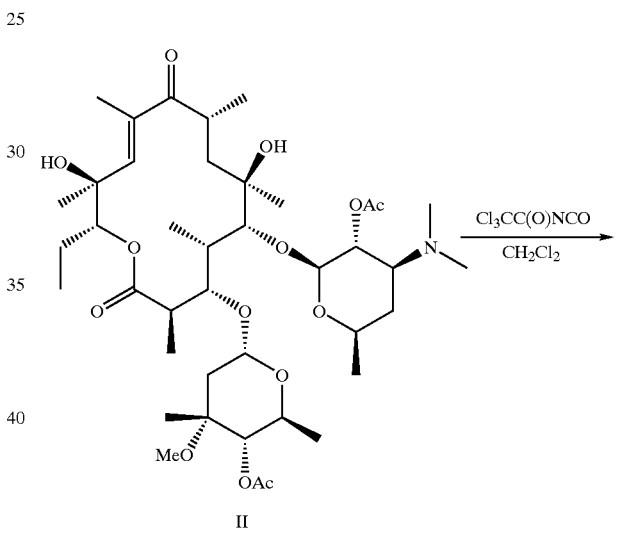

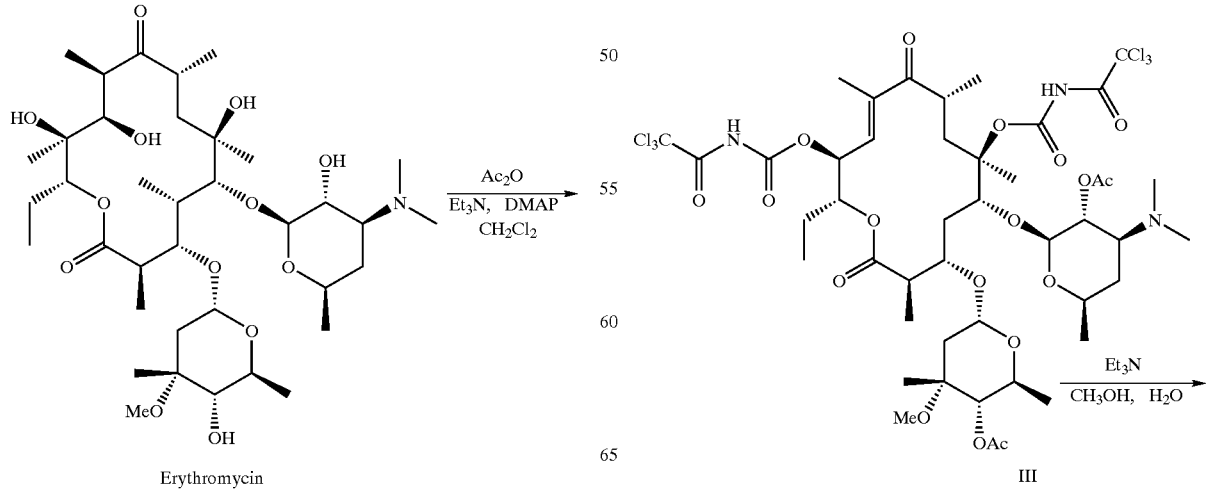

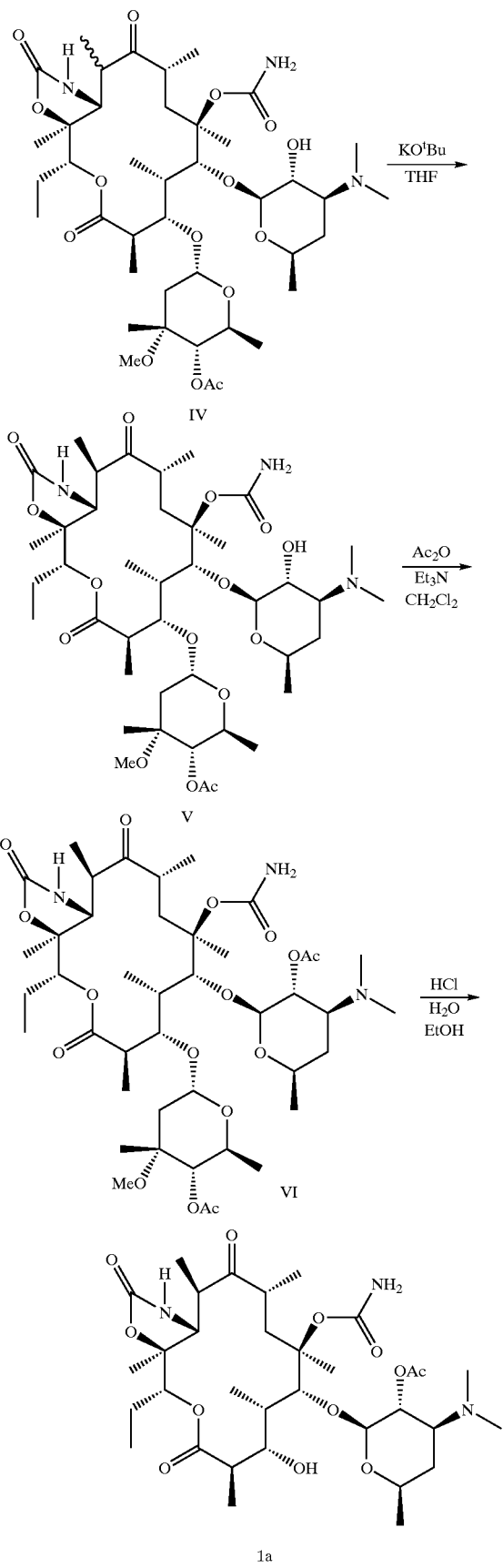

Scheme I illustrates the method of synthesis of the 2',4"-diacetyl-6-carbamyl-11,12-dideoxy-11,12-iminocarbonyloxyerythromycin A (VI) and the 2'-acetyl-6-carbamyl-11,12-dideoxy-3-O-descladinosyl-11,12-iminocarbonyloxyerythromycin A (1a) precursors to the compounds of the invention.

Erythromycin A is treated with acetic anhydride in the presence of a tertiary amine base, such as triethylamine, diisopropylethylamine, or pyridine, and an acylation catalyst, such as DMAP, in a suitable solvent such as methylene chloride, chloroform or THF at a temperature ranging from −20° C. to 37° C. for 2 to 48 hours to afford 2',4",11-triacetylerythromycin A (I). The 10,11-anhydro derivative (II) can be readily obtained by treatment of I with a base in an inert solvent such as THF, dioxane, DME, or DMF at a temperature ranging from −78° C. to 80° C. for 1–24 hours. Suitable bases to effect the elimination reaction include, but are not limited to, sodium hexamethyldisilazide, potassium hexamethyldisilazide, LDA, lithium tetramethylpiperidide, DBU, and tetramethylguanidine. It will be apparent to one skilled in the art that alternative methods for synthesis of 2',4"-diacetyl-10,11-anhydroerythromycin A are available, including conversion of erythromycin A to the 11,12-cyclic carbonate derivative with ethylene carbonate, followed by elimination with tetramethylguanidine, as described in Hauske, J. R. and Kostek, G., *J. Org. Chem.* 1982, 47,1595. Selective protection of the 2' and 4"-hydroxyl groups can then be readily accomplished with acetic anhydride in the presence of a tertiary amine base. Likewise, alternative protecting group strategies may be employed. For example, erythromycin A may be treated with benzoic anhydride, propionic anhydride, or formic acetic anhydride under similar conditions as described above to obtain the 2',4",11-triacylated erythromycin A derivative followed by elimination to afford the corresponding 10,11-anhydro compound.

Once the suitably protected 10,11-anhydro derivative is obtained, derivatization of both tertiary hydroxyl groups can be carried out by treatment with trichloroacetylisocyanate in an inert solvent, such as methylene chloride, chloroform, or THF at a temperature ranging from −20° C. to 37° C. for 1–24 hours to yield the di-(N-trichloroacetyl)carbamate derivative (III). The N-trichloroacetylcarbamate functionalities can be hydrolyzed to the corresponding primary carbamates by treatment with a suitable base, such as triethylamine, in an aqueous solvent mixture, such as methanol/water for 1–24 hours at a temperature ranging from 20° C. to 80° C. Alternative bases may likewise be used to effect this conversion, such as sodium hydroxide, potassium hydroxide, sodium carbonate and potassium carbonate. Under the reaction conditions, the primary carbamate formed at the 12-position undergoes spontaneous Michael addition to the electrophilic 11-position of the α,β-unsaturated ketone and the 2'-acetoxy group is hydrolyzed to the corresponding hydroxyl to afford the cyclic carbamate derivative (IV). Compound IV is generally isolated as a mixture of methyl epimers at the C10-position, which can be readily converted to the desired C10-β-methyl epimer (V) by treatment with an equilibrating base, such as potassium t-butoxide, tetramethylguanidine, or DBU in a suitable solvent, such as THF, dioxane, DME, DMF or t-butanol at a temperature ranging from −78° C. to 80° C. for 1 to 24 hours. Reprotection of the 2'-hydroxyl group to give VI can be carried out by treatment with acetic anhydride in the presence of a tertiary amine base, such as triethylamine, diisopropylethylamine, or pyridine, and optionally an acylation catalyst, such as DMAP, in a suitable solvent such as methylene chloride, chloroform or THF at a temperature ranging from −20° C. to 37° C. for 2 to 48 hours. It is understood that an orthogonal protection strategy of the sugar hydroxyls may also be employed by treatment of V with alternate reagents such as benzoic anhydride, benzyl chloroformate, hexamethyidisilazane, or a trialkylsilyl chloride. Finally, selective removal of the cladinose sugar can be accomplished by reaction of VI with an acid, such as hydrochloric, sulfuric, chloroacetic, and trifluoroacetic, in the presence of alcohol and water to afford 1a. Reaction time is typically 0.5–24 hours at a temperature ranging from −10° C. to 37° C.

Scheme 2

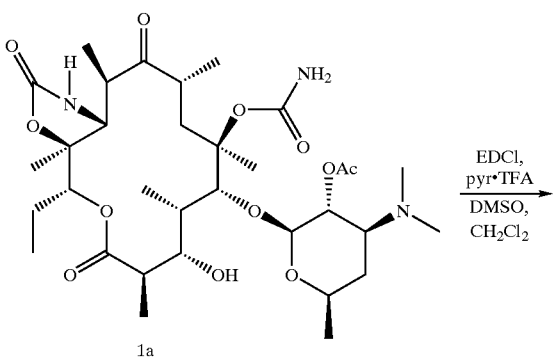

1a

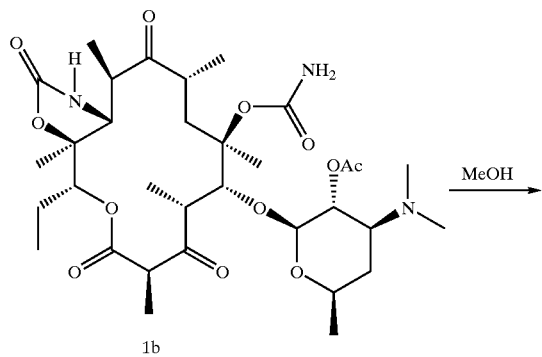

1b

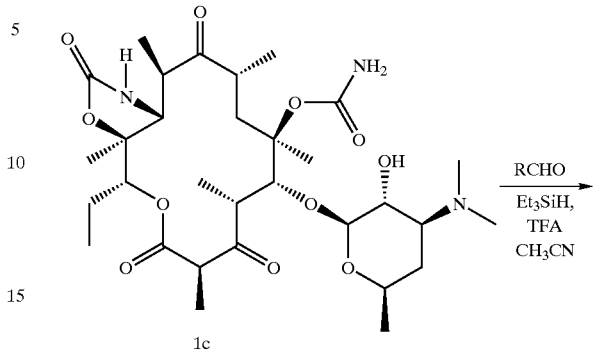

1c

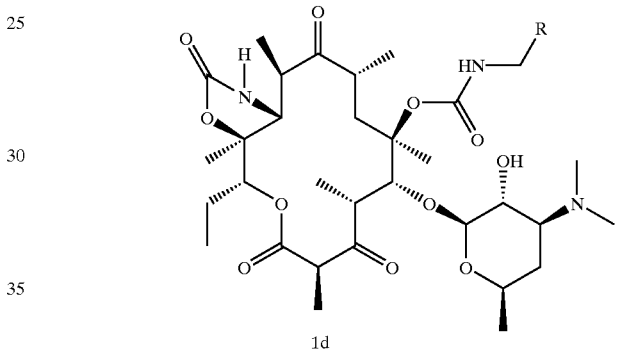

1d

Scheme 2 depicts synthesis of compounds of formulae 1b, 1c and 1d, wherein RCHO is an aldehyde (R may be a member of the group including, but not limited to, hydrogen, alkyl, alkenyl, alkynyl, cycloalkyl, aryl, heteroaryl, heterocycle, arylalkenyl, arylalkynyl, aralkyl, heteroarylalkenyl, heteroarylalkynyl, heteroarylalkyl, heterocycloalkenyl, heterocycloalkynyl, and heterocycloalkyl). Oxidation of the 3-hydroxy group of 1a to yield compound 1b can be effected with DMSO and a carbodiimide, such as EDCI, in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Removal of the 2'-acetyl group of compound 1b is readily accomplished by transesterification with methanol for 2–48 hours at a temperature ranging from −20° C. to 60° C. to yield compound 1c. Alternative methods for deprotection of the 2'-acetyl group include hydrolysis in the presence of an alkali metal hydroxide or alkali metal carbonate, such as sodium hydroxide or potassium carbonate, or ammonolysis with ammonia in methanol. Compounds of formula 1d can be obtained by selective alkylation of the primary carbamate of 1c with a suitably substituted aldehyde in the presence of a reducing agent and acid. Alternatively, the corresponding acetal may be used in place of the suitably substituted aldehyde in this reaction. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal.

Scheme 3

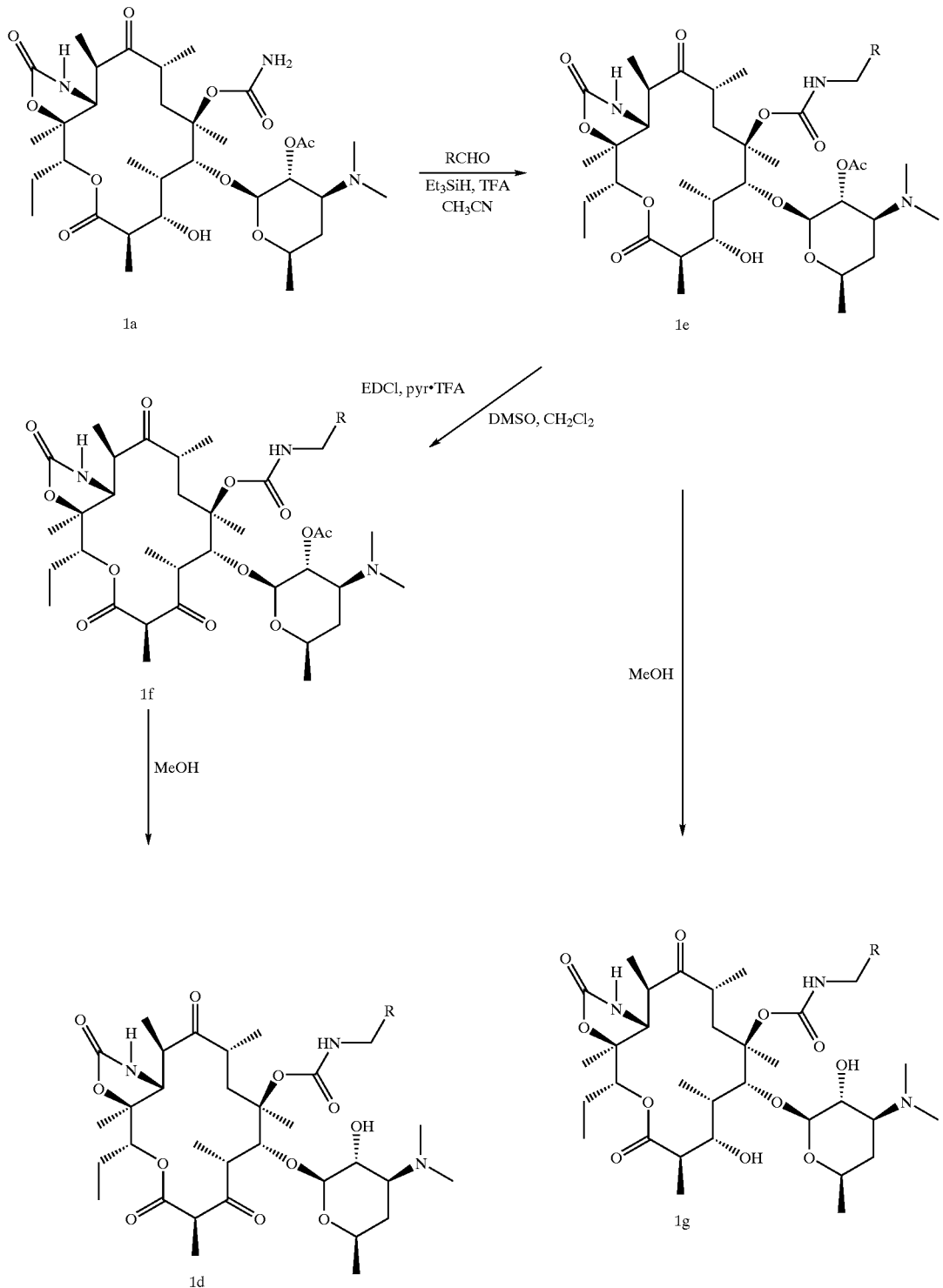

10It will be clear to one skilled in the art that the order of the steps in the synthetic sequence leading to compounds of the invention can be altered, provided that the functionality present in the molecule is compatible with the desired selective transformations. This is illustrated in Scheme 3. For example, compound 1a can be treated under similar conditions as described above for the reductive alkylation of compound 1c (Scheme 2) to yield compounds of the formula 1e. Removal of the 2'-acetyl group of compound 1e as described for the conversion of compound 1b to compound 1c (Scheme 2) provides compounds of formula 1g. Alternatively, oxidation of the 3-hydroxyl of compound 1e to the ketone of compound 1f can be conducted as described for the analogous transformation of 1a to 1b in Scheme 2. Finally, deprotection of the 2'-acetyl group of 1f is readily effected as described for the conversion of compound 1b to compound 1c (Scheme 2) to provide the compounds of formula 1d, wherein R is as previously defined.

-continued

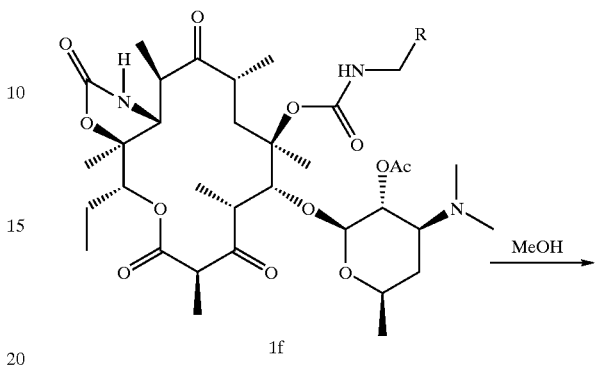

Scheme 4

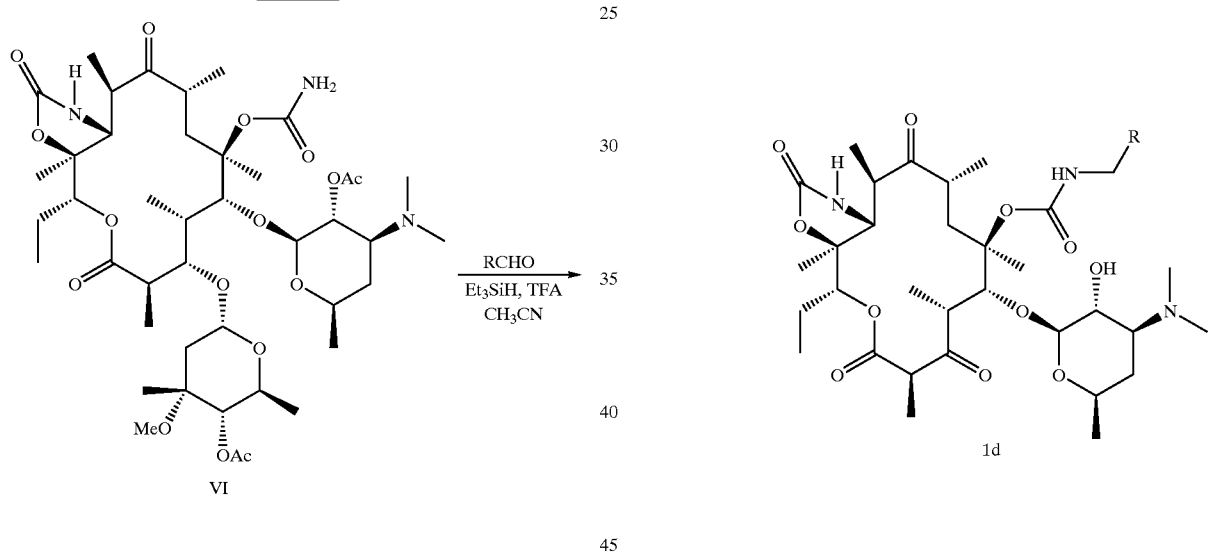

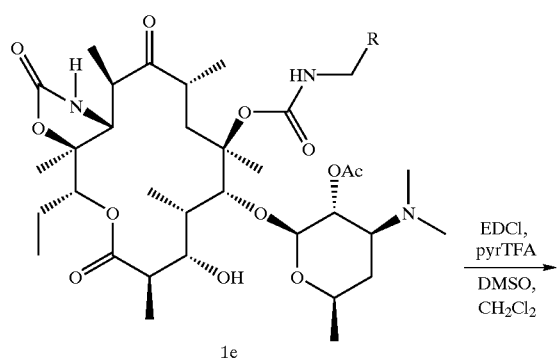

Scheme 4 illustrates an alternate route for the preparation of the compounds of the invention (1d). Reaction of compound VI with a suitably substituted aldehyde and a reducing agent, such as triethylsilane, in the presence of an acid, such as trifluoroacetic acid, in a suitable solvent, such as acetonitrile, methylene chloride, or toluene, at a temperature ranging from −20° C. to 100° C. for 2–96 hours leads to the simultaneous removal of the cladinose sugar and the selective alkylation of the primary carbamate to afford compound 1e. Alternatively, the corresponding acetal of the suitably substituted aldehyde may be used to effect this transformation. Conversion of compound 1e to compound 1f and compound 1f to compound 1d can be conducted as described above.

Scheme 5

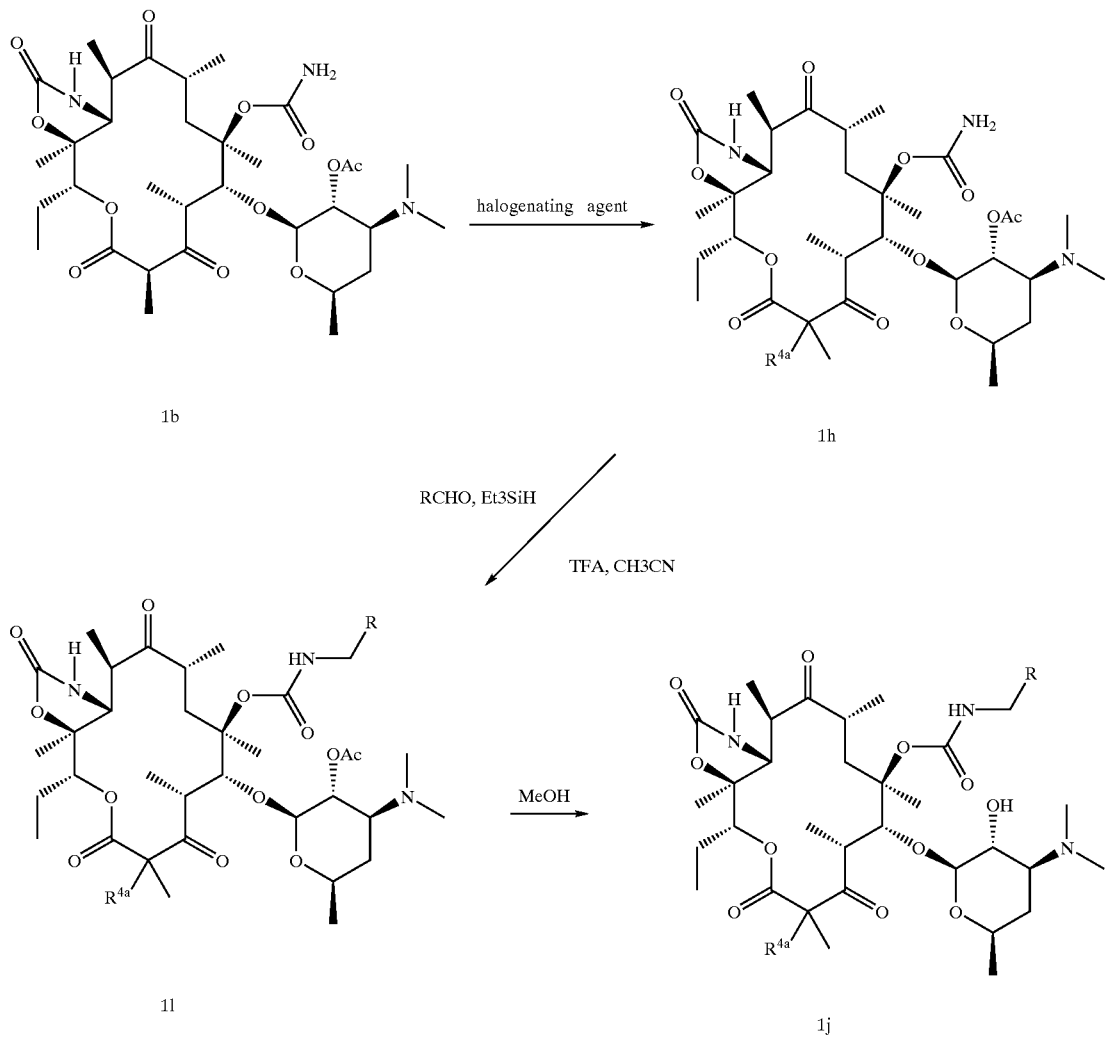

Scheme 5, wherein $R^{4a}$ is halogen and R is as described above, illustrates the procedures by which compounds of formula 1b can be converted to compounds of formula 1j.

Fluorination of compound 1b can be accomplished with any one of a number of fluorinating reagents, including N-fluorobenzenesulfonimide in the presence of base, 1-(chloromethyl)-4-fluoro-1,4-diazoniabicyclo[2.2.2]octane bis[tetrafluoroborate] (SELECTFLUOR™) in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, and N-fluoroperfluoropiperidine in the presence of base to give 1h wherein $R^{4a}$ is F. Chlorination of 1b can be effected with hexachloroethane in the presence of base, sulfuryl chloride, thionyl chloride, trifluoromethanesulfonyl chloride in the presence of base, chlorine, or sodium hypochlorite in the presence of acetic acid to give 1 h wherein $R^{4a}$ is Cl. Suitable brominating agents would include pyridinium hydrobromide perbromide, bromine in acetic acid, N-bromosuccinimide in the presence of base, 1,2-dibromoethane in the presence of base, or carbon tetrabromide in the presence of base to give 1h wherein $R^{4a}$ is Br. Suitable iodinating agents include N-iodosuccinimide in the presence of base or iodine to give 1h wherein $R^{4a}$ is I.

Transformation of the halogenated derivatives 1h to the corresponding compounds of formula 1j can be accomplished through analogous synthetic routes as above. Reaction of 1h with a suitably substituted aldehyde or acetal in the presence of a reducing agent and acid yields compounds 1i. Reagent combinations for effecting this transformation include triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Compounds 1i are then converted to the corresponding compounds of formula 1j by reaction with methanol for 2–48 hours at a temperature ranging from −20° C. to 60° C.

It will be understood by one skilled in the art of organic synthesis that the halogenation reaction can also be conducted at a later stage in the synthetic sequence. For example, halogenation of compound 1f (Scheme 3) affords the corresponding 2-halo derivative, which likewise can be converted to compounds of the invention by deprotection of the 2'-acetyl group under the previously described conditions.

Scheme 6A
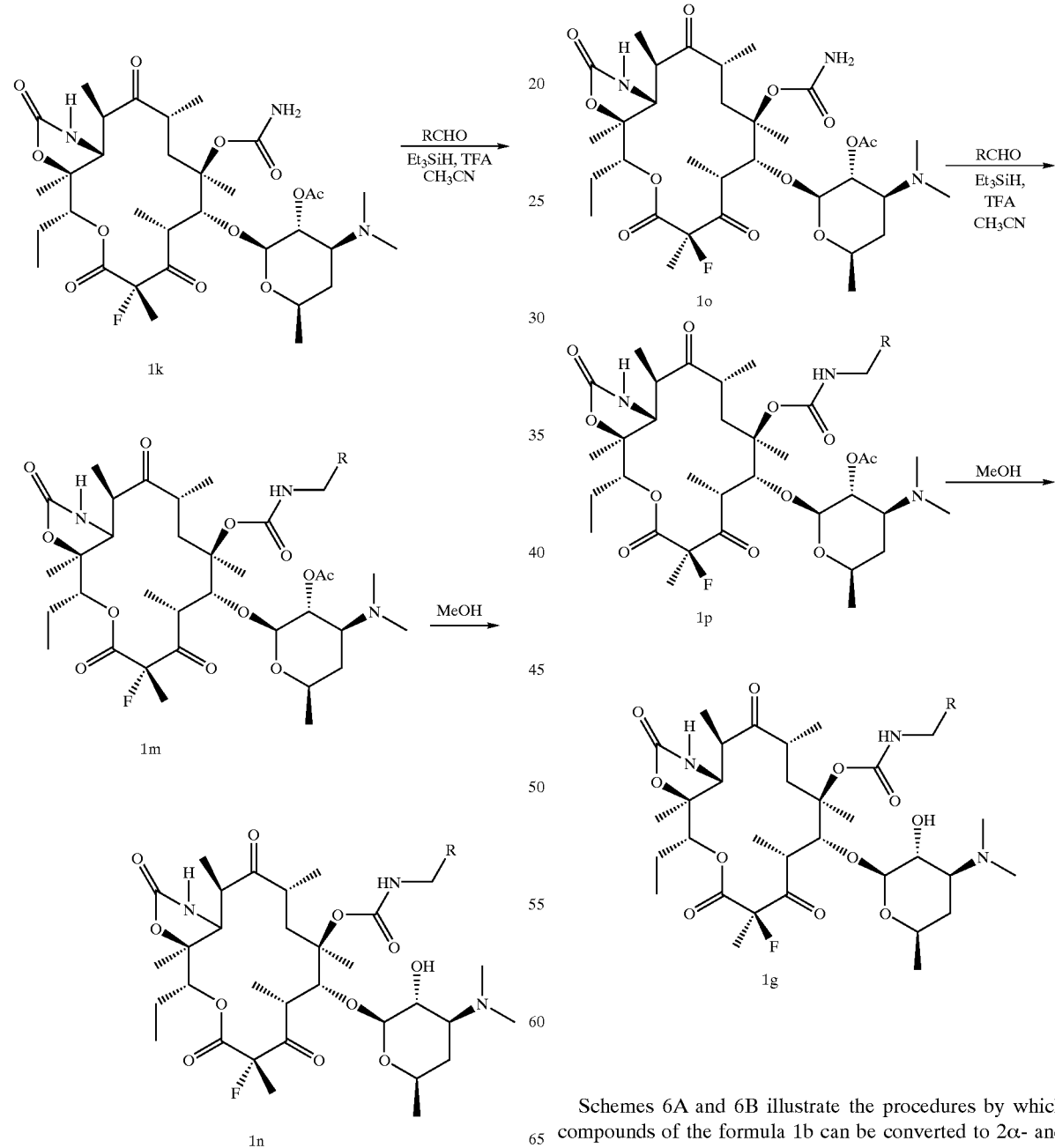
Scheme 6B
Schemes 6A and 6B illustrate the procedures by which compounds of the formula 1b can be converted to 2α- and 2β-fluoro derivatives of formulae 1n and 1q. Fluorination of compound 1b can be accomplished as described herein above. Reagent combinations for the conversion of compound 1b to the 2α-fluoro derivative 1k include SELECTFLUOR and sodium hexamethyldisilazide in DMF and N-fluorobenzenesulfonimide and potassium t-butoxide in THF. Typically, the reaction is conducted at −78° C. to −60° C. for 5 minutes to 24 hours. Reagent combinations for the conversion of compound 1b to the 2β-fluoro derivative 1o include N-fluorobenzenesulfonimide and sodium hydride in DMF. Typically, this reaction is conducted at 0° C. to 20° C. for 1 to 24 hours.

Transformation of the fluorinated derivatives 1k and 1o to the corresponding compounds of the invention 1n and 1q, respectively, can be accomplished through analogous synthetic routes as above. Reaction of 1k or 1o with a suitably substituted aldehyde or acetal in the presence of a reducing agent and acid yields compounds 1m and 1p, respectively. Reagent combinations for effecting this transformation include triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Compounds 1m and 1p are then converted to the corresponding compounds of the invention 1n and 1q, respectively, by reaction with methanol for 2–48 hours at a temperature ranging from −20° C. to 60° C.

It will be also understood by one skilled in the art of organic synthesis that the fluorination reaction can also be conducted at a later stage in the synthetic sequence. For example, fluorination of compound 1f (Scheme 3) affords the corresponding 2-fluoro derivative, which likewise can be converted to compounds of the invention by deprotection of the 2'-acetyl group under the previously described conditions.

Other compounds of the invention may also be suitable substrates for further transformation to yield other compounds of the present invention. Some of these transformations are illustrated in Schemes 7–11.

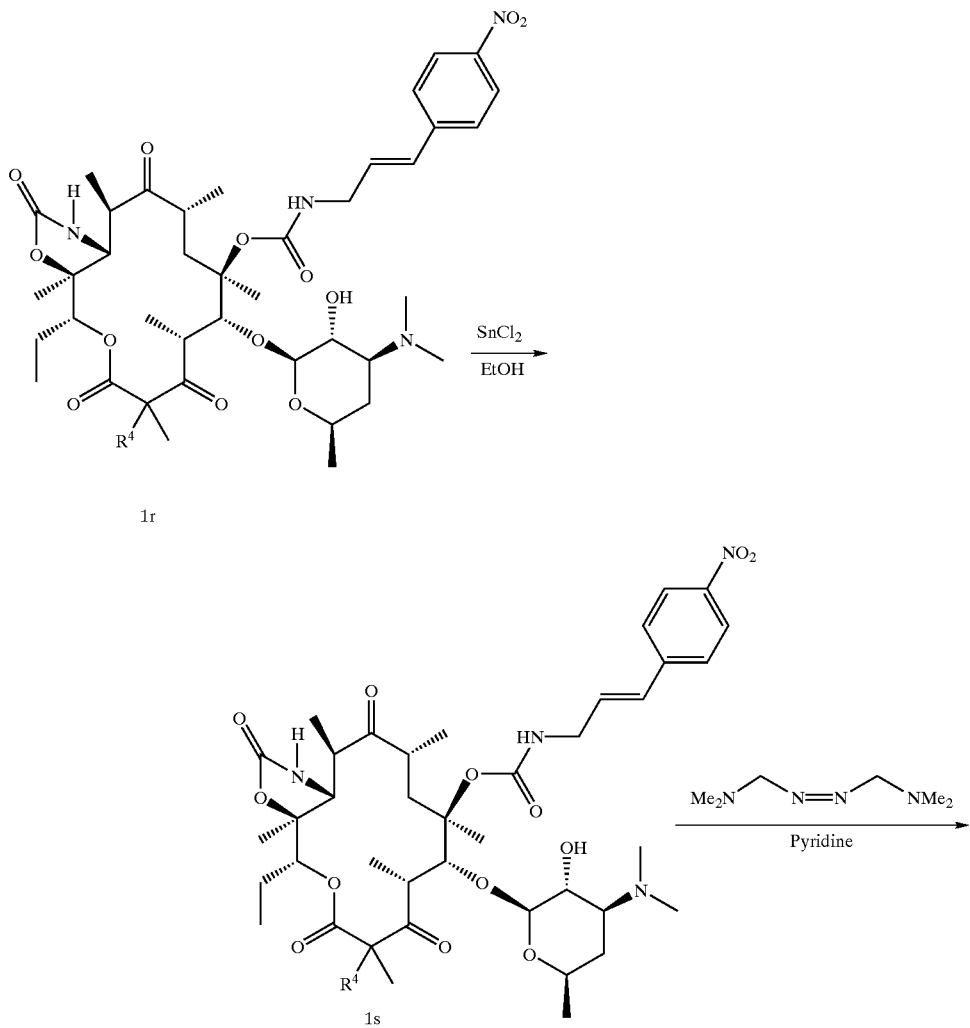

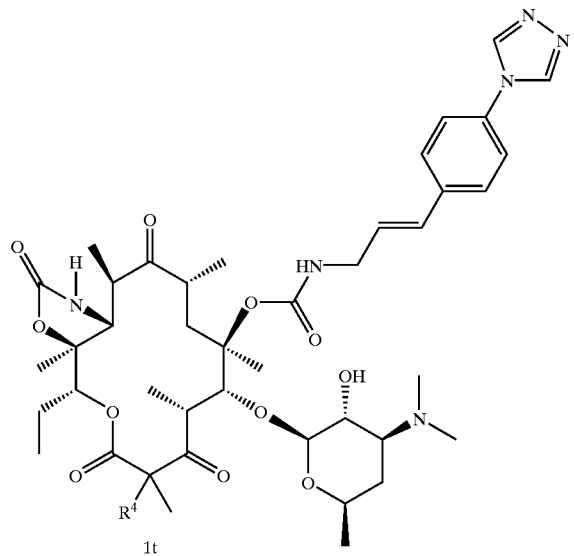

1t

Scheme 7 illustrates the conversion of the 3-(4-nitrophenyl)-2-propenyl analog (1r) to the 3-[4-(4H-1,2,3-triazol-4-yl)phenyl]-2-propenyl analog (1t) via the intermediacy of the 3-(4-aminophenyl)-2-propenyl derivative (1s) wherein $R^4$ is as described above. The selective reduction of the nitro group of 1r to the amine of 1s can be conducted with tin(II) chloride in ethanol at a temperature ranging from 20° C. to 78° C., typically for 1 to 24 hours. Alternative methods for reduction of the nitro group can also be employed, including iron/hydrochloric acid, iron/acetic acid, tin/hydrochloric acid, zinc/ammonium chloride, or sodium borohydride/nickel chloride. Conversion of the amino group of 1s to the 1,2,4-triazole of 1t is effected by condensation of the amine with N,N-dimethylformamide azine dihydrochloride in the presence of a base, such as pyridine. Reaction time is typically 2 to 72 hours at a temperature ranging from −20° C. to 115° C.

Scheme 8

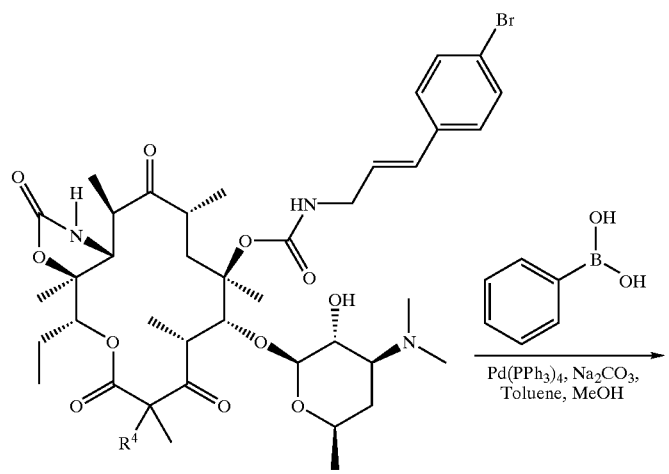

1u

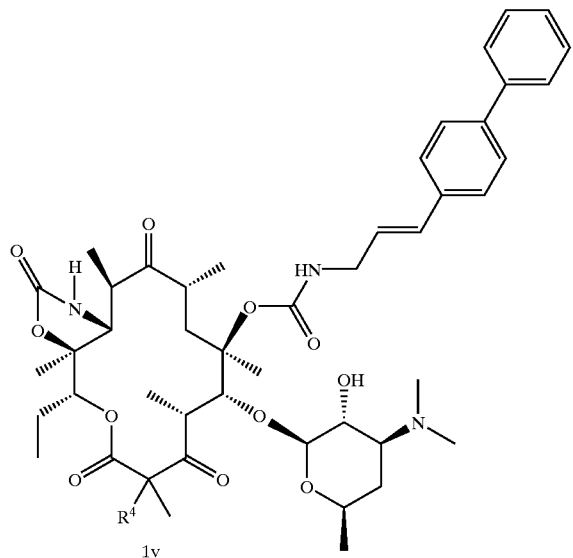

1v

Scheme 8 depicts the conversion of 3-(4-bromophenyl)-2-propenyl analog (1u) to the 3-(1,1'-biphen-4-yl)-2-propenyl analog (1v) wherein $R_4$ is as described above. Reaction of the aryl bromide with an aryl boronic acid derivative to give the biaryl derivative is conducted under typical Suzuki coupling conditions, i.e., in the presence of a $Pd^0$ catalyst, typically palladium tetrakistriphenylphosphine, and a base, typically sodium carbonate, potassium carbonate, potassium bicarbonate, potassium phosphate, or triethylamine in a suitable solvent, such as toluene, ethanol, methanol, DME, or THF. Reaction time is typically 2 to 48 hours at a temperature ranging from 20° C. to 110° C. Aryl iodides and aryl triflates are also suitable substrates for this conversion.

Scheme 9

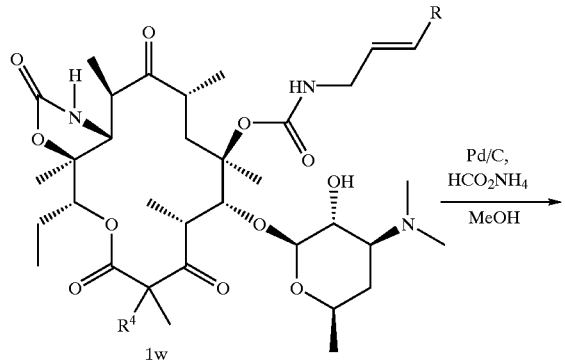

1w

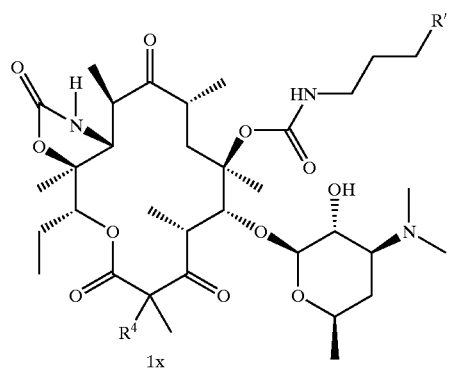

1x

Scheme 9 illustrates the conversion of a substituted N-propenylcarbamate derivative (1w) to the corresponding substituted N-propylcarbamate compound (1x), wherein R' may be a member of the R group except alkenyl and alkynyl, and R and $R^4$ is as described above. Typically, this transformation is conducted via catalytic transfer hydrogenation, in which the olefin is reacted with ammonium formate in the presence of a suitable catalyst, such as palladium on carbon, in a suitable solvent, such as methanol or ethanol, at a temperature ranging from 20° C. to 60° C. for 15 minutes to 24 hours. Other methods for reduction of the double bond could also be applicable, for example treatment with hydrogen in the presence of a noble metal catalyst, such as palladium or platinum. It will be obvious to one skilled in the art that the analogous N-propynylcarbamate may likewise be reduced to the corresponding N-propylcarbamate under similar conditions.

Scheme 10

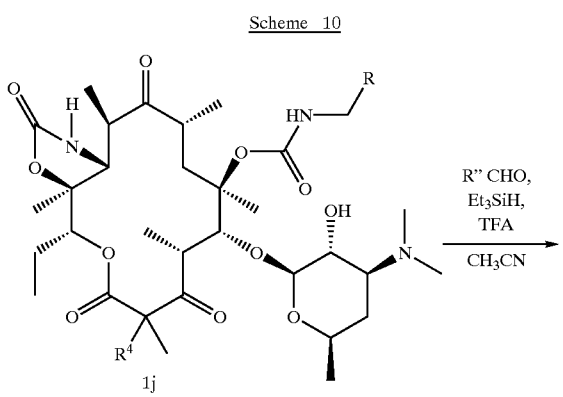

Scheme 11

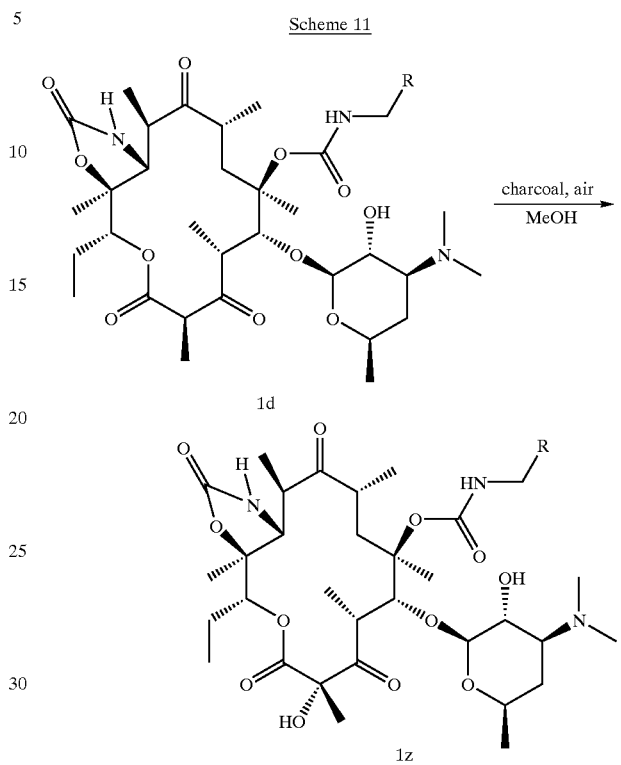

Scheme 10 illustrates a method for conversion of a secondary carbamate derivative (1j) to a tertiary carbamate derivative (1y), wherein R" is an independent member of the R group, and R and $R^4$ are as described above, by reaction with an aldehyde and a suitable reducing agent, typically triethylsilane, in the presence of an acid, typically trifluoroacetic acid, in an appropriate solvent, such as acetonitrile, methylene chloride, or toluene. Reaction times are typically 2 to 96 hours at a temperature ranging from 20° C. to 110° C. Alternative methods for effecting this conversion may also be contemplated, for example reaction of a suitably protected secondary carbamate precursor with an alkyl halide in the presence of a sufficiently strong base, such as sodium hydride, potassium hexamethyidisilazide, or LDA.

Scheme 11 illustrates the conversion of compounds 1d, wherein R is as previously defined, to compounds containing a 2-hydroxy substituent (1z). This transformation may be conducted by treatment of compound 1d with charcoal in the presence of air in a suitable solvent, such as methanol or ethanol. It will be apparent to one skilled in the art of organic synthesis that other methods may be employed to effect this conversion, including for example treatment of 1d with a base, such as potassium hexamethyldisilazide or LDA, and an oxidant, such as camphorsulfonyloxaziridine or MoOPh.

Scheme 12

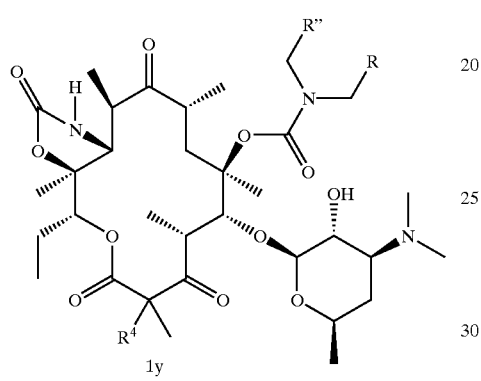

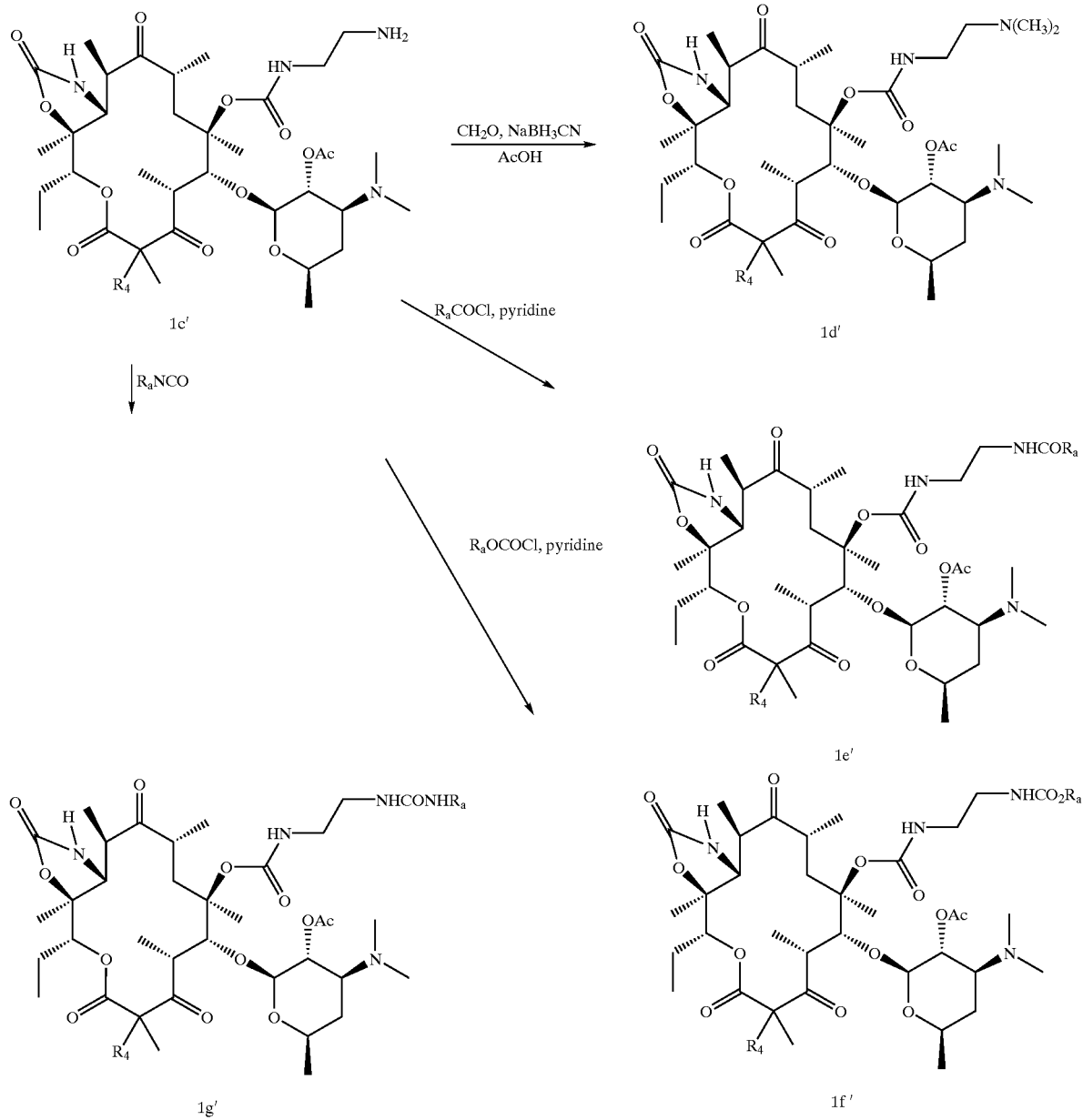

Scheme 12 illustrates the conversion of 1a' to compounds of the invention 1b', 1c', 1d', 1e', 1f', and 1g' with a nitrogen-containing substituent on the carbamate in the 6-position, wherein $R^4$ and $R_a$ are as described above. Reaction of 1a' with a protected aminoaldehyde derivative, such as N-(benzyloxycarbonyl)glycinal, in the presence of a suitable reducing agent, such as triethylsilane, and a suitable acid, such as trifluoroacetic acid affords the protected amine derivative (1b'). Typically this reaction is conducted in an appropriate solvent, such as acetonitrile, methylene chloride, or toluene, for 2 to 96 hours at a temperature ranging from 20° C. to 110° C. Deprotection of 1b' to afford the corresponding amine derivative (1c') can be readily effected by procedures known in the art, such as catalytic hydrogenation in the presence of a noble metal catalyst or catalytic transfer hydrogenation with palladium on carbon in the presence of cyclohexadiene or ammonium formate at a temperature ranging from 20° C. to 60° C. Typically these reactions are conducted in an inert solvent such as methanol or ethanol. Conversion of 1c' to several of the compounds of the invention (Scheme 12) can be conducted with techniques known in the art, such as reductive alkylation with formaldehyde in the presence of a suitable reducing agent, such as sodium cyanoborohydride, and an acid, such as acetic acid to afford the alkylated amine derivative (1d'). Alternatively, 1c' may be converted to the amide derivative (1e') by acylation with a suitably substituted acid chloride or acid anhydride in the presence of a base, such as pyridine, optionally in the presence of an acylation catalyst, such as DMAP. Amine derivative (1c') may also be converted to a carbamate (1f') by treatment with a suitably substituted chloroformate or pyrocarbonate derivative in the presence of pyridine. Finally, reaction of 1c' with a suitably substituted isocyanate in an inert solvent, such as tetrahydrofuran or methylene chloride, provides access to the correponding urea derivatives (1g'). Optional deprotection of the 2'-acetyl group of 1b', 1c', 1d', 1e', 1f', and 1g' is readily effected as described for the conversion of compound 1b to compound 1c (Scheme 2).

Scheme 13

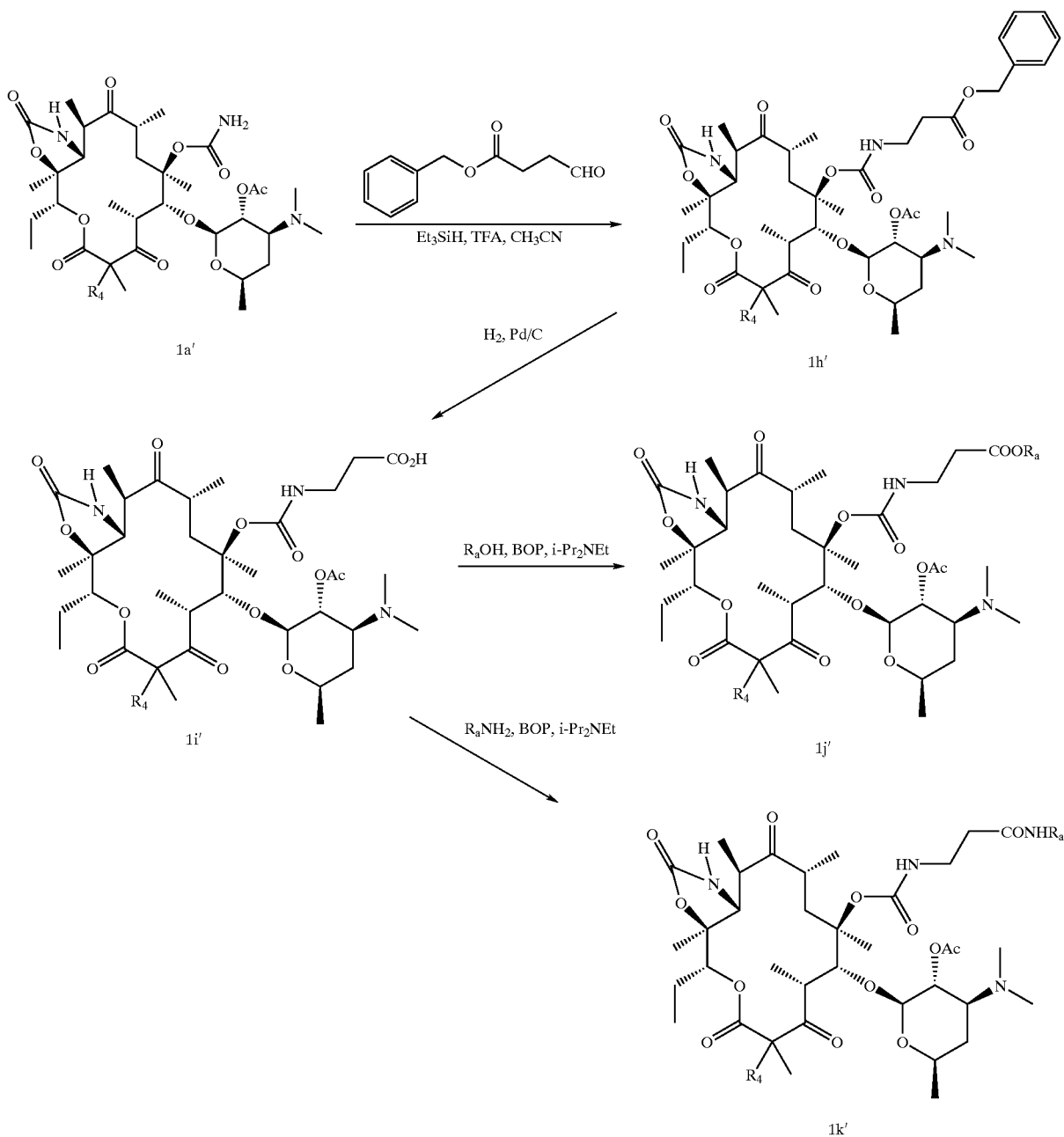

Scheme 13 illustrates the analogous procedure whereby 1a' is converted to compounds of the invention 1h', 1i', 1j', and 1k' with a carbonyl-containing substituent on the carbamate in the 6-position, wherein $R^4$ and $R_a$ are as described above. Reaction of 1a' with, for example, benzyl 4-oxobutanoic acid (Cannon, J. G. and Garst, J. E., *J. Org. Chem.* 1975, 40, 182) in the presence of a suitable reducing agent, such as triethylsilane, and a suitable acid, such as trifluoroacetic acid affords the benzyl ester derivative (1h'). Typically this reaction is conducted in an appropriate solvent, such as acetonitrile, methylene chloride, or toluene, for 2 to 96 hours at a temperature ranging from 20° C. to 110° C. Deprotection of 1h' to afford the corresponding acid derivative (1i') can be readily effected by procedures known in the art, such as catalytic hydrogenation in the presence palladium on carbon in an inert solvent such as methanol or ethanol. Conversion of 1i' to other compounds of the invention (Scheme 13) can be executed with techniques known in the art, such as reaction with a suitably substituted alcohol or amine in the presence of a coupling agent such as dicyclohexylcarbodiimide, BOP, or PyBOP, optionally in the presence of a base, such as diisopropylethylamine, and an acylation catalyst, such as DMAP or HOAt, to afford the corresponding ester derivative (1j') or amide derivative (1k'). Optional deprotection of the 2'-acetyl group of 1h', 1i', 1j', and 1k' is readily effected as described for the conversion of compound 1b to compound 1c (Scheme 2).

Scheme 14

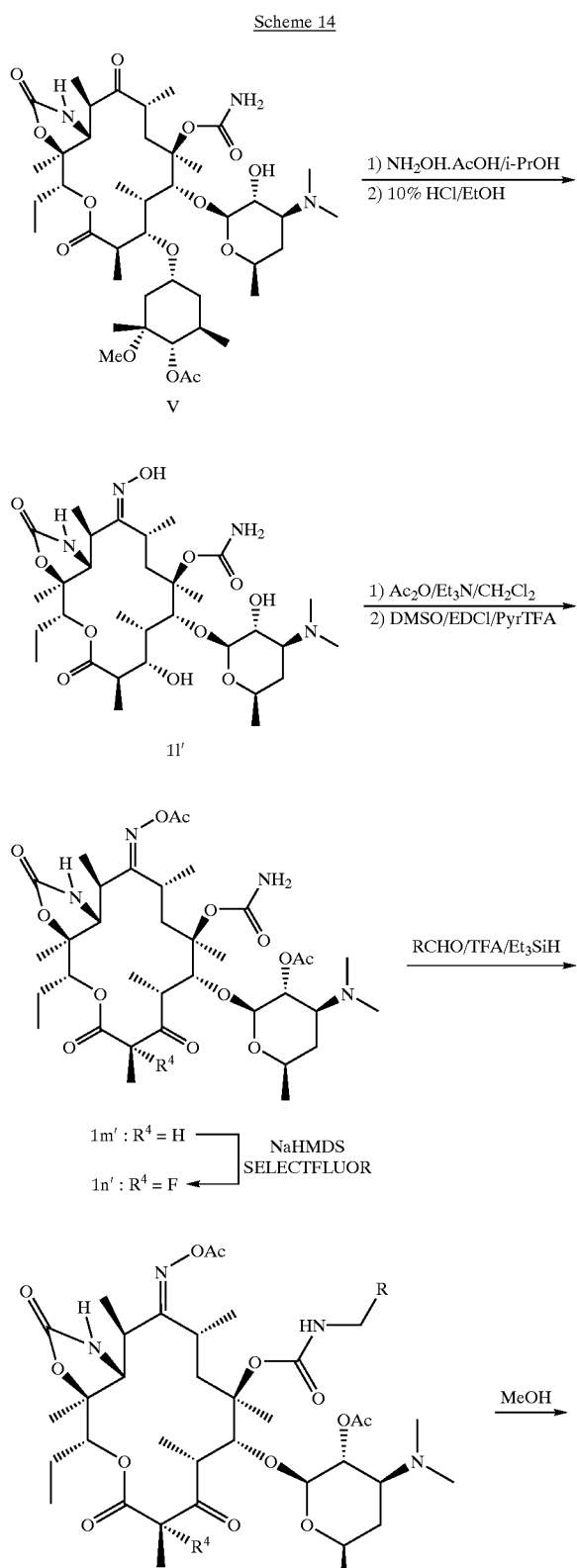

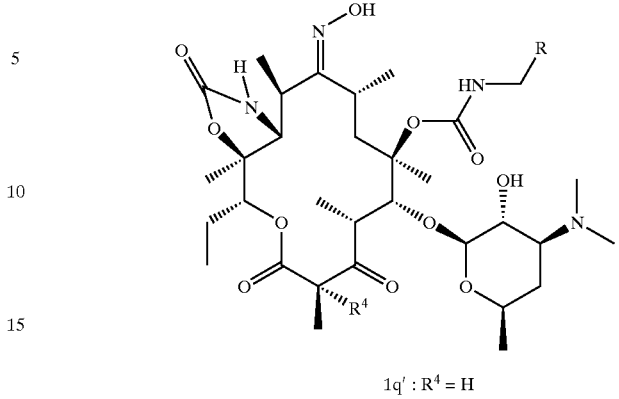

1q' : R⁴ = H
1r' : R⁴ = F

A method of synthesis of 9-oxime compounds of formulae 1l', 1m', 1n', 1o', 1p', 1q', and 1r' is illustrated in Scheme 14. Compound V is converted to compound 1l' by a two-step process. Treatment of compound V with hydroxylamine in the presence of an acid such as acetic acid or formic acid in an alcoholic solvent such as methanol, ethanol, or 2-propanol at a temperature from 50° C. to 100° C. results in oxime formation and partial hydrolysis of the cladinose sugar. Complete hydrolysis of the cladinose to provide compound 1l' is then effected by treatment with an acid, such as hydrochloric, sulfuric, chloroacetic, or trifluoroacetic, in the presence of alcohol and water. Preferred conditions for the oxime formation are the use of acetic acid in 2-propanol as solvent. Preferred conditions for cladinose removal are hydrochloric acid in aqueous ethanol. Protection of the 2'hydroxyl group and the oxime hydroxyl group followed by oxidation of the 3-hydroxyl provides compound 1m'. Protection of the 2' and oxime hydroxyl groups as their acetates can be carried out by treatment of 1l' with acetic anhydride in the presence of a tertiary amine base (such as triethylamine, diisopropylethylamine) or pyridine, and optionally an acylation catalyst, such as DMAP, in a suitable solvent such as methylene chloride, chloroform or THF at a temperature ranging from −20° C. to 37° C. for 2 to 48 hours. Oxidation of the 3-hydroxy group can be effected with DMSO and a carbodiimide, such as EDCI, in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Fluorination of compound 1m' with SELECTFLUOR and sodium hexamethyidisilazide in DMF provides compound 1n'. Compounds of formula 1o' and 1p' can be obtained by selective alkylation of the primary carbamate of 1m' and 1n', respectively, with a suitably substituted aldehyde in the presence of a reducing agent and acid. Alternatively, the corresponding acetal may be used in place of the suitably substituted aldehyde in this reaction. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the aldehyde or acetal. Removal of the 2'-acetyl and oxime acetyl groups of compounds of formulae 1o' and 1p' is readily accomplished by transesterification with methanol for 2–48 hours at a temperature ranging from −20° C. to 60° C. to yield compounds of formulae 1q' and 1r', respectively. Alternative methods for deprotection of the 2'-acetyl and oxime acetyl groups include hydrolysis in the presence of an alkali metal hydroxide or alkali metal carbonate, such as sodium hydroxide or potassium carbonate, or ammonolysis with ammonia in methanol.

Scheme 15

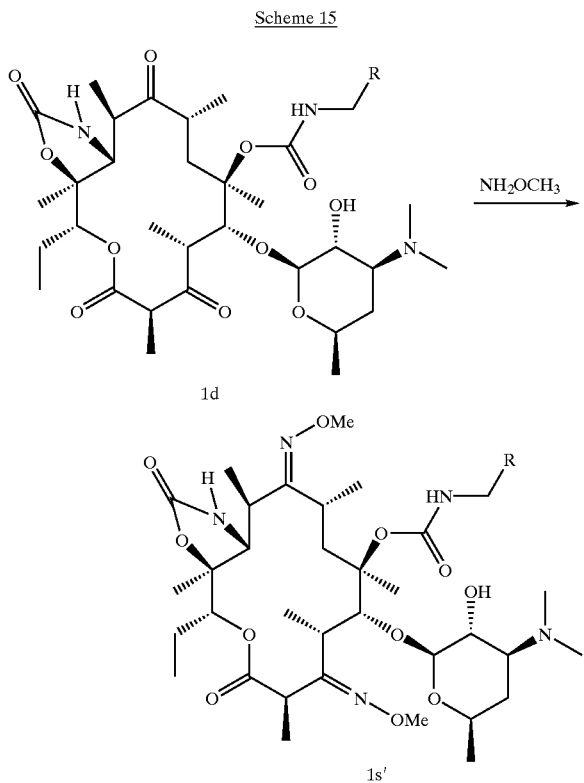

Scheme 15 illustrates a method of synthesis of 3,9-dioxime compounds. Treatment of a 3,9-diketo compound such as a compound of formula 1d with hydroxylamine or an alkoxylamine in an alcoholic or aqueous alcoholic solvent at a temperature from 50° C. to 120° C. for 2 to 72 hours provides compounds of formula 1s'. The hydroxylamine or alkoxylamine may optionally be used in the form of an acid addition salt. The reaction may also be performed in the presence of an acid catalyst such as acetic acid, formic acid, propionic acid, or hydrochloric acid.

Scheme 16

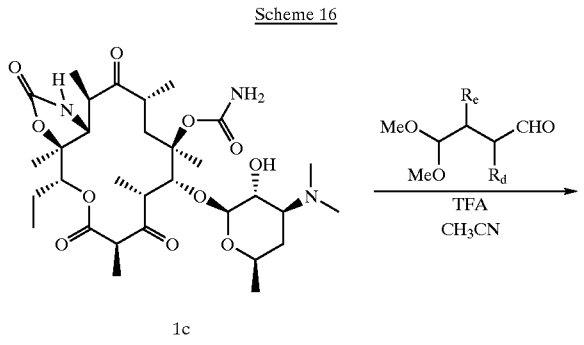

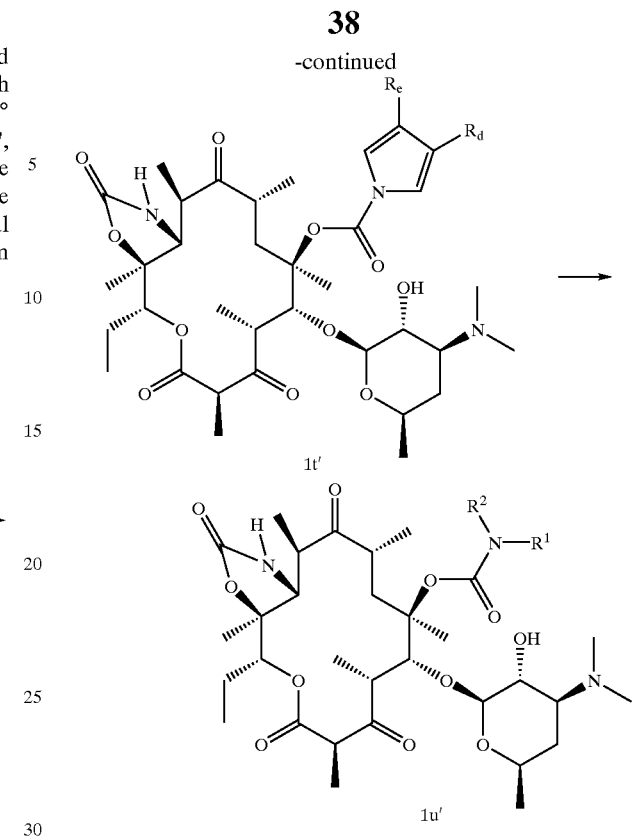

Scheme 16 illustrates an additional method for the preparation of compounds of the invention of Formula 1. The method is illustrated for the preparation of compounds of formula 1 u' from the compound of formula 1c via the compounds of formula 1t' as intermediates. Compounds of formula 1t' (where $R_d$ and $R_e$ are independently selected from the group consisting of hydrogen, CN, nitro, —C(O)$R_h$, —C(O)O$R_h$, —C(O)NR$_h$R$_i$, —SO$_2$R$_h$, optionally substituted C$_1$–C$_8$-alkyl, optionally substituted aryl, and optionally substituted heteroaryl, where $R_h$ and $R_i$ are independently selected from the group consisting of hydrogen, alkyl, aryl, and heteroaryl) can be obtained by reaction of 1c with a suitably substituted 1,4-dialdehyde or its equivalent in the presence of an acid. Equivalents of 1,4-dialdehydes include 2,5-dialkoxytetrahydrofurans, 1,4-dialdehyde monoacetals, and 1,4-dialdehyde diacetals. A preferred acid for effecting this transformation is trifluoroacetic acid in a suitable solvent, like acetonitrile, methylene chloride, or toluene at −20° C. to 100° C. Typically, the reaction is conducted for from 2–96 hours.

Preferred 1,4-dialdehydes or their equivalents include 2-formyl-4,4-dimethoxybutanenitrile, tetrahydro-2,5-dimethoxy-3-furancarboxaldehyde, tetrahydro-2,5-dimethoxy-3-furancarboxylic acid methyl ester, and tetrahydro-2,5-dimethoxy-3-furancarboxylic acid ethyl ester. Compounds of formula 1t' can be converted to compounds of formula 1u' by displacement of the pyrrole with primary amines or cyclic secondary amines in a suitable solvent, such as acetonitrile, dimethylformamide, dimethyl sulfoxide, or tetrahydrofuran, at a temperature ranging from −20° C. to 120° C. for 0.5 to 72 hours. Preferred substrates for this conversion are those in which the pyrrole is substituted with electron-withdrawing groups including, but not limited to, cyano, formyl, and alkoxycarbonyl. A particularly preferred substrate is compound 1t', where $R_d$=CN and $R_e$=H.

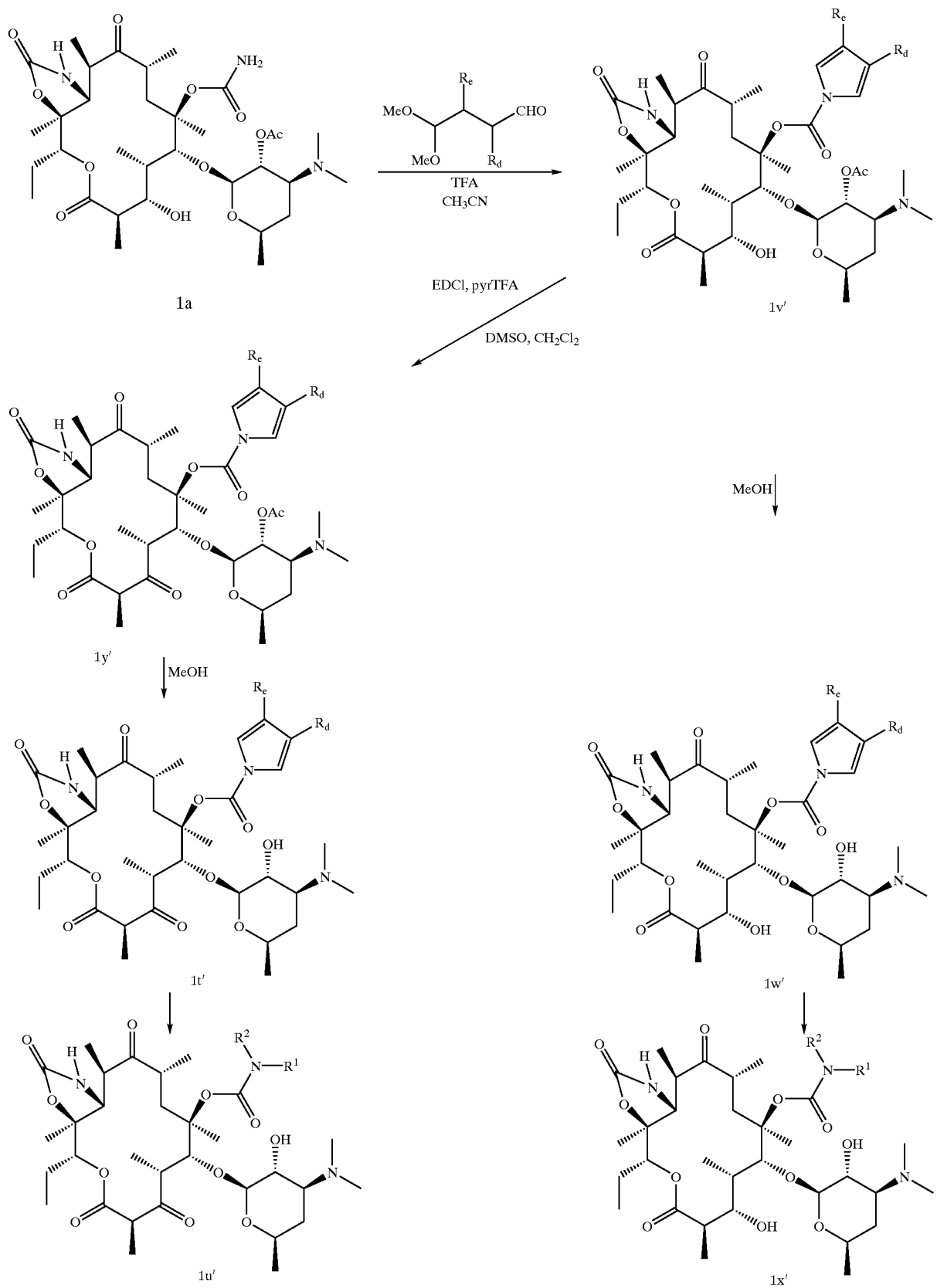
Scheme 17

It will be clear to one skilled in the art that the order of the steps in the synthetic sequence leading to compounds of the invention can be altered, provided that the functionality present in the molecule is compatible with the desired selective transformations. This is illustrated in Scheme 17. For example, compound 1a can be converted to compounds of formula 1v' under similar conditions as described above for the conversion of compound 1c to compound 1t' (Scheme 16). Removal of the 2'-acetyl group of compounds of formula 1v' as described for the conversion of compound 1b to compound 1c (Scheme 2) provides compounds of formula 1w'. Compounds of formula 1w' may then be converted to compounds of formula 1x' by treatment with primary amines or cyclic secondary amines as described for the conversion of compounds of formula 1t' to compounds of formula 1u' (Scheme 16). Alternatively, oxidation of the 3-hydroxyl of compounds of formula 1v' to the ketone of compounds of formula 1y' can be conducted as described for the analogous transformation of 1a to 1b in Scheme 2. Deprotection of the 2'-acetyl group of compounds of formula 1y' is readily effected as described for the conversion of compound 1b to compound 1c (Scheme 2) to provide the compounds of formula 1t'. Compounds of formula 1t' may then be converted to compounds of formula 1u' as described above in Scheme 16.

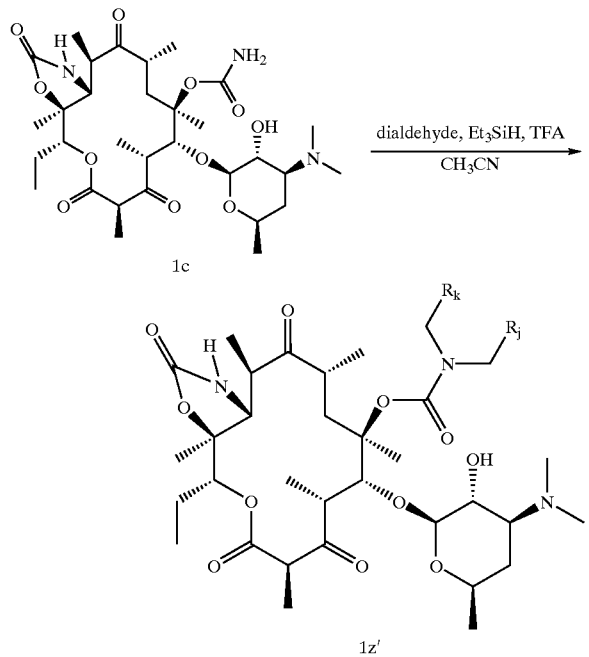

Scheme 18

Scheme 18 illustrates a method for the synthesis of compounds of formula 1z' in which $R_j$ and $R_k$ taken together with the atoms to which they are attached form a nitrogen-containing heterocycle. Treatment of 1c with a dialdehyde or dialdehyde equivalent in the presence of a reducing agent and acid provides compounds of formula 1z'. Dialdehyde equivalents include dialdehyde monoacetals, dialdehyde diacetals, 2,5-dialkoxytetrahydrofurans, 2,6-dialkoxytetrahydropyrans, and 2-alkoxy-3,4-dihydro-2H-pyrans. Preferred reagents for effecting this transformation are triethylsilane and trifluoroacetic acid in a suitable solvent, like acetonitrile, methylene chloride, or toluene at −20° C. to 100° C. Typically, the reaction is conducted for from 2–96 hours depending on the reactivity of the dialdehyde or dialdehyde equivalent. It will be clear to one skilled in the art that the reaction illustrated in Scheme 18 can also be conducted at different stages in the synthetic sequence to access compounds analogous to compounds of formula 1z'.

When the aldehydes or acetals used in the preparation of compounds 1d, 1e, 1i, 1m, 1p, and 1y are not commercially available, they can be obtained by conventional synthetic procedures, in accordance with literature precedent, from readily accessible starting materials using standard reagents and reaction conditions. Exemplary syntheses of several of the aldehydes used in the preparation of 1d, 1e, 1i, 1m, 1p, and 1y are presented hereinafter as reference examples.

When the dialdehydes or dialdehyde equivalents used in the preparation of compounds 1t', 1v', and 1z' are not commercially available, they can be obtained by conventional synthetic procedures, in accordance with literature precedent, from readily accessible starting materials using standard reagents and reaction conditions. Exemplary syntheses of several of the dialdehydes or dialdehyde equivalents used in the preparation of compounds 1t', 1v', and 1z' are presented hereinafter as reference examples.

When the amines used in the preparation of compounds 1u' and 1x' are not commercially available, they can be obtained by conventional synthetic procedures, in accordance with literature precedent, from readily accessible starting materials using standard reagents and reaction conditions. Exemplary syntheses of several of the amines used in the preparation of compounds 1u' and 1x' are presented hereinafter as reference examples.

Compounds of the invention wherein $R^3$ is a group other than H may be prepared by methods described in WO00/75156, which is hereby incorporated by reference.

Compounds of the invention wherein $R^5$ is a hydroxy protecting group other than acyl may be prepared by methods analogous to those shown in the above schemes with appropriate reagents that are either commercially available or may be made by known methods.

Compounds of the invention wherein $R^6$ is a group other than ethyl may be prepared beginning with modified erythromycin derivatives as starting materials as described in various publications including, but not limited to, WO99/35157, WO00/62783, WO00/63224, and WO00/63225, which are all incorporated by reference herein.

These compounds have antimicrobial activity against susceptible and drug resistant Gram positive and Gram negative bacteria. In particular, they are useful as broad spectrum antibacterial agents for the treatment of bacterial infections in humans and animals. These compounds are particularly activity against S. aureus, S. epidermidis, S. pneumoniae, S. pyogenes, Enterococci, Moraxelia catarrhalis and H. influenzae. These compounds are particularly useful in the treatment of community-acquired pneumonia, upper and lower respiratory tract infections, skin and soft tissue infections, meningitis, hospital-acquired lung infections, and bone and joint infections.

Minimal inhibitory concentration (MIC) has been an indicator of in vitro antibacterial activity widely used in the art. The in vitro antimicrobial activity of the compounds was determined by the microdilution broth method following the test method from the National Committee for Clinical Laboratory Standards (NCCLS). This method is described in the NCCLS Document M7-A4, Vol. 17, No. 2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5\times10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities depending on the organism tested.

Table 1 below sets forth the biological activity (MIC, μg/mL) of some compounds of the present invention.

TABLE 1

MIC Values (μg/mL) of Some Compounds of Formula I
(A: *E. coli* OC2605;
B: *S. aureus* ATCC29213; C: *E. faecalis* ATCC29212;
D: *S. pneumoniae* ATCC49619; E: *H. influenzae* ATCC49247)

| | MIC (μg/mL) | | | | |
|---|---|---|---|---|---|
| No. | A | B | C | D | E |
| 1 | >16 | 4 | 0.12 | 0.03 | ND |
| 2 | 16 | 1 | 0.25 | 0.06 | 2 |
| 3 | >16 | 4 | 1 | 0.12 | 8 |
| 4 | >16 | 0.25 | 0.12 | 0.03 | 1 |
| 5 | >16 | 0.5 | 0.25 | 0.03 | ND |
| 6 | >16 | 4 | 1 | 0.12 | ND |
| 7 | 16 | 0.5 | 0.06 | 0.03 | 4 |
| 8 | 16 | 1 | 0.12 | 0.03 | 4 |
| 9 | >16 | 1 | 0.25 | 0.03 | 16 |
| 10 | 16 | 1 | 0.25 | 0.03 | 4 |
| 11 | >16 | 4 | 2 | 0.5 | >16 |
| 12 | 16 | 1 | 0.12 | 0.06 | 4 |
| 13 | >16 | 1 | 0.25 | 0.06 | 8 |
| 14 | >16 | 8 | 0.5 | 0.12 | >16 |
| 15 | 4 | 0.12 | 0.06 | 0.03 | 2 |
| 16 | 8 | 0.5 | 0.12 | 0.03 | 4 |
| 17 | 16 | 0.5 | 0.25 | 0.06 | 4 |
| 18 | 16 | 0.25 | 0.06 | 0.03 | 4 |
| 19 | 16 | 0.12 | 0.12 | 0.03 | 4 |
| 20 | 16 | 0.12 | 0.06 | 0.03 | 4 |
| 21 | >16 | 0.5 | 0.25 | 0.06 | 4 |
| 22 | 8 | 0.25 | 0.06 | 0.03 | 2 |
| 23 | 16 | 0.25 | 0.12 | 0.06 | 2 |
| 24 | 16 | 1 | 0.12 | 0.06 | 2 |
| 25 | 8 | 0.25 | 0.06 | 0.03 | 4 |
| 26 | >16 | 0.5 | 0.12 | 0.03 | 2 |
| 27 | 16 | 0.25 | 0.12 | 0.06 | 4 |
| 28 | 16 | 0.25 | 0.06 | 0.03 | 4 |
| 29 | 16 | 0.5 | 0.06 | 0.03 | 2 |
| 30 | 16 | 0.5 | 0.12 | 0.03 | 2 |
| 31 | 16 | 0.25 | 0.06 | 0.03 | 2 |
| 32 | 16 | 0.12 | 0.06 | 0.06 | ND |
| 33 | 8 | 0.12 | 0.06 | ≦0.015 | ND |
| 34 | 8 | 0.12 | 0.06 | ≦0.015 | ND |
| 35 | 8 | 0.12 | 0.03 | ≦0.015 | ND |
| 36 | 8 | 0.12 | 0.03 | ≦0.015 | ND |
| 37 | 16 | 0.5 | 0.12 | 0.03 | ND |
| 38 | 8 | 0.12 | 0.03 | ≦0.015 | ND |
| 39 | >16 | 1 | 0.12 | 0.06 | 1 |
| 40 | 16 | 1 | 0.5 | 0.12 | ND |
| 41 | 16 | 0.25 | 0.12 | 0.03 | 1 |
| 42 | 16 | 0.5 | 0.12 | 0.12 | 1 |
| 43 | >16 | 0.25 | 0.12 | 0.03 | 2 |
| 44 | >16 | 0.25 | 0.12 | 0.12 | 2 |
| 45 | >16 | 1 | 0.5 | 0.25 | 4 |
| 46 | 16 | 0.25 | 0.06 | ND | 2 |
| 47 | 16 | 0.25 | 0.06 | ND | 1 |
| 48 | >16 | 0.5 | 0.12 | ND | 4 |
| 49 | 16 | 0.25 | 0.06 | 0.06 | 2 |
| 50 | 16 | 0.25 | 0.06 | ≦0.015 | 2 |
| 51 | >16 | 0.5 | 0.12 | 0.06 | 8 |
| 52 | 8 | 0.25 | 0.12 | 0.03 | 2 |
| 53 | 16 | 0.25 | 0.12 | 0.03 | 4 |
| 54 | >16 | 1 | 0.5 | 0.12 | 2 |
| 55 | 16 | 0.5 | 0.12 | 0.03 | 4 |
| 56 | 8 | 0.25 | 0.06 | ≦0.015 | 2 |
| 57 | 16 | 0.25 | 0.12 | 0.03 | 2 |
| 58 | >16 | 0.25 | 0.12 | 0.06 | 4 |
| 59 | >16 | 0.5 | ≦0.25 | 0.03 | 4 |
| 60 | >16 | 1 | 0.5 | 0.25 | 8 |
| 61 | 16 | 0.5 | 0.06 | 0.03 | 2 |
| 62 | >16 | 0.25 | 0.12 | 0.06 | 4 |
| 63 | >16 | 0.25 | 0.12 | 0.06 | 2 |
| 64 | >16 | 1 | 0.12 | 0.03 | 4 |
| 65 | >16 | 2 | 0.25 | 0.06 | 8 |
| 66 | >16 | 0.5 | 0.12 | 0.06 | 4 |
| 67 | >16 | 0.25 | 0.25 | 0.06 | 4 |
| 68 | >16 | 0.25 | 0.12 | 0.03 | 4 |
| 69 | >16 | 0.5 | 0.12 | 0.03 | 8 |
| 70 | 16 | 0.25 | 0.12 | 0.03 | 4 |
| 71 | >16 | 0.25 | 0.12 | 0.06 | 4 |
| 72 | 8 | 0.25 | 0.06 | ≦0.015 | 2 |
| 73 | 16 | 0.5 | 0.06 | 0.03 | 2 |
| 74 | 16 | 0.06 | 0.06 | ≦0.015 | 1 |
| 75 | >16 | 0.25 | 0.12 | 0.03 | 4 |
| 76 | 16 | 0.25 | 0.06 | ≦0.015 | 2 |
| 77 | 16 | 0.12 | 0.12 | 0.03 | 4 |
| 78 | >16 | 0.25 | 0.06 | 0.03 | 4 |
| 79 | 8 | 0.25 | 0.06 | 0.03 | 2 |
| 80 | >16 | 0.12 | 0.06 | 0.03 | 4 |
| 81 | >16 | 2 | 0.12 | 0.06 | 8 |
| 82 | >16 | 0.25 | 0.06 | 0.03 | 4 |
| 83 | >16 | 2 | 0.25 | 0.06 | 8 |
| 84 | >16 | 0.25 | 0.12 | 0.06 | 4 |
| 85 | >16 | 1 | 0.25 | 0.12 | >16 |
| 86 | >16 | 0.5 | 0.12 | 0.06 | 8 |
| 87 | 16 | 0.25 | 0.06 | 0.03 | 4 |
| 88 | 16 | 0.25 | 0.06 | 0.06 | 8 |
| 89 | 16 | 0.5 | 0.25 | 0.06 | 8 |
| 90 | 8 | 0.25 | 0.06 | 0.03 | 4 |
| 91 | 16 | 0.25 | 0.12 | 0.06 | 4 |
| 92 | 16 | 0.25 | 0.12 | 0.03 | 2 |
| 93 | 16 | 0.5 | 0.06 | ≦0.015 | 1 |
| 94 | >16 | 0.25 | 0.12 | 0.06 | 2 |
| 95 | >16 | 1 | 0.25 | ND | 2 |
| 96 | 4 | 0.25 | 0.12 | 0.03 | 1 |
| 97 | 16 | 0.5 | 0.06 | 0.03 | 2 |
| 98 | >16 | 0.5 | 0.25 | 0.03 | 4 |
| 99 | 8 | 0.5 | 0.12 | ND | 1 |
| 100 | 16 | 0.5 | 0.12 | ND | 2 |
| 101 | 8 | 0.25 | 0.12 | 0.03 | 2 |
| 107 | >16 | 0.25 | 0.12 | 0.06 | 4 |
| 108 | >16 | 0.5 | 0.25 | 0.06 | 4 |
| 109 | >16 | 8 | 2 | 0.25 | 16 |
| 110 | >16 | 16 | 8 | 1 | 16 |
| 111 | >16 | 1 | 0.5 | 0.06 | 4 |
| 112 | >16 | 16 | 2 | 0.5 | 16 |
| 113 | >16 | 4 | 1 | 0.06 | 8 |
| 114 | >16 | 2 | 0.25 | 0.06 | 4 |
| 115 | >16 | 2 | 0.5 | 0.06 | 16 |
| 116 | >16 | 2 | 1 | 0.12 | 8 |
| 117 | >16 | 2 | 0.5 | 0.06 | >16 |
| 118 | >16 | 8 | 1 | 0.12 | 16 |
| 119 | >16 | 4 | 0.25 | 0.06 | 8 |
| 123 | 16 | 0.25 | 0.12 | 0.03 | 4 |
| 124 | 16 | 0.25 | 0.12 | 0.03 | 4 |
| 125 | 16 | 0.5 | 0.25 | 0.06 | 2 |
| 126 | 16 | 0.5 | 0.25 | 0.06 | 4 |

TABLE 1-continued

MIC Values (µg/mL) of Some Compounds of Formula I
(A: *E. coli* OC2605;
B: *S. aureus* ATCC29213; C: *E. faecalis* ATCC29212;
D: *S. pneumoniae* ATCC49619; E: *H. influenzae* ATCC49247)

| | MIC (µg/mL) | | | | |
|---|---|---|---|---|---|
| No. | A | B | C | D | E |
| 127 | 8 | 0.25 | 0.12 | 0.03 | 2 |
| 128 | >16 | 4 | 2 | 0.25 | 8 |
| 129 | 8 | 0.25 | 0.12 | 0.03 | 1 |
| 130 | 8 | 0.25 | 0.12 | ≦0.015 | 0.5 |
| 131 | 8 | 0.25 | 0.12 | 0.03 | 0.5 |
| 132 | 16 | 0.5 | 0.25 | 0.03 | 1 |
| 133 | 16 | 0.25 | 0.25 | 0.03 | 2 |
| 134 | >16 | 2 | 1 | 0.12 | >16 |
| 135 | >16 | 4 | 2 | 0.5 | >16 |
| 136 | >16 | ND | 4 | 2 | >16 |
| 137 | >16 | 4 | 1 | 0.25 | 8 |
| 138 | >16 | 16 | 2 | 0.5 | 8 |

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, which may be given in divided doses two to four times a day, or in sustained release form. For most large mammals the total daily dosage is from about 0.07 g to 7.0 g, preferably from about 100 mg to 2000 mg. Dosage forms suitable for internal use comprise from about 100 mg to 1200 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Compound 6 (Formula 1': $R_1$ is H, $R_2$ is H, $R_3$ is H, $R_4$ is H)

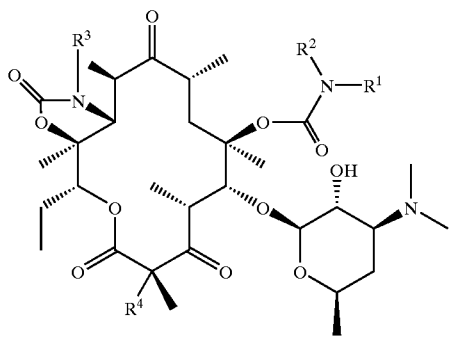

Formula 1'

Step A

Triethylamine (42.0 mL, 301 mmol), DMAP (0.6 g, 4.9 mmol), and acetic anhydride (28.5 mL, 302 mmol) were added to a 0° C. suspension of erythromycin (36.7 g, 50 mmol) in dichloromethane (250 mL). The mixture was allowed to warm to room temperature and stir for 18 h. Methanol (10 mL) was added and stirring was continued for 5 min. The mixture was diluted with ether (750 mL), washed with sat. aq. NaHCO$_3$, water, and brine (500 mL each), dried (MgSO$_4$), and concentrated to provide the title compound as a colorless foam. The material was used in the next step without further purification. MS 860 (M+H)$^+$.

Step B

Sodium hexamethyldisilazide (1.0M in THF, 60.0 mL, 60.00 mmol) was added over 25 min to a 0° C. solution of the compound from step A (50.0 mmol) in THF (500 mL). After 2 h at 0° C., the mixture was diluted with water (250 mL) and brine (250 mL) and extracted with ethyl acetate (3×250 mL). The combined organic layers were dried (MgSO$_4$) and concentrated. The material was used in the next step without further purification. If desired, pure material could be obtained by chromatography (SiO$_2$, 95:5:0.2 dichloromethane/methanol/conc. NH$_4$OH). MS 800 (M+H)$^+$.

Step C

Trichloroacetylisocyanate (18.0 mL, 151 mmol) was added over 20 min to a 0° C. solution of the compound from step B (50 mmol) in dichloromethane (350 mL). After 3 h at 0° C., the reaction was quenched by the addition of methanol (30 mL) and concentrated. The residue was dissolved in a mixture of methanol (450 mL), water (45 mL), and triethylamine (18 mL), heated to reflux for 2 h, and concentrated. The residue was dissolved in ethyl acetate (500 mL), washed with sat. aq. NaHCO$_3$ (250 mL) and brine (250 mL), dried (MgSO$_4$), and concentrated. The resulting mixture of C-10 epimers was dissolved in THF (500 mL) at 0° C. and potassium t-butoxide (1.0 M in THF, 60.0 mL, 60.0 mmol) was added over 15 min. The resulting mixture was stirred at 0° C. to 15° C. for 6 h. Sat. aq. NaHCO$_3$ (250 mL) was added, the bulk of the THF was removed in vacuo, and the resulting solution was extracted with ethyl acetate (3×250 mL). The combined organic extracts were washed with brine (250 mL), dried (MgSO$_4$), and concentrated. The material was used in the next step without further purification. If desired, pure material could be obtained by chromatography (SiO$_2$, 95:5:0.2 dichloromethane/methanol/conc. NH$_4$OH). MS 844 (M+H)$^+$.

Step D

A solution of the compound from step C (50 mmol), triethylamine (13.0 mL, 93.3 mmol), and acetic anhydride (8.8 mL, 93.3 mmol) in dichloromethane (250 mL) was stirred at room temperature for 20 h. The solution was washed with sat. aq. NaHCO$_3$ (2×250 mL) and brine (250 mL), dried (MgSO$_4$), and concentrated. The material was used in the next step without further purification. MS 886 (M+H)$^+$.

Step E

The compound from step D (50 mmol) was dissolved in 1.2 N HCl (400 mL) and ethanol (160 mL) and stirred at room temperature for 20 h. The mixture was cooled to 0° C., made basic with 10% NaOH, and extracted with ethyl acetate (3×300 mL). The combined organic layers were washed with water (300 mL) and brine (300 mL), dried (MgSO$_4$), and concentrated. Purification by chromatography (SiO$_2$, 94:6:0.5 dichloromethane/methanol/conc. NH$_4$OH) yields 10.4 g (30% based on erythromycin) of the title compound as a colorless solid. MS 686 (M+H)$^+$.

Step F

EDCI (3.92 g, 20.45 mmol) was added to a solution of the compound from step E (2.00 g, 2.92 mmol) and dimethyl sulfoxide (3.70 mL, 52.14 mmol) in dichloromethane (10 ml) at 0° C. A solution of pyridinium trifluoroacetate (3.94 g, 20.40 mmol) in dichloromethane (10 mL) was added over 10 min and the resulting solution was stirred at 0° C. for 2 h before being quenched with water (2 mL). After 5 min, the mixture was diluted with dichloromethane (50 mL), washed with water (50 mL) and brine (50 mL), dried (MgSO$_4$), and concentrated. The material was used in the next step without further purification. If desired, pure material could be obtained by chromatography (SiO$_2$, 96:4:0.2 dichloromethane/methanol/conc. NH$_4$OH). MS 684 (M+H)$^+$.

Step G

The crude product from step F was allowed to stand in methanol (20 mL) for 24 h and then concentrated. Purification by chromatography (SiO$_2$, 94:6:0.2 dichloromethane/methanol/conc. NH$_4$OH) yields 1.39 g (74%) of the title compound as a colorless solid. MS 642 (M+H)$^+$.

EXAMPLE 2

Compound 106 (Formula 1': $R_1$ is H, $R_2$ is H, $R_3$ is H, $R_4$ is F)

Sodium hexamethyldisilazide (1.0M in THF, 1.14 mL, 1.14 mmol) was added to a solution of the compound from Example 1, step F (520 mg, 0.76 mmol) in DMF (8 mL) at −60° C. After 30 min at −60° C., SELECTFLUOR™ (324 mg, 0.91 mmol) was added. The resulting mixture was stirred for 10 min at −60° C., diluted with ethyl acetate, washed with water and brine, dried (MgSO$_4$), and concentrated. This material was allowed to stand in methanol for 24 h and then concentrated. Purification by chromatography (SiO$_2$, 3–5% methanol in dichloromethane+0.1% conc. NH$_4$OH) followed by a second chromatography (SiO$_2$, acetone) yielded 201 mg (40%) of the title compound. MS 660 (M+H)$^+$.

EXAMPLE 3

2'-Acetate of Compound 106

Potassium t-butoxide (1.0 M in THF, 0.23 mL, 0.23 mmol) was added dropwise to a −78° C. solution of the compound from Example 1, step f (120 mg, 0.18 mmol) in THF (3 mL). After 30 min at −78° C., N-fluoro benzensulfonimide (72 mg, 0.23 mmol) was added and the mixture was stirred at −78° C. for 4 h. Sat. aq. NaHCO$_3$ was added, the mixture was stirred for 10 min, and then extracted with ethyl acetate. The organic extracts were washed with brine, dried (MgSO$_4$), and concentrated. Purification by chromatography (SiO$_2$, 95:5:0.1 dichloromethane/methanol/conc. NH$_4$OH) yielded 36 mg (29%) of the title compound. MS 702 (M+H)$^+$.

EXAMPLE 4

Compound 1 (Formula 1': R$_1$ is phenylmethyl, R$_2$ is H, R$_3$ is H, R$_4$ is H)

Step A

A solution of the compound from Example 1, step E (100 mg, 0.15 mmol), triethylsilane (116 μL, 0.73 mmol), trifluoroacetic acid (54 μL, 0.70 mmol), and benzaldehyde (74 μL, 0.73 mmol) in CH$_3$CN (0.5 mL) was stirred at room temperature for 18 h and then heated to 60° C. for 22 h. The reaction mixture was diluted with ethyl acetate (15 mL), washed with sat. aq. NaHCO$_3$ (5 mL) and brine (5 mL), dried (Na$_2$SO$_4$), and concentrated. Purification by chromatography (SiO$_2$, 95:5:0.2 dichloromethane/methanol/conc. NH$_4$OH) yielded 72 mg (64%) of the title compound. MS 776 (M+H)$^+$.

Step B

The Dess-Martin reagent (75 mg, 0.18 mmol) was added to a solution of the product from step A (68 mg, 0.088 mmol) in dichloromethane (0.5 mL) and the mixture was stirred at room temperature for 8 h. The solvent was evaporated and the residue was diluted with ethyl acetate (10 mL), washed with 1:1 sat aq. NaHCO$_3$/10% Na$_2$S$_2$O$_3$ (10 mL), water (5 mL), and brine (5 mL), dried (Na$_2$SO$_4$), and concentrated. The material obtained was stirred in methanol (3 mL) for 24 h and then concentrated. Purification by chromatography (SiO$_2$, 96:4:0.2 dichloromethane/methanol/conc. NH$_4$OH) yielded 31 mg (48%) of the title compound. MS 732 (M+H)$^+$.

EXAMPLE 5

Compound 2 (Formula 1': R$_1$ is 3-phenylpropyl, R$_2$ is H, R$_3$ is H, R$_4$ is H)

Step A

A solution of the compound from example 1, step E (250 mg, 0.37 mmol), triethylsilane (290 μL, 1.82 mmol), trifluoroacetic acid (135 μL, 1.75 mmol), and hydrocinnamaldehyde (240 μL, 1.82 mmol) in CH$_3$CN (1.5 mL) was heated to 60° C. for 3 h. The reaction mixture was diluted with ethyl acetate (30 mL), washed with sat. aq. NaHCO$_3$ (15 mL), 10% aq. NaHSO$_3$ (15 mL), and brine (15 mL), dried (MgSO$_4$), and concentrated. Purification by chromatography (SiO$_2$, 95:5:0.1 dichloromethane/methanol/conc. NH$_4$OH) yielded 212 mg (74%) of the title compound. MS 804 (M+H)$^+$.

Step B

The Dess-Martin reagent (169 mg, 0.40 mmol) was added to a solution of the product from step A (160 mg, 0.20 mmol) in dichloromethane (2 mL) and the mixture was stirred at room temperature for 24 h. The solvent was evaporated and the residue was diluted with ethyl acetate (30 mL), washed with 1:1 sat aq. NaHCO$_3$/10% Na$_2$S$_2$O$_3$ (15 mL), water (15 mL), and brine (15 mL), dried (MgSO$_4$), and concentrated. The material obtained was stirred in methanol (6 mL) for 24 h and then concentrated. Purification by chromatography (SiO$_2$, 96:4:0.1 dichloromethane/methanol/conc. NH$_4$OH) yielded 52 mg (34%) of the title compound. MS 760 (M+H)$^+$.

EXAMPLE 6

Compound 3 (Formula 1': R$_1$ is 2-phenylethyl, R$_2$ is H, R$_3$ is H, R$_4$ is H)

Step A

A solution of the compound from example 1, step E (100 mg, 0.15 mmol), triethylsilane (116 μL, 0.73 mmol), trifluoroacetic acid (54 μL, 0.70 mmol), and phenylacetaldehyde (74 μL, 0.73 mmol) in CH$_3$CN (0.5 mL) was stirred at room temperature for 18 h. The reaction mixture was diluted with ethyl acetate (15 mL), washed with sat. aq. NaHCO$_3$ (5 mL) and brine (5 mL), dried (Na$_2$SO$_4$), and concentrated. Purification by chromatography (SiO$_2$, 95:5:0.2 dichloromethane/methanol/conc. NH$_4$OH) yielded 93 mg (81%) of the title compound. MS 790 (M+H)$^+$.

Step B

The Dess-Martin reagent (150 mg, 0.36 mmol) was added to a solution of the product from step a (93 mg, 0.12 mmol) in dichloromethane (2 mL) and the mixture was stirred at room temperature for 24 h. The solvent was evaporated and the residue was diluted with ethyl acetate (30 mL), washed with 1:1 sat aq. NaHCO$_3$/10% Na$_2$S$_2$O$_3$ (15 mL), water (15 mL), and brine (15 mL), dried (MgSO$_4$), and concentrated. The material obtained was stirred in methanol (6 mL) for 24 h and then concentrated. Purification by chromatography (SiO$_2$, 96:4:0.1 dichloromethane/methanol/conc. NH$_4$OH) yielded 42 mg (48%) of the title compound. MS 746 (M+H)$^+$.

EXAMPLE 7

Compound 4 (Formula 1': R$_1$ is (2E)-3-phenyl-2-propenyl, R$_2$ is H, R$_3$ is H, R$_4$ is H)

A solution of the compound from example 1, step F (90 mg, 0.13 mmol), triethylsilane (105 μL, 0.66 mmol), trifluoroacetic acid (50 μL, 0.65 mmol), and cinnamaldehyde (85 μL, 0.67 mmol) in CH$_3$CN (0.5 mL) was stirred at room temperature for 5 days. The reaction mixture was diluted with ethyl acetate (15 mL), washed with sat. aq. NaHCO$_3$ (10 mL) and brine (10 mL), dried (Na$_2$SO$_4$), and concentrated. The product was allowed to stand in methanol (3 mL) for 24 h and concentrated. Purification by chromatography (SiO$_2$, 97:3:0.2 dichloromethane/methanol/conc. NH$_4$OH) yielded 50 mg (50%) of the title compound as a colorless solid. MS 758 (M+H)$^+$.

EXAMPLE 8

Compound 5 (Formula 1': R$_1$ is (4-bromophenyl)methyl, R$_2$ is H, R$_3$ is H, R$_4$ is H)

A solution of the compound from example 1, step G (500 mg, 0.78 mmol), triethylsilane (0.63 mL, 3.94 mmol), trifluoroacetic acid (0.30 mL, 3.89 mmol), and 4-bromobenzaldehyde (720 mg, 3.89 mmol) in CH$_3$CN (2.0 mL) was heated to 60° C. for 48 h. The reaction mixture was diluted with ethyl acetate (30 mL), washed with sat. aq. NaHCO$_3$ (30 mL) and brine (30 mL), dried (Na$_2$SO$_4$), and concentrated. Purification by chromatography (SiO$_2$, 94:6:0.5 dichloromethane/methanol/conc. NH$_4$OH) yielded 500 mg (79%) of the title compound as a colorless solid. MS 810 (M+H)$^+$.

EXAMPLE 9

Compound 7 (Formula 1': R$_1$ is [4-(1H-pyrazol-1-yl)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and 4-(1H-pyrazol-1-yl)-benzaldehyde (134 mg, 0.78 mmol, prepared as described in *J. Med Chem.* 1998, 41, 2390) in $CH_3CN$ (1.0 mL) was heated to 62° C. for 3 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.2 dichloromethane/methanol/conc. $NH_4OH$) yielded 102 mg (82%) of the title compound. MS 798 $(M+H)^+$.

EXAMPLE 10

Compound 8 (Formula 1': $R_1$ is [4-(1H-imidazol-1-yl)phenyl]methyl, $R_2$ is H, $R_3$ is H, $R_4$ is H)

A solution of the compound from example 1, step G (80 mg, 0.12 mmol), triethylsilane (200 μL, 1.25 mmol), trifluoroacetic acid (96 μL, 1.25 mmol), and 4-(1H-imidazol-1-yl)-benzaldehyde (108 mg, 0.62 mmol, prepared as described in *J. Med Chem.* 1998, 41, 2390) in $CH_3CN$ (1.0 mL) was heated to 65° C. for 4 days. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.2 dichloromethane/methanol/conc. $NH_4OH$) yielded 8.3 mg (8%) of the title compound. MS 798 $(M+H)^+$.

EXAMPLE 11

Compound 9 (Formula 1': $R_1$ is 4-phenylbutyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (50 μL, 0.65 mmol), and the compound from Reference Example 1 (93 mg, 0.62 mmol) in $CH_3CN$ (1.0 mL) was heated to 60° C. for 2 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 48 mg (50%) of the title compound. MS 774 $(M+H)^+$.

EXAMPLE 12

Compound 10 (Formula 1': $R_1$ is [4-(1H-1,2,4-triazol-1-yl)phenyl]methyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (48 μL, 0.62 mmol), and 4-(1H-1,2,4-triazol-1-yl)-benzaldehyde (108 mg, 0.62 mmol, prepared as described in *J. Med Chem.* 1998, 41, 2390) in $CH_3CN$ (1.0 mL) was heated to 65° C. for 24 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 78 mg (78%) of the title compound. MS 799 $(M+H)^+$.

EXAMPLE 13

Compound 11 (Formula 1': $R_1$ is 3-phenyl-2-propynyl, $R_2$ is 3-phenyl-2-propynyl, $R_3$ is H, $R_4$ is H)

A solution of the compound from example 1, step G (80 mg, 0.12 mmol), triethylsilane (100 μL, 0.62 mmol), trifluoroacetic acid (48 μL, 0.62 mmol), and phenylpropargyl aldehyde (81 mg, 0.62 mmol) in $CH_3CN$ (1.0 mL) was heated to 60° C. for 2 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 73 mg (67%) of the title compound. MS 870 $(M+H)^+$.

EXAMPLE 14

Compound 12 (Formula 1': $R_1$ is 3-(3-pyridinyl)propyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (50 μL, 0.65 mmol), and 3-pyridinepropanal (84 mg, 0.62 mmol, prepared as described in *Bull. Chem. Soc. Jpn.* 1997, 70, 3061) in $CH_3CN$ (1.0 mL) was heated to 60° C. for 24 h. Additional triethylsilane (100 μL, 0.62 mmol) and trifluoroacetic acid (50 μL, 0.65 mmol) was added and heating at 60° C. was continued for 24 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 58 mg (61%) of the title compound. MS 761 $(M+H)^+$.

EXAMPLE 15

Compound 13 (Formula 1': $R_1$ is 3-phenyl-2-propynyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (50 μL, 0.65 mmol), and phenylpropargyl aldehyde (81 mg, 0.62 mmol) in $CH_3CN$ (1.0 mL) was stirred at room temperature for 25 min. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 18 mg (19%) of the title compound. MS 756 $(M+H)^+$.

EXAMPLE 16

Compound 14 (Formula 1': $R_1$ is 3-[4-(dimethylamino)phenyl]propyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (48 μL, 0.62 mmol), and 4-(dimethylamino) cinnamaldehyde (110 mg, 0.62 mmol) in $CH_3CN$ (1.0 mL) was heated to 60° C. for 24 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 38 mg (38%) of the title compound. MS 803 $(M+H)^+$.

EXAMPLE 17

Compound 15 (Formula 1': $R_1$ is (2E)-3-(4-nitrophenyl)-2-propenyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (48 μL, 0.62 mmol), and 4-nitrocinnamaldehyde (111 mg, 0.62 mmol) in $CH_3CN$ (1.0 mL) was stirred at room temperature for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 62 mg (67%) of the title compound. MS 803 (M+H)$^+$.

EXAMPLE 18

Compound 16 (Formula 1': R$_1$ is (2E)-3-(4-bromophenyl)-2-propenyl R$_2$ is H, R$_3$ is H, R$_4$ is H)

A solution of the compound from example 1, step G (256 mg, 0.40 mmol), triethylsilane (320 µL, 2.00 mmol), trifluoroacetic acid (160 µL, 2.08 mmol), and 4-bromocinnamaldehyde (422 mg, 2.00 mmol, prepared as described in *Tetrahedron* 1998, 54, 10761) in CH$_3$CN (3.0 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 156 mg (47%) of the title compound. MS 836 (M+H)$^+$.

EXAMPLE 19

Compound 18 (Formula 1': R$_1$ is (2E)-3-[4-(1H-pyrazol-1-yl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 30 (154 mg, 0.78 mmol) in CH$_3$CN (1.0 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 92 mg (72%) of the title compound. MS 824 (M+H)$^+$.

EXAMPLE 20

Compound 19 (Formula 1': R$_1$ is (2E)-3-[4-(2-pyridinyl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 32 (163 mg, 0.78 mmol) in CH$_3$CN (1.0 mL) was heated at 60° C. for 36 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 82 mg (63%) of the title compound. MS 835 (M+H)$^+$.

EXAMPLE 21

Compound 20 (Formula 1': R$_1$ is (2E)-3-[4-(1H-1, 2.4-triazol-1-yl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 35 (155 mg, 0.78 mmol) in CH$_3$CN (1.0 mL) was heated at 60° C. for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 96 mg (75%) of the title compound. MS 825 (M+H)$^+$.

EXAMPLE 22

Compound 21 (Formula 1': R$_1$ is (2E)-2-methyl-3-phenyl-2-propenyl, R$_2$ is H, R$_3$ is H, R$_4$ is H)

A solution of the compound from example 1, step G (100 mg, 0.16 mmol), triethylsilane (125 µL, 0.78 mmol), trifluoroacetic acid (60 µL, 0.78 mmol), and a-methyl-trans-cinnamaldehyde (110 µL, 0.79 mmol) in CH$_3$CN (0.5 mL) was stirred at room temperature for 40 h and then heated to 60° C. for 48 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 96:4:0.2 dichloromethane/methanol/conc. NH$_4$OH) yielded 46 mg (38%) of the title compound as an off-white solid. MS 772 (M+H)$^+$.

EXAMPLE 23

Compound 22 (Formula 1': R$_1$ is (2E)-3-[4-(1H-imidazol-1-yl)phenyl]-2-propenyl, R$_2$ is H, R$_3$ is H, R$_4$ is H)

A solution of the compound from example 1, step G (150 mg, 0.23 mmol), triethylsilane (186 µL, 1.169 mmol), trifluoroacetic acid (90 µL, 1.169 mmol), and the compound from Reference Example 37 (232 mg, 1.169 mmol) in CH$_3$CN (1.5 mL) was heated at 60° C. for 48 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 28 mg (15%) of the title compound. MS 824 (M+H)$^+$.

EXAMPLE 24

Compound 23 (Formula 1': R$_1$ is (2E)-3-[4-(3-pyridinyl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 24 (163 mg, 0.78 mmol) in CH$_3$CN (1.0 mL) was heated at 60° C. for 48 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 39 mg (30%) of the title compound. MS 835 (M+H)$^+$.

EXAMPLE 25

Compound 24 (Formula 1': R$_1$ is 3-(4-pyridinyl) propyl, R$_2$ is H, R$_3$ is H, R$_4$ is H)

A solution of the compound from example 1, step G (100 mg, 0.16 mmol), triethylsilane (250 µL, 1.56 mmol), trifluoroacetic acid (120 μL, 1.56 mmol), and the compound from Reference Example 2 (105 mg, 0.78 mmol) in $CH_3CN$ (1.0 mL) was heated at 60° C. for 48 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 26 mg (24%) of the title compound. MS 761 $(M+H)^+$.

EXAMPLE 26

Compound 25 (Formula 1': $R_1$ is 3-(4-quinolinyl)propyl, $R_2$ is H, $R_3$ is H, $R_4$ is H)

A solution of the compound from example 1, step G (100 mg, 0.16 mmol), triethylsilane (250 μL, 1.57 mmol), trifluoroacetic acid (120 μL, 1.56 mmol), and 4-quinolinepropanal (145 mg, 0.78 mmol, prepared as described in *J. Med Chem.* 1998, 41, 1660) in $CH_3CN$ (1.0 mL) was heated to 60° C. for 18 h. Additional trifluoroacetic acid (60 μL, 0.78 mmol) was added and heating at 60° C. was continued for 24 h. The reaction mixture was diluted with ethyl acetate (15 mL), washed with sat. aq. $NaHCO_3$ (10 mL) and brine (10 mL), dried ($Na_2SO_4$), and concentrated. Purification by chromatography ($SiO_2$, 95:5:0.2 dichloromethane/methanol/conc. $NH_4OH$) yielded 20 mg (16%) of the title compound as a brown solid. MS 811 $(M+H)^+$.

EXAMPLE 27

Compound 26 (Formula 1': $R_1$ is (2E)-3-[4-(4-pyridinyl)phenyl]-2-propenyl, $R_2$ is H, $R_3$ is H, $R_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 33 (163 mg, 0.78 mmol) in $CH_3CN$ (1.0 mL) was heated at 60° C. for 24 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 106 mg (82%) of the title compound. MS 835 $(M+H)^+$.

EXAMPLE 28

Compound 27 (Formula 1': $R_1$ is (2E)-3-[4-(5-pyrimidinyl)phenyl]-2-propenyl, $R_2$ is H, $R_3$ is H, $R_4$ is H)

A solution of the compound from example 1, step G (60 mg, 0.093 mmol), triethylsilane (150 μL, 0.94 mmol), trifluoroacetic acid (72 μL, 0.94 mmol), and the compound from Reference Example 34 (98 mg, 0.47 mmol) in $CH_3CN$ (1.0 mL) was heated at 60° C. for 18 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 36 mg (46%) of the title compound. MS 836 $(M+H)^+$.

EXAMPLE 29

Compound 28 (Formula 1': $R_1$ is [4-(5-pyrimidinyl)phenyl]methyl, $R_2$ is H, $R_3$ is H, $R_4$ is H)

A solution of the compound from example 1, step G (100 mg, 0.16 mmol), triethylsilane (124 μL, 0.78 mmol), trifluoroacetic acid (60 μL, 0.78 mmol), and 4-(5-pyrimidinyl)-benzaldehyde (144 mg, 0.78 mmol, prepared as described in WO 9828264) in $CH_3CN$ (1.0 mL) was heated at 60° C. for 5 days. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 11 mg (9%) of the title compound. MS 810 $(M+H)^+$.

EXAMPLE 30

Compound 29 (Formula 1': $R_1$ is 3-(3-quinolinyl)-2-propynyl, $R_2$ is H, $R_3$ is H, $R_4$ is H)

A solution of the compound from example 1, step G (80 mg, 0.12 mmol), triethylsilane (100 μL, 0.62 mmol), trifluoroacetic acid (46 μL, 0.62 mmol), and the compound from Reference Example 21 (113 mg, 0.62 mmol) in dichloromethane (1.0 mL) was heated at 50° C. for 6 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 97:3:0.1 dichloromethane/methanol/conc. $NH_4OH$) yielded 36 mg (36%) of the title compound. MS 807 $(M+H)^+$.

EXAMPLE 31

Compound 30 (Formula 1': $R_1$ is (2E)-3-(4-pyridinyl)-2-propenyl, $R_2$ is H, $R_3$ is H, $R_4$ is A solution of the compound from example 1, step G (100 mg, 0.16 mmol), triethylsilane (250 μL, 1.57 mmol), trifluoroacetic acid (120 μL, 1.56 mmol), and β-(4-pyridyl)acrolein oxalate (175 mg, 0.78 mmol) in $CH_3CN$ (1.0 mL) was heated to 60° C. for 18 h. Additional trifluoroacetic acid (60 μL, 0.78 mmol) and triethylsilane (125 μL, 0.78 mmol) were added and heating at 60° C. was continued for 24 h. The reaction mixture was diluted with ethyl acetate (15 mL), washed with sat. aq. $NaHCO_3$ (10 mL) and brine (10 mL), dried ($Na_2SO_4$), and concentrated. Purification by chromatography ($SiO_2$, 95:5:0.2 dichloromethane/methanol/conc. $NH_4OH$) yielded 40 mg (34%) of the title compound as an off-white solid. MS 759 $(M+H)^+$.

EXAMPLE 32

Compound 31 (Formula 1': $R_1$ is [4-(2-pyrimidinyl)phenyl]methyl, $R_2$ is H, $R_4$ is H, $R_4$ is H)

A solution of the compound from example 1, step G (100 mg, 0.16 mmol), triethylsilane (124 μL, 0.78 mmol), trifluoroacetic acid (60 μL, 0.78 mmol), and 4-(2-pyrimidinyl)-benzaldehyde (144 mg, 0.78 mmol, prepared as described in WO 9828264) in $CH_3CN$ (1.0 mL) was heated at 60° C. for 5 days. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 38 mg (30%) of the title compound. MS 810 $(M+H)^+$.

EXAMPLE 33

Compound 32 (Carbamic acid, [(2E)-3-[4-(2-pyrimidinyl)phenyl]-2-propenyl]-, (3aS,4R,7R,9R,10R,11R,13R,15R,15aR)-4-ethyltetradecahydro-3a,7,9,11,13,15-hexamethyl-2,6,8,14-tetraoxo-10-[[3,4,6-trideoxy-3-(dimethylamino)-β-D-xylo-hexopyranosyl]oxy]-2H-oxacyclotetradecino[4,3-d]oxazol-11-yl ester (Formula 1': $R_1$ is (2E)-3-[4-(2-pyrimidinyl)phenyl]-2-propenyl, $R_2$ is H, $R_3$ is H, $R_4$ is H)]

A solution of the compound from example 1, step G (100 mg, 0.16 mmol), triethylsilane (124 μL, 0.78 mmol), trifluoroacetic acid (60 µL, 0.78 mmol), and the compound from Reference Example 29 (170 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 62 mg (48%) of the title compound. MS 836 (M+H)$^+$.

EXAMPLE 34

Compound 33 (Formula 1': R$_1$ is (2E)-3-[4-(1H-1,2,3-triazol-1-yl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (120 µL, 1.56 mmol), and the compound from Reference Example 36 (160 mg, 0.78 mmol) in CH$_3$CN (1.0 mL) was heated at 60° C. for 5 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 63 mg (49%) of the title compound. MS 825 (M+H)$^+$.

EXAMPLE 35

Compound 34 (Formula 1': R$_1$ is (2E)-3-(4-quinolinyl)-2-propenyl, R$_2$, is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 38 (143 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 62 mg (49%) of the title compound. MS 809 (M+H)$^+$.

EXAMPLE 36

Compound 35 (Formula 1': R$_1$ is [3-(1H-pyrazol-1-yl)phenyl]methyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 3 (155 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 86 mg (67%) of the title compound. MS 824 (M+H)$^+$.

EXAMPLE 37

Compound 36 (Formula 1': R$_1$ is (2E)-3-[3-(2-pyridinyl)phenyl]-2-propenyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 39 (163 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 46 mg (35%) of the title compound. MS 835 (M+H)$^+$.

EXAMPLE 38

Compound 37 (Formula 1': R$_1$ is [3-(2-pyridinyl)phenyl]methyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 11 (146 mg, 0.78 mmol) in CH$_3$CN (1.0 mL) was heated at 60° C. for 6 days. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 38 mg (35%) of the title compound. MS 809 (M+H)$^+$.

EXAMPLE 39

Compound 38 (Formula 1': R$_1$ is (2E)-3-(6-Quinolinyl)-2-propenyl, R$_2$ is H, R$_3$ is H, R$_4$ is H)

A solution of the compound from example 1, step G (100 mg, 0.16 mmol), triethylsilane (250 µL, 1.57 mmol), trifluoroacetic acid (120 µL, 1.56 mmol), and the compound from Reference Example 28 (145 mg, 0.79 mmol) in CH$_3$CN (1.0 mL) was heated to 60° C. for 18 h. Additional trifluoroacetic acid (60 µL, 0.78 mmol) was added and heating at 60° C. was continued for 24 h. A third portion of trifluoroacetic acid (60 µL, 0.78 mmol) was added and heating at 60° C. was continued for 24 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 94:6:0.4 dichloromethane/methanol/conc. NH$_4$OH) yielded 49 mg (39%) of the title compound as a yellow solid. MS 809 (M+H)$^+$.

EXAMPLE 40

Compound 39 (Formula 1': R$_1$ is [4-(1H-pyrazol-3-yl)phenyl]methyl, R$_2$ is H, R$_3$ is H, R$_4$ is H)

A solution of the compound from example 1, step G (100 mg, 0.16 mmol), triethylsilane (124 µL, 0.78 mmol), trifluoroacetic acid (60 µL, 0.78 mmol), and 4-(1H-pyrazol-3-yl)benzaldehyde (136 mg, 0.78 mmol, prepared as described in *J. Med. Chem.* 1998, 41, 2390) in CH$_3$CN (1.0 mL) was heated at 60° C. for 48 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 80 mg (65%) of the title compound. MS 798 (M+H)$^+$.

EXAMPLE 41

Compound 41 (Formula 1': R$_1$ is (2E)-3-(6-Quinoxalinyl)-2-propenyl, R$_2$ is H, R$_3$ is H, R$_4$ is H)

A solution of the compound from example 1, step G (100 mg, 0.16 mmol), triethylsilane (250 µL, 1.57 mmol), trifluoroacetic acid (120 µL, 1.56 mmol), and the compound from Reference Example 27 (145 mg, 0.79 mmol) in $CH_3CN$ (1.0 mL) was heated to 60° C. for 20 h. The reaction mixture was diluted with ethyl acetate (15 mL), washed with sat. aq. $NaHCO_3$ (10 mL) and brine (10 mL), dried ($Na_2SO_4$), and concentrated. Purification by chromatography ($SiO_2$, 94:6:0.2 dichloromethane/methanol/conc. $NH_4OH$) yielded 69 mg (55%) of the title compound as a brown solid. MS 810 $(M+H)^+$.

EXAMPLE 42

Compound 42 (Formula 1': $R_1$ is [4-(5-nitro-2-pyridinyl)phenyl]methyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 19 (178 mg, 0.78 mmol) in $CH_3CN$ (1.0 mL) was heated at 60° C. for 36 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 40 mg (30%) of the title compound. MS 854 $(M+H)^+$.

EXAMPLE 43

Compound 43 (Carbamic acid, [(2E)-3-[4-(1-methyl-1H-pyrazol-3-yl)phenyl]-2-propenyl]-, (3aS,4R,7R,9R,10R,11R,13R,15R,15aR)-4-ethyltetradecahydro-3a,7,9,11,13,15-hexamethyl-2,6,8,14-tetraoxo-10-[[3,4,6-trideoxy-3-(dimethylamino)-β-D-xylo-hexopyranosyl]oxy]-2H-oxacyclotetradecino[4,3-d]oxazol-11-yl ester: Formula 1': $R_1$ is (2E)-3-[4-(1-methyl-1H-pyrazol-3-yl)phenyl]-2-propenyl, $R_2$ is H, $R_3$ is H, $R_4$ is H)

A solution of the compound from example 1, step G (110 mg, 0.17 mmol), triethylsilane (130 µL, 0.81 mmol), trifluoroacetic acid (70 µL, 0.91 mmol), and the compound from Reference Example 43 (182 mg, 0.86 mmol) in $CH_3CN$ (1.0 mL) was heated at 60° C. for 18 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 56 mg (39%) of the title compound. MS 838 $(M+H)^+$.

EXAMPLE 44

Compound 44 (Formula 1': $R_1$ is (2E)-3-[4-(1-methyl-1H-pyrazol-5-yl)phenyl]-2-propenyl, $R_2$ is H, $R_3$ is H, $R_4$ is H)

A solution of the compound from example 1, step G (110 mg, 0.17 mmol), triethylsilane (130 µL, 0.81 mmol), trifluoroacetic acid (70 µL, 0.91 mmol), and the compound from Reference Example 44 (182 mg, 0.86 mmol) in $CH_3CN$ (1.0 mL) was heated at 60° C. for 6 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 82 mg (58%) of the title compound. MS 838 $(M+H)^+$.

EXAMPLE 45

Compound 45 (Formula 1': $R_1$ is (2E)-3-[4-(5-nitro-2-pyridinyl)phenyl]-2-propenyl, $R_2$ is H, $R_3$ is H, $R_4$ is H)

A solution of the compound from Example 1, step G (80 mg, 0.12 mmol), triethylsilane (120 µL, 0.75 mmol), trifluoroacetic acid (100 µL, 1.30 mmol), and the compound from Reference Example 45 (158 mg, 0.62 mmol) in $CH_3CN$ (1.5 mL) was heated to 60° C. for 6 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 62 mg (56%) of the title compound. MS 880 $(M+H)^+$.

EXAMPLE 46

Compound 46 (Formula 1': $R_1$ is (2E)-3-(8-Quinolinyl)-2-propenyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 46 (143 mg, 0.78 mmol) in $CH_3CN$ (1.0 mL) was heated at 60° C. for 18 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 32 mg (25%) of the title compound. MS 809 $(M+H)^+$.

EXAMPLE 47

Compound 47 (Formula 1': $R_1$ is (2E)-3-(7-Quinolinyl)-2-propenyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 47 (143 mg, 0.78 mmol) in $CH_3CN$ (1.0 mL) was heated at 60° C. for 48 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 40 mg of the title compound mixed with the compound from example 1, step G. This mixture was re-subjected to the above reaction conditions and purified as above to give 15 mg (12%) of the title compound. MS 809 $(M+H)^+$.

EXAMPLE 48

Compound 48 (Formula 1': $R_1$ is (2E)-3-[6-(1H-pyrazol-1-yl)-2-pyridinyl]-2-propenyl. $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 48 (156 mg, 0.78 mmol) in $CH_3CN$ (1.0 mL) was heated at 60° C. for 48 h. An additional amount of the compound from Reference Example (78 mg, 0.39 mmol) was added and heating at 60° C. was continued for an additional 48 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 24 mg (19%) of the title compound. MS 825 $(M+H)^+$.

EXAMPLE 49

Compound 49 (Formula 1': $R_1$ is (2E)-3-[6-(1H-pyrazol-1-yl)-3-pyridinyl]-2-propenyl, $R_2$ is H, $R_3$ is H, $R_4$ is H)

A solution of the compound from example 1, step G (50 mg, 0.078 mmol), triethylsilane (125 µL, 0.78 mmol), trifluoroacetic acid (60 μL, 1.17 mmol), and the compound from Reference Example 22 (78 mg, 0.39 mmol) in CH$_3$CN (0.5 mL) was heated to 60° C. for 18 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.4 dichloromethane/methanol/conc. NH$_4$OH) yielded 44 mg (34%) of the title compound. MS 825 (M+H)$^+$.

EXAMPLE 50

Compounds 50 and 51 (Formula 1', Compounds 50: R$_1$ is (2E,4E)-5-[6-(1H-1,2,4-triazol-1-yl)-2-pyridinyl]-2,4-pentadienyl, R$_2$ is H, R$_3$ is H, R$_4$ is H: Compounds 51: R$_1$ is (2E)-3-[6-(1H-1,2,4-triazol-1-yl)-2-pyridinyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the mixture of compounds from Reference Example 31 (157 mg, 0.78 mmol) in CH$_3$CN (1.0 mL) was heated at 60° C. for 48 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 92:8:0.1 dichloromethane/methanol/conc. NH$_4$OH) yielded 12 mg (9%) of Compound 50 [MS 852 (M+H)$^+$] and 16 mg (12%) of Compound 51 [MS 826 (M+H)$^+$].

EXAMPLE 51

Compound 52 (Formula 1': R$_1$ is (2E)-3-(4-Isoquinolinyl)-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 49 (143 mg, 0.78 mmol) in CH$_3$CN (1.0 mL) was heated at 60° C. for 72 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 94:6:0.1 dichloromethane/methanol/conc. NH$_4$OH) yielded 28 mg (22%) of the title compound. MS 809 (M+H)$^+$.

EXAMPLE 52

Compound 53 (Formula 1': R$_1$ is (2E)-3-[3-Fluoro-4-(1H-1,2,4-triazol-1-yl)phenyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 51 (170 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 102 mg (78%) of the title compound. MS 843 (M+H)$^+$.

EXAMPLE 53

Compound 54 (Formula 1': R$_1$ is 3,3-diphenyl-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and β-phenylcinnamaldehyde (163 mg, 0.78 mmol) in CH$_3$CN (1.0 mL) was heated at 60° C. for 4 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 38 mg (29%) of the title compound. MS 834 (M+H)$^+$.

EXAMPLE 54

Compound 55 (Formula 1': R$_1$ is [3-fluoro-4-(1H-1,2,4-triazol-1-yl)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 7 (149 mg, 0.78 mmol) in CH$_3$CN (1.0 mL) was heated at 60° C. for 36 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 93:7:0.1 dichloromethane/methanol/conc. NH$_4$OH) yielded 78 mg (61%) of the title compound. MS 817 (M+H)$^+$.

EXAMPLE 55

Compound 56 (Formula 1': R$_1$ is [5-(2-pyridinyl)-2-thiophenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and 5-(2-pyridinyl)-2-thiophenecarboxaldehyde (148 mg, 0.78 mmol, prepared as described in J. Chem Soc., Perkin Trans. 2 1998, 437) in CH$_3$CN (1.0 mL) was heated at 60° C. for 72 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 48 mg (38%) of the title compound. MS 815 (M+H)$^+$.

EXAMPLE 56

Compound 57 (Formula 1': R$_1$ is (2E)-3-[5-(2-pyridinyl)-2-thienyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 52 (170 mg, 0.78 mmol) in CH$_3$CN (1.0 mL) was heated at 60° C. for 12 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 71 mg (54%) of the title compound. MS 841 (M+H)$^+$.

EXAMPLE 57

Compound 58 (Formula 1': (R$_1$ is (2E)-3-[3-fluoro-4-(1H-pyrazol-1-yl)phenyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 µL, 0.78 mmol), and the compound from Reference Example 50 (170 mg, 0.78 mmol) in $CH_3CN$ (1.0 mL) was stirred at room temperature for 24 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 106 mg (81%) of the title compound. MS 842 $(M+H)^+$.

EXAMPLE 58

Compound 59 (Formula 1': $R_1$ is [3-fluoro-4-(1H-pyrazol-1-yl)phenyl]methyl. $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 6 (150 mg, 0.78 mmol) in $CH_3CN$ (1.0 mL) was heated at 60° C. for 18 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 94:6:0.1 dichloromethane/methanol/conc. $NH_4OH$) yielded 78 mg (61%) of the title compound. MS 816 $(M+H)^+$.

EXAMPLE 59

Compound 60 (Formula 1': $R_1$ is (2E,4E)-5-[4-(1H-pyrazol-1-yl)phenyl]-2,4-pentadienyl, $R_2$ is H, $R_3$ is H, $R_4$ is H)

A solution of the compound from example 1, step G (120 mg, 0.19 mmol), triethylsilane (145 µL, 0.91 mmol), trifluoroacetic acid (72 µL, 0.93 mmol), and the compound from Reference Example 53 (210 mg, 0.94 mmol) in $CH_3CN$ (1.0 mL) was heated at 60° C. for 4 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 98 mg (62%) of the title compound. MS 850 $(M+H)^+$.

EXAMPLE 60

Compound 61 (Formula 1': $R_1$ is (1-phenyl-1H-pyrazol-4-yl)methyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and 1-phenyl-1H-pyrazol-4-ylcarboxaldehyde (134 mg, 0.78 mmol, prepared as described in *Synth. Commun.* 1998, 28,1299) in $CH_3CN$ (1.0 mL) was stirred at room temperature for 12 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 86 mg (69%) of the title compound. MS 798 $(M+H)^+$.

EXAMPLE 61

Compound 62 (Formula 1': $R_1$ is (2E)-3-(1-phenyl-1H-pyrazol-4-yl)-2-propenyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 54 (155 mg, 0.78 mmol) in $CH_3CN$ (1.0 mL) was stirred at room temperature for 12 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 46 mg (36%) of the title compound. MS 824 $(M+H)^+$.

EXAMPLE 62

Compound 64 (Formula 1': $R_1$ is [4-(4-methyl-1H-pyrazol-1-yl)phenyl]methyl $R_2$ is H, $R_3$ is H, $R_4$ is H)

A solution of the compound from example 1, step G (110 mg, 0.17 mmol), triethylsilane (124 µL, 0.78 mmol), trifluoroacetic acid (60 µL, 0.78 mmol), and the compound from Reference Example 4 (152 mg, 0.82 mmol) in $CH_3CN$ (1.0 mL) was heated at 60° C. for 4 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.1 dichloromethane/methanol/conc. $NH_4OH$) yielded 70 mg (50%) of the title compound. MS 812 $(M+H)^+$.

EXAMPLE 63

Compound 65 (Formula 1': $R_1$ is [3-(2-pyrimidinyl) phenyl]methyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 12 (144 mg, 0.78 mmol) in $CH_3CN$ (1.0 mL) was heated at 60° C. for 72 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 36 mg (29%) of the title compound. MS 810 $(M+H)^+$.

EXAMPLE 64

Compound 66 (Formula 1': $R_1$ is (2E)-3-[3-(2-pyrimidinyl)phenyl]-2-propenyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 µL, 0.78 mmol), and the compound from Reference Example 40 (170 mg, 0.78 mmol) in $CH_3CN$ (1.0 mL) was heated at 60° C. for 3 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 95:5:0.1 dichloromethane/methanol/conc. $NH_4OH$) yielded 38 mg (27%) of the title compound. MS 836 $(M+H)^+$.

EXAMPLE 65

Compound 67 (Formula 1': $R_1$ is (2E)-3-[4-(4-methyl-1H-pyrazol-1-yl)phenyl]-2-propenyl, $R_2$ is H, $R_3$ is H, $R_4$ is H)

A solution of the compound from example 1, step G (100 mg, 0.16 mmol), triethylsilane (124 µL, 0.78 mmol), trifluoroacetic acid (60 μL, 0.78 mmol), and the compound from Reference Example 55 (170 mg, 0.80 mmol) in CH$_3$CN (1.0 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 98 mg (69%) of the title compound. MS 838 (M+H)$^+$.

EXAMPLE 66

Compound 69 (Formula 1': R$_1$ is [4-(4-methyl-2-pyrimidinyl)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 14 (156 mg, 0.78 mmol) in CH$_3$CN (1.0 mL) was heated at 60° C. for 72 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 94:6:0.1 dichloromethane/methanol/conc. NH$_4$OH) yielded 43 mg (33%) of the title compound. MS 824 (M+H)$^+$.

EXAMPLE 67

Compound 68 (Formula 1': R$_1$ is (2E)-3-[4-(4-methyl-2-pyrimidinyl)phenyl]-2-propenyl R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 41 (175 mg, 0.78 mmol) in CH$_3$CN (1.0 mL) was heated at 60° C. for 4 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 94:6:0.1 dichloromethane/methanol/conc. NH$_4$OH) yielded 78 mg (59%) of the title compound. MS 850 (M+H)$^+$.

EXAMPLE 68

Compound 70 (Formula 1': R$_1$ is [4-(4-methoxy-2-pyrimidinyl)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 13 (167 mg, 0.78 mmol) in CH$_3$CN (1.0 mL) was heated at 60° C. for 36 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 62 mg (47%) of the title compound. MS 840 (M+H)$^+$.

EXAMPLE 69

Compound 71 (Formula 1': R$_1$ is (R$_1$ is (2E)-3-[4-(4-methoxy-2-pyrimidinyl)phenyl]-2-propenyl, R$_2$ is H, R$_3$ is H, R$_4$ is H A solution of the compound from example 1, step G (150 mg, 0.23 mmol), triethylsilane (180 μL, 1.17 mmol), trifluoroacetic acid (90 μL, 1.17 mmol), and the compound from Reference Example 56 (281 mg, 1.17 mmol) in CH$_3$CN (2.0 mL) was heated at 60° C. for 5 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 110 mg (55%) of the title compound. MS 866 (M+H)$^+$.

EXAMPLE 70

Compound 72 (Formula 1': R$_1$ is (2E)-3-(6-Bromo-3-pyridinyl)-2-propenyl, R$_2$ is H, R$_3$ is H, R$_4$ is H)

A solution of the compound from example 1, step G (100 mg, 0.16 mmol), triethylsilane (250 μL, 1.57 mmol), trifluoroacetic acid (120 μL, 1.56 mmol), and the compound from Reference Example 23 (165 mg, 0.79 mmol) in CH$_3$CN (1.0 mL) was heated to 60° C. for 18 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.5 dichloromethane/methanol/conc. NH$_4$OH) yielded 94 mg (72%) of the title compound. MS 837 (M+H)$^+$.

EXAMPLE 71

Compound 73 (Formula 1': R$_1$ is [2-fluoro-4-(1H-pyrazol-1-yl)phenyl]methyl, R$_2$ is H, R$_3$ is H, R$_4$ is H)

A solution of the compound from example 1, step G (100 mg, 0.16 mmol), triethylsilane (250 μL, 1.57 mmol), trifluoroacetic acid (120 μL, 1.56 mmol), and the compound from Reference Example 8 (148 mg, 0.78 mmol) in CH$_3$CN (1.0 mL) was stirred at room temperature for 48 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.5 dichloromethane/methanol/conc. NH$_4$OH) yielded 75 mg (59%) of the title compound. MS 816 (M+H)$^+$.

EXAMPLE 72

Compound 74 (Formula 1': R$_1$ is (2E)-3-[2-fluoro-4-(1H-pyrazol-1-yl)phenyl]-2-propenyl, R$_2$ is H, R$_3$ is H, R$_4$ is H)

A solution of the compound from example 1, step G (100 mg, 0.16 mmol), triethylsilane (250 μL, 1.57 mmol), trifluoroacetic acid (120 μL, 1.56 mmol), and the compound from Reference Example 25 (168 mg, 0.78 mmol) in CH$_3$CN (1.0 mL) was heated to 60° C. for 4 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.2 dichloromethane/methanol/conc. NH$_4$OH) yielded 58 mg (44%) of the title compound. MS 842 (M+H)$^+$.

EXAMPLE 73

Compound 76 (Formula 1': R$_1$ is (4-pyrazinylphenyl)methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 17 (144 mg, 0.78 mmol) in CH$_3$CN (1.0 mL) was heated at 60° C. for 4 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 94:6:0.1 dichloromethane/methanol/conc. NH$_4$OH) yielded 96 mg (76%) of the title compound. MS 810 (M+H)$^+$.

EXAMPLE 74

Compound 77 (Carbamic acid, [(2E)-3-(4-pyrazinylphenyl)-2-propenyl]-, (3aS,4R,7R,9R,10R,11R,13R,15R,15aR)-4-ethyltetradecahydro-3a,7,9,11,13,15-hexamethyl-2,6,8,14-tetraoxo-10-[[3,4,6-trideoxy-3-(dimethylamino)-β-D-xylo-hexopyranosyl]oxy]-2H-oxacyclotetradecino[4,3-d]oxazol-11-yl ester; Formula 1': R$_1$ is (2E)-3-(4-pyrazinylphenyl)-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 57 (164 mg, 0.78 mmol) in CH$_3$CN (1.0 mL) was heated at 60 IC for 12 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 116 mg (89%) of the title compound. MS 836 (M+H)$^+$.

EXAMPLE 75

Compound 78 (Formula 1': R$_1$ is (2E)-3-[4-(4-pyrimidinyl)phenyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 58 (164 mg, 0.78 mmol) in CH$_3$CN (1.0 mL) was heated at 60 IC for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 121 mg (92%) of the title compound. MS 836 (M+H)$^+$.

EXAMPLE 76

Compound 79 (Formula 1': R$_1$ is [4-(4-pyrimidinyl)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 18 (144 mg, 0.78 mmol) in CH$_3$CN (1.0 mL) was heated at 60 IC for 18 h. Additional triethylsilane (250 μL, 1.56 mmol) and trifluoroacetic acid (120 μL, 1.56 mmol) was added and heating at 60 IC was continued for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 96:4:0.1 dichloromethane/methanol/conc. NH$_4$OH) yielded 121 mg (92%) of the title compound. MS 810 (M+H)$^+$.

EXAMPLE 77

Compound 81 (Formula 1': R$_1$ is [3-methoxy-4-(1H-pyrazol-1-yl)phenyl]methyl, R$_2$ is H, R$_3$ is H, R$_4$ is H)

A solution of the compound from example 1, step G (100 mg, 0.16 mmol), triethylsilane (250 μL, 1.57 mmol), trifluoroacetic acid (120 μL, 1.56 mmol), and the compound from Reference Example 5 (158 mg, 0.78 mmol) in CH$_3$CN (1.0 mL) was heated to 60° C. for 18 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.2 dichloromethane/methanol/conc. NH$_4$OH) yielded 82 mg (64%) of the title compound. MS 828 (M+H)$^+$.

EXAMPLE 78

Compound 82 (Formula 1': R$_1$ is 3-[4-(1H-pyrazol-1-yl)phenyl]-2-propynyl, R$_2$ is H, R$_3$ is H, R$_4$ is H)

A solution of the compound from example 1, step G (50 mg, 0.078 mmol), triethylsilane (75 μL, 0.47 mmol), trifluoroacetic acid (36 μL, 0.47 mmol), and the compound from Reference Example 20 (46 mg, 0.23 mmol) in dichloromethane (0.5 mL) was stirred at room temperature for 72 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.2 dichloromethane/methanol/conc. NH$_4$OH) yielded 22 mg (34%) of the title compound. MS 822 (M+H)$^+$.

EXAMPLE 79

Compound 83 (Formula 1': R$_1$ is [4-(2-pyrimidinyloxy)phenyl]methyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 μL, 0.78 mmol), and the compound from Reference Example 9 (156 mg, 0.78 mmol) in CH$_3$CN (1.0 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 80 mg (62%) of the title compound. MS 826 (M+H)$^+$.

EXAMPLE 80

Compound 84 (Formula 1': R$_1$ is (2E)-3-[3-methoxy-4-(1H-pyrazol-1-yl)phenyl]-2-propenyl R$_2$ is H, R$_3$ is H, R$_4$ is H)

A solution of the compound from example 1, step G (100 mg, 0.16 mmol), triethylsilane (250 μL, 1.57 mmol), trifluoroacetic acid (120 μL, 1.56 mmol), and the compound from Reference Example 26 (178 mg, 0.78 mmol) in CH$_3$CN (1.0 mL) was heated to 60° C. for 5 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 96:4:0.5 dichloromethane/methanol/conc. NH$_4$OH) yielded 72 mg (54%) of the title compound. MS 854 (M+H)$^+$.

EXAMPLE 81

Compound 86 (Formula 1': R$_1$ is (2E)-3-[4-(2-pyrimidinyloxy)phenyl]-2-propenyl, R$_2$ is H, R$_3$ is H, R$_4$ is H)

A solution of the compound from example 1, step G (100 mg, 0.16 mmol), triethylsilane (124 μL, 0.78 mmol), trifluoroacetic acid (60 µL, 0.78 mmol), and the compound from Reference Example 59 (177 mg, 0.78 mmol) in CH$_3$CN (1.0 mL) was stirred at room temperature for 12 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 50 mg (38%) of the title compound. MS 852 (M+H)$^+$.

EXAMPLE 82

Compound 87 (Formula 1': R$_1$ is [2-fluoro-4-(2-pyrimidinyl)phenyl]methyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 15 (158 mg, 0.78 mmol) in CH$_3$CN (1.0 mL) was stirred at room temperature for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 96 mg (74%) of the title compound. MS 828 (M+H)$^+$.

EXAMPLE 83

Compound 88 (Formula 1': R$_1$ is (2E)-3-[2-fluoro-4-(2-pyrimidinyl)phenyl]-2-propenyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 60 (178 mg, 0.78 mmol) in CH$_3$CN (1.0 mL) was stirred at room temperature for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 106 mg (80%) of the title compound. MS 854 (M+H)$^+$.

EXAMPLE 84

Compound 92 (Formula 1': R$_1$ is (2E)-3-[1-(2-pyrimidinyl)-1H-imidazol-4-yl]-2-propenyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 62 (156 mg, 0.78 mmol) in CH$_3$CN (1.0 mL) was stirred at room temperature for 36 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 90 mg (70%) of the title compound. MS 826 (M+H)$^+$.

EXAMPLE 85

Compound 93 (Formula 1': R$_1$ is [1-(2-pyrimidinyl)-1H-imidazol-4-yl]methyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 10 (136 mg, 0.78 mmol) in CH$_3$CN (1.0 mL) was heated at 60° C. for 18 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 32 mg (26%) of the title compound. MS 800 (M+H)$^+$.

EXAMPLE 86

Compound 96 (Formula 1': R$_1$ is (2E)-3-[4-(3-pyridazinyl)phenyl]-2-propenyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 61 (164 mg, 0.78 mmol) in CH$_3$CN (1.0 mL) was stirred at room temperature for 120 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 50 mg (38%) of the title compound. MS 836 (M+H)$^+$.

EXAMPLE 87

Compound 97 (Formula 1': R$_1$ is [4-(3-pyridazinyl)phenyl]methyl, R$_2$ is H, R$_3$ is H, R$_4$ is H)

A solution of the compound from example 1, step G (100 mg, 0.16 mmol), triethylsilane (240 µL, 1.50 mmol), trifluoroacetic acid (120 µL, 1.56 mmol), and the compound from Reference Example 16 (144 mg, 0.78 mmol) in CH$_3$CN (1.0 mL) was heated at 60° C. for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 28 mg (22%) of the title compound. MS 810 (M+H)$^+$.

EXAMPLE 88

Compound 63: 2'-Acetate of the Compound 20

The title compound was prepared from Compound 20 by a procedure analogous to Example 1, step D. MS 867 (M+H)$^+$.

EXAMPLE 89

Compound 94: 2'-acetate of Compound 32

(R$_1$ is (2E)-3-[4-(2-pyrimidinyl)phenyl]-2-propenyl, R$_2$ is H, R$_3$ is H, R$_4$ is H)

A solution of the compound from example 1, step F (150 mg, 0.22 mmol), triethylsilane (340 µL, 2.13 mmol), trifluoroacetic acid (170 µL, 2.21 mmol), and the compound from Reference Example 29 (230 mg, 1.09 mmol) in CH$_3$CN (1.5 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 25–50% acetone/hexane) yielded 80 mg (42%) of the title compound. MS 878 (M+H)$^+$.

EXAMPLE 90

Compound 40 (Formula 1': $R_1$ is (2E)-3-[4-(4H-1,2,4-triazol-4-yl)phenyl]-2-propenyl, $R_2$ is H, $R_3$ is H, $R_4$ is H)

Step A

A mixture of tin(II) chloride (450 mg, 2.37 mmol) and the compound from Example 17 (Compound 15, 375 mg, 0.47 mmol) in ethanol (10 mL) was heated to reflux for 1 h. The cooled reaction mixture was diluted with 15% aq. NaOH (15 mL) and extracted with dichloromethane (3×15 mL). The combined organic layers were washed with water (20 mL) and brine (20 mL), dried (MgSO$_4$), and concentrated. Purification by chromatography (SiO$_2$, 95:5:0.2 dichloromethane/methanol/conc. NH$_4$OH) yielded 185 mg (5%) of the amine. MS 773 (M+H)$^+$.

Step B

N,N-dimethylformamide azine dihydrochloride (32 mg, 0.15 mmol) and the amine from step A (75 m g, 0.097 mol) in pyridine (0.5 mL) were heated to 115° C. for 18 h. The cooled reaction mixture was diluted with water (10 mL) and extracted with ethyl acetate (3×10 mL). The combined organic layers were washed with water (10 mL) and brine (10 mL), dried (Na$_2$SO$_4$), and concentrated. Purification by chromatography (SiO$_2$, 94:6:0.2 dichloromethane/methanol/conc. NH$_4$OH) followed by a second chromatography (SiO$_2$, 97:3 acetonitrile/triethylamine) yielded 24 mg (30%) of the title compound. MS 825 (M+H)$^+$.

EXAMPLE 91

Compound 17 (Formula 1': $R_1$ is [1,1'-biphenyl]4-ylmethyl, $R_2$ is H, $R_3$ is H, $R_4$ is H)

A solution of the compound from Example 18 (Compound 16, 50 mg, 0.060 mmol) and tetrakis(triphenylphosphine)palladium(0) (4.0 mg, 0.0035 mmol) in toluene (1.0 mL) was treated with 2 M Na$_2$CO$_3$ (1.0 mL) and a solution of phenylboronic acid (8.8 mg, 0.072 mmol) in methanol (1.0 mL). The biphasic mixture was heated to reflux for 4 h. The cooled reaction mixture was diluted with dichloromethane (20 mL), washed with sat. aq. NaHCO$_3$ (10 mL) and brine (10 mL), dried (MgSO$_4$), and concentrated. Purification by chromatography (SiO$_2$, 97:3:0.1 dichloromethane/methanol/conc. NH$_4$OH) yielded 36 mg (72%) of the title compound. MS 834 (M+H)$^+$.

EXAMPLE 92

Compound 80 (Carbamic acid, [3-[4-(2-2pyrimidinyl)phenyl]propyl]-, (3aS,4R,7R,9R,10R,11R,13R,15R,15aR)-4-ethyltetradecahydro-3a,7,9,11,13,15-hexamethyl-2,6,8,14-tetraoxo-10-[[3,4,6-trideoxy-3-(dimethylamino)-b-β-xylo-hexopyranosyl]oxy]-2H-oxacyclotetradecino[4,3-d]oxazol-11-yl ester; Formula 1': $R_1$ is 3-[4-(2-pyrimidinyl)phenyl]propyl, $R_2$ is H, $R_3$ is H, $R_4$ is H)

10% Pd/C (25 mg) was added to a solution of the compound from Example 33 (Compound 32, 55 mg, 0.066 mmol) and ammonium formate (21 mg, 0.33 mmol) in methanol (1 mL). After 30 min, the catalyst was filtered off through a pad of Celite and the filter cake was washed with methanol (20 mL). The combined filtrate was concentrated and the residue purified by chromatography (SiO$_2$, 95:5:0.2 dichloromethane/methanol/conc. NH$_4$OH) to yield 32 mg (58%) of the title compound. MS 838 (M+H)$^+$.

EXAMPLE 93

Compound 85 (Formula 1': $R_1$ is (2E)-3-[4-(2-pyrimidinyl)phenyl]-2-propenyl, $R_2$ is methyl, $R_3$ is H, $R_4$ is H)

A solution of the compound from example 33 (Compound 32, 50 mg, 0.060 mmol), triethylsilane 95 μL, 0.59 mmol), trifluoroacetic acid (45 μL, 0.58 mmol), and paraformaldehyde (9 mg, 0.30 mmol) in CH$_3$CN (1.0 mL) was heated at 60° C. for 18 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 33 mg (65%) of the title compound. MS 850 (M+H)$^+$.

EXAMPLE 94

Compound 75 (Formula 1': $R_1$ is (2E)-3-[4-(2-pyrimidinyl)phenyl]-2-propenyl, $R_2$ is H, $R_3$ is H, $R_4$ is F)

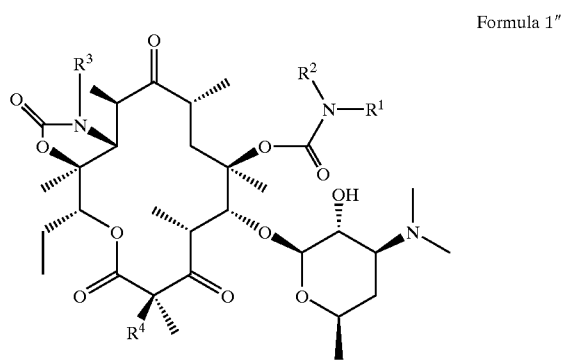

Formula 1''

A solution of Compound 105 (92 mg, 0.14 mmol), triethylsilane (225 μL, 1.39 mmol), trifluoroacetic acid (110 μL, 1.43 mmol), and the compound from Reference Example 29 (147 mg, 0.70 mmol) in CH$_3$CN (1.0 mL) was stirred at room temperature for 48 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.2 dichloromethane/methanol/conc. NH$_4$OH) yielded 29 mg (24%) of the title compound. MS 854 (M+H)$^+$.

EXAMPLE 95

Compound 89 (Formula 1': $R_1$ is (2E)-3-[4-(2-pyrimidinyl)phenyl]-2-propenyl, $R_2$ is H, $R_3$ is H, $R_4$ is F)

A solution of the compound from example 2 (100 mg, 0.15 mmol), triethylsilane (240 μL, 1.50 mmol), trifluoroacetic acid (120 μL, 1.56 mmol), and the compound from Reference Example 29 (160 mg, 0.76 mmol) in CH$_3$CN (1.0 mL) was stirred at room temperature for 6 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 71 mg (55%) of the title compound. MS 854 (M+H)$^+$.

EXAMPLE 96

Compound 90 (Formula 1': $R_1$ is (2E)-3-(6-quinolinyl)-2-propenyl, $R_2$ is H, $R_3$ is H, $R_4$ is F)

A solution of the compound from example 2 (100 mg, 0.15 mmol), triethylsilane (240 μL, 1.50 mmol), trifluoroacetic acid (120 μL, 1.56 mmol), and the compound from Reference Example 28 (140 mg, 0.76 mmol) in CH$_3$CN (1.0 mL) was stirred at room temperature for 6 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 90 mg (72%) of the title compound. MS 827 (M+H)$^+$.

EXAMPLE 97

Compound 91 (Formula 1': R$_1$ is (2E)-3-[4-(1H-pyrazol-1-yl)phenyl]-2-propenyl, R$_2$ is H, R$_3$ is H, R$_4$ is F)

A solution of the compound from example 2 (100 mg, 0.15 mmol), triethylsilane (240 µL, 1.50 mmol), trifluoroacetic acid (120 µL, 1.56 mmol), and the compound from Reference Example 30 (150 mg, 0.76 mmol) in CH$_3$CN (1.0 mL) was stirred at room temperature for 3 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 80 mg (63%) of the title compound. MS 842 (M+H)$^+$.

EXAMPLE 98

Compound 98 (Formula 1': R$_1$ is (2E)-3-(4-pyrazinylphenyl)-2-propenyl, R$_2$ is H, R$_3$ is H, R$_4$ is hydroxy)

Charcoal (500 mg) was added to a solution of the compound from example 74 (Compound 77, 879 mg, 1.05 mmol) in methanol (15 mL) and the mixture was stirred under an air atmosphere for 18 h. The reaction mixture was filtered through a pad of Celite, the filtered solids were rinsed with additional methanol, and the combined filtrate was concentrated. The residue obtained was stirred in a biphasic mixture of dichloromethane (50 mL) and 10% aq. NaHSO$_3$ (50 mL) for 3 h. The organic layer was separated, dried (MgSO$_4$), and concentrated. Purification by chromatography (SiO$_2$, 5–6% methanol in dichloromethane containing 0.2% conc. NH$_4$OH) yielded 137 mg of recovered starting material and 334 mg (37%) of the title compound. MS 852 (M+H)$^+$.

EXAMPLE 99

Compound 99 (Formula 1': R$_1$ is (2E)-3-[4-(3-pyridazinyl)phenyl]-2-propenyl, R$_2$ is H, R$_3$ is H, R$_4$ is F)

A solution of the compound from example 2 (66 mg, 0.10 mmol), triethylsilane (80 µL, 0.50 mmol), trifluoroacetic acid (40 µL, 0.52 mmol), and the compound from Reference Example 61 (105 mg, 0.50 mmol) in dichloromethane (0.8 mL) was stirred at room temperature for 18 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) followed by a second chromatography (SiO$_2$, acetone/triethylamine 100:1) yielded 34 mg (40%) of the title compound. MS 854 (M+H)$^+$.

EXAMPLE 100

Compound 100 (Formula 1': R$_1$ is (2E)-3-[4-(4-pyrimidinyl)phenyl]-2-propenyl, R$_2$ is H, R$_3$ is H, R$_4$ is F)

A solution of the compound from example 2 (50 mg, 0.076 mmol), triethylsilane (120 µL, 0.75 mmol), trifluoroacetic acid (60 µL, 0.78 mmol), and the compound from Reference Example 58 (80 mg, 0.38 mmol) in dichloromethane (0.5 mL) was stirred at room temperature for 4 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 42 mg (65%) of the title compound. MS 854 (M+H)$^+$.

EXAMPLE 101

Compound 101 (Formula 1': R$_1$ is (2E)-3-(4-pyrazinylphenyl)-2-propenyl, R$_2$ is H, R$_3$ is H, R$_4$ is F)

A solution of the compound from example 2 (50 mg, 0.076 mmol), triethylsilane (120 µL, 0.75 mmol), trifluoroacetic acid (60 µL, 0.78 mmol), and the compound from Reference Example 57 (80 mg, 0.38 mmol) in dichloromethane (0.5 mL) was stirred at room temperature for 4 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 26 mg (40%) of the title compound. MS 854 (M+H)$^+$.

EXAMPLE 102

Compound 102 (Formula 1': R$_1$ is [4-(4-pyrimidinyl)phenylmethyl, R$_2$ is H, R$_3$ is H, R$_4$ is F)

A solution of the compound from example 2 (60 mg, 0.091 mmol), triethylsilane (120 µL, 0.75 mmol), trifluoroacetic acid (60 µL, 0.78 mmol), and the compound from Reference Example 18 (84 mg, 0.45 mmol) in dichloromethane (0.6 mL) was stirred at room temperature for 24 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 26 mg (35%) of the title compound. MS 828 (M+H)$^+$.

EXAMPLE 103

Compound 103 (Formula 1': R$_1$ is (2E)-3-[1-(2-pyrimidinyl)-1H-imidazol-4-yl]-2-propenyl, R$_2$ is H, R$_3$ is H, R$_4$ is F)

A solution of the compound from example 2 (50 mg, 0.076 mmol), triethylsilane (120 µL, 0.75 mmol), trifluoroacetic acid (60 µL, 0.78 mmol), and the compound from Reference Example 62 (77 mg, 0.45 mmol) in dichloromethane (0.5 mL) was stirred at room temperature for 5 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 24 mg (38%) of the title compound. MS 844 (M+H)$^+$.

EXAMPLE 104

Compound 104 (Formula 1': R$_1$ is [4-(2-pyridinyl)phenyl]methyl, R$_2$ is H, R$_3$ is H, R$_4$ is F)

A solution of the compound from example 2 (50 mg, 0.076 mmol), triethylsilane (120 µL, 0.75 mmol), trifluoroacetic acid (60 μL, 0.78 mmol), the compound from Reference Example 32 (80 mg, 0.38 mmol) in dichloromethane (0.5 mL) was stirred at room temperature for 4 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 46 mg (73%) of the title compound. MS 853 (M+H)$^+$.

EXAMPLE 105

Alternate Preparation of Compound 100

Step A

The compound of Example 73 (Compound 76) (38 mg, 0.045 mmol) was converted to its 2'-acetate derivative by a procedure analogous to Example 1, step D.

Step B

Sodium hexamethyldisilazide (1.0M in THF, 68 μL, 0.068 mmol) mmol) was added dropwise to a solution of the product from step A (0.045 mmol) in DMF (1 mL) at −60° C. The mixture was stirred for 20 min at −60° C. and then SELECTFLUOR™ (19 mg, 0.054 mmol) was added. The resulting mixture was stirred for 10 min at −60° C., diluted with ethyl acetate, washed with water and brine, dried (MgSO$_4$), and concentrated. This material was allowed to stand in methanol for 24 h and then concentrated. Purification by chromatography (SiO$_2$, 95:5:0.1 dichloromethane/methanol/conc. NH$_4$OH) yielded 22 mg (56%) of the title compound. MS 854 (M+H)$^+$.

EXAMPLE 106

Alternate Preparation of Compound 58

Step A

A solution of the compound from example 1, step D (200 mg, 0.23 mmol), triethylsilane (190 μL, 1.19 mmol), trifluoroacetic acid (100 μL, 1.30 mmol), and the compound from Reference Example 50 (244 mg, 1.23 mmol) in CH$_3$CN (1.5 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 94:6:0.1 dichloromethane/methanol/conc. NH$_4$OH) yielded 101 mg (50%) of the title compound. MS 886 (M+H)$^+$.

Step B

EDCI (104 mg, 0.54 mmol) was added to a solution of the compound from step A (67.5 mg, 0.076 mmol) and dimethyl sulfoxide (0.10 mL, 1.36 mmol) in dichloromethane (1 ml) at 0° C. A solution of pyridinium trifluoroacetate (106 mg, 0.54 mmol) in dichloromethane (1 mL) was added dropwise and the resulting solution was stirred at 0° C. for 2 h before being quenched with water (1 mL). After 5 min, the mixture is diluted with dichloromethane (20 mL), washed with water and brine, dried (MgSO$_4$), and concentrated. This material was allowed to stand in methanol for 24 h and then concentrated. Purification by chromatography (SiO$_2$, 94:6:0.1 dichloromethane/methanol/conc. NH$_4$OH) yielded 53 mg (83%) of the title compound. MS 842 (M+H)$^+$.

EXAMPLE 107

Alternate Preparation of the Compound 32

The title compound was prepared by procedures analogous to Example 106 (alternate preparation) by substituting the compound of Reference Example 29 for the compound of Reference Example 50.

EXAMPLE 108

Compound 95

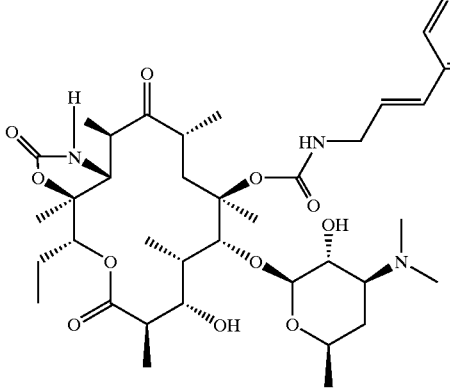

Step A:

A solution of the compound from example 1, step E (1.00 g, 1.46 mmol), triethylsilane (1.20 mL, 7.51 mmol), trifluoroacetic acid (0.55 mL, 7.14 mmol), and the compound from Reference Example 29 (1.30 g, 6.18 mmol) in CH$_3$CN (8 mL) was heated at 60° C. for 29 h. The reaction mixture was diluted with sat. aq. NaHCO$_3$ (10 mL), extracted with ethyl acetate (2×50 mL), dried (MgSO$_4$), and concentrated. Purification by chromatography (SiO$_2$, 3–5% methanol/dichloromethane containing 0.3% conc. NH$_4$OH) yielded 0.85 g (66%) of the title compound. MS 880 (M+H)$^+$.

Step B:

The product from step A (23 mg, 0.026 mmol) was allowed to stand in methanol (2 mL) for 21 h and then concentrated. Purification by chromatography (SiO$_2$, 5–10% methanol/dichloromethane containing 0.3% conc. NH$_4$OH) yielded 20 mg (91%) of the title compound. MS 838 (M+H)$^+$.

EXAMPLE 109

Compound 105 (Formula 1": R$_1$ is H, R$_2$ is H, R$_3$ is H, R$_4$ is F)

Sodium hydride (60% in mineral oil, 120 mg, 3.00 mmol) was added to a solution of the compound from Example 1, step f (1.00 g, 1.51 mmol) in DMF (10 mL) at 0° C. After 30 min at 0° C., N-fluorobenzenesulfonimide (570 mg, 1.81 mmol) was added and the mixture was stirred at 0° C. for 2 h. The reaction mixture was diluted with ethyl acetate (100 mL), washed with sat. aq. NaHCO$_3$ (100 mL), water (2×100 mL) and brine (100 mL), dried (Na$_2$SO$_4$), and concentrated. This material was allowed to stand in methanol for 18 h and then concentrated. Purification by chromatography (SiO$_2$, 96:4:0.2 dichloromethane/methanol/conc. NH$_4$OH) yielded 182 mg (18%) of the title compound. MS 660 (M+H)$^+$.

EXAMPLE 110

Compound 107 (Formula 1': R$_1$ is, [2-[[4-(2-pyrimidinyl)phenyl]methoxy]ethyl], R$_2$ is H, R$_3$ is H, R$_4$ is H)

A solution of the compound from example 1, step G (50 mg, 0.078 mmol), triethylsilane (120 μL, 0.75 mmol), trifluoroacetic acid (60 µL, 0.78 mmol), and the compound from Reference Example 63 (89 mg, 0.39 mmol) in CH$_3$CN (0.5 mL) was stirred at room temperature for 24 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 22 mg (33%) of the title compound. MS 854 (M+H)$^+$.

EXAMPLE 111

Compound 108 (Formula 1': R$_1$ is, [2-[[4-(2-pyrimidinyl)phenyl]methoxy]ethyl], R$_2$ is H, R$_3$ is H, R$_4$ is F)

A solution of the compound from example 2 (50 mg, 0.076 mmol), triethylsilane (120 µL, 0.75 mmol), trifluoroacetic acid (60 µL, 0.78 mmol), and the compound from Reference Example 63 (87 mg, 0.38 mmol) in CH$_3$CN (0.5 mL) was stirred at room temperature for 4 h. The reaction mixture was diluted with ethyl acetate (30 mL), washed with sat. aq. NaHCO$_3$ (10 mL) and brine (10 mL), dried (Na$_2$SO$_4$), and concentrated. Purification by chromatography (SiO$_2$, 95:5:0.1 dichloromethane/methanol/conc. NH$_4$OH) yielded 50 mg (66%) of the title compound. MS 872 (M+H)$^+$.

EXAMPLE 112

Compound 109 (Formula 1': R$_1$ is 2-(1,3-dihydro-1,3-dioxo-2H-isoindol-2-yl)ethyl, R$_2$ is H, R$_3$ is H, R$_4$ is H)

A solution of the compound from example 1, step G (400 mg, 0.62 mmol), triethylsilane (960 µL, 5.9 mmol), trifluoroacetic acid (480 µL, 5.9 mmol), and the compound from Reference Example 64 (350 mg, 1.86 mmol) in CH$_3$CN (4.0 mL) was stirred at room temperature for 24 h. Additional compound from Reference Example 64 (100 mg), trifluoroacetic acid (120 µL) and triethylsilane (240 µL) were added and the reaction mixture was heated to 60° C. for 48 h. The reaction mixture was diluted with ethyl acetate (60 mL), washed with sat. aq. NaHCO$_3$ (20 mL) and brine (20 mL), dried (Na$_2$SO$_4$), and concentrated. Purification by chromatography (SiO$_2$, 96:4:0.1 dichloromethane/methanol/conc. NH$_4$OH) yielded 300 mg (59%) of the title compound. MS 815 (M+H)+.

EXAMPLE 113

Compound 110 (Formula 1': R$_1$ is 2-aminoethyl, R$_2$ is H, R$_3$ is H, R$_4$ is H)

A solution of the compound from example 112 (300 mg, 0.37 mmol) and hydrazine (25 µL, 0.81 mmol) in ethanol (6 mL) was heated to reflux for 6 h. The reaction mixture was cooled to room temperature and solvent was evaporated. The residue was diluted with dichloromethane (40 mL), washed with sat. aq. NaHCO$_3$ (20 mL) and brine (20 mL), dried (MgSO$_4$), and concentrated. Purification by chromatography (SiO$_2$, 95:5:0.1 dichloromethane/methanol/conc. NH$_4$OH) yielded 110 mg (44%) of the title compound. MS 685 (M+H)+.

EXAMPLE 114

Compound 111 (Formula 1': R$_1$ is 2-[([1,1'-biphenyl]-4-ylcarbonyl)amino]ethyl, R$_2$ is H, R$_3$ is H, R$_4$ is H)

A solution of the compound from example 113 (30 mg, 0.044 mmol), 4-biphenylcarbonyl chloride (21 mg, 0.097 mmol) and triethylamine (14 µL, 0.097 mmol) in dichloromethane (1 mL) was stirred at room temperature for 6 h. The reaction mixture was diluted with dichloromethane (15 mL), washed with sat. aq. NaHCO$_3$ (10 mL), water (10 mL) and brine (10 mL). The organic layer was dried (MgSO$_4$) and evaporated.

The crude product was dissolved in methanol (5 mL) and heated to 60° C. for 3 h. The reaction mixture was concentrated. Purification by chromatography (SiO$_2$, 96:4:0.1 dichloromethane/methanol/conc. NH$_4$OH) yielded 20 mg (53%) of the title compound. MS 865 (M+H)+.

EXAMPLE 115

Compound 112 (Formula 1': R$_1$ is 2-[(3-pyridinylcarbonyl)amino]ethyl, R$_2$ is H, R$_3$ is H, R$_4$ is H)

A solution of the compound from example 113 (30 mg, 0.044 mmol), nicotinoyl chloride hydrochloride (17 mg, 0.097 mmol) and triethylamine (14 µL, 0.097 mmol) in dichloromethane (1 mL) was stirred at room temperature for 1 h. The reaction mixture was diluted with dichloromethane (15 mL), washed with sat. aq. NaHCO$_3$ (10 mL), water (10 mL) and brine (10 mL). The organic layer was dried (MgSO$_4$) and evaporated.

The crude product was dissolved in methanol (5 mL) and heated to 60° C. for 3 h. The reaction mixture was concentrated. Purification by chromatography (SiO$_2$, 96:4:0.1 dichloromethane/methanol/conc. NH$_4$OH) yielded 21 mg (62%) of the title compound. MS 790 (M+H)$^+$.

EXAMPLE 116

Compound 113 (Formula 1': R$_1$ is 2-[(3-quinolinylcarbonyl)amino]ethyl, R$_2$ is H, R$_3$ is H, R$_4$'is H)

A solution of the compound from example 113 (30 mg, 0.044 mmol), 3-quinolinecarbonyl chloride (19 mg, 0.097 mmol) and triethylamine (14 µL, 0.097 mmol) in dichloromethane (1 mL) was stirred at room temperature for 6 h. The reaction mixture was diluted with dichloromethane (15 mL), washed with sat. aq. NaHCO$_3$ (10 mL), water (10 mL) and brine (10 mL). The organic layer was dried (MgSO$_4$) and evaporated.

The crude product was dissolved in methanol (5 mL) and heated to 60° C for 3 h. The reaction mixture was concentrated. Purification by chromatography (SiO$_2$, 96:4:0.1 dichloromethane/methanol/conc. NH$_4$OH) yielded 23 mg (62%) of the title compound. MS 840 (M+H)$^+$.

EXAMPLE 117

Compound 114 (Formula 1': R$_1$ is 2-[(3-quinolinylmethyl)amino]ethyl, R$_2$ is H, R$_3$ is H, R$_4$ is H)

To a solution of the compound from example 113 (30 mg, 0.044 mmol), 3-quinolinecarboxaldehyde (42 mg, 0.26 mmol) and acetic acid (25 µL, 0.44 mmol) in methanol (2 mL) was added NaCNBH$_3$ (6 mg, 0.088 mmol). The reaction mixture was stirred at room temperature for 10 min. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 24 mg (67%) of the title compound. MS 826 (M+H)$^+$.

EXAMPLE 118

Compound 115 (Formula 1': $R_1$ is 2-[[[4-(2-pyrimidinyl)phenyl]methyl]amino]ethyl, $R_2$ is H, $R_3$ is H, $R_4$ is H)

To a solution of the compound from example 113 (30 mg, 0.044 mmol), the compound from Reference Example 29 (24 mg, 0.13 mmol) and acetic acid (25 µL, 0.44 mmol) in methanol (2 mL) was added NaCNBH$_3$ (6 mg, 0.088 mmol). The reaction mixture was stirred at room temperature for 1 h. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 25 mg (68%) of the title compound. MS 853 (M+H)$^+$.

EXAMPLE 119

Compound 116 (Formula 1': $R_1$ is 2-[(3-pyridylmethyl)amino]ethyl, $R_2$ is H, $R_3$ is H, $R_4$ is H)

To a solution of the compound from example 113 (30 mg, 0.044 mmol), 3-pyridinecarboxaldehyde (14 mg, 0.13 mmol) and acetic acid (25 µL, 0.44 mmol) in methanol (2 mL) was added NaCNBH$_3$ (6 mg, 0.088 mmol). The reaction mixture was stirred at room temperature overnight. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 23 mg (68%) of the title compound. MS 776 (M+H)$^+$.

EXAMPLE 120

Compound 117 (Formula 1': $R_1$ is 2-[methyl[[4-(2-pyrimidinyl)phenyl]methyl]amino]ethyl, $R_2$ is H, $R_3$ is H, $R_4$ is H)

To a solution of the compound from example 118 (18 mg, 0.021 mmol), paraformaldehyde (4 mg, 0.13 mmol) and acetic acid (13 µL, 0.21 mmol) in methanol (1 mL) was added NaCNBH$_3$ (3 mg, 0.042 mmol). The reaction mixture was stirred at room temperature for 3 h. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 9 mg (50%) of the title compound. MS 867 (M+H)$^+$.

EXAMPLE 121

Compound 118 (Formula 1': $R_1$ is 2-[methyl(3-pyridylmethyl)amino]ethyl, $R_2$ is H, $R_3$ is H, $R_4$ is H)

To a solution of the compound from example 119 (13 mg, 0.019 mmol), paraformaldehyde (3.4 mg, 0.11 mmol) and acetic acid (12 µL, 0.19 mmol) in methanol (1 mL) was added NaCNBH$_3$ (2 mg, 0.038 mmol). The reaction mixture was stirred at room temperature for 12 h. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 6.5 mg (43%) of the title compound. MS 790 (M+H)$^+$.

EXAMPLE 122

Compound 119 (Formula 1': $R_1$ is 2-[methyl(3-quinolinylmethyl)amino]ethyl, $R_2$ is H, $R_3$ is H, $R_4$ is H)

To a solution of the compound from example 117 (9 mg, 0.011 mmol), paraformaldehyde (1 mg, 0.03 mmol) and acetic acid (7 µL, 0.11 mmol) in methanol (1 mL) was added NaCNBH$_3$ (1.4 mg, 0.022 mmol). The reaction mixture was stirred at room temperature for 12 h. Methanol was evaporated. The residue was diluted with EtOAc (15 mL), washed with sat. aq. NaHCO$_3$ (10 mL), water (10 mL) and brine (10 mL). The organic layer was dried (MgSO$_4$) and evaporated. Purification by chromatography (SiO$_2$, 96:4:0.1 dichloromethane/methanol/conc. NH$_4$OH) yielded 4.8 mg (52%) of the title compound. MS 840 (M+H)$^+$.

EXAMPLE 123

Compound 120 (Compound 1l' from Scheme 14)

50% aqueous hydroxylamine (3.0 g) was added to a stirred mixture of the compound from Example 1, Step C in isopropanol (7 mL). Acetic acid (1.3 mL) was added and the reaction mixture was refluxed for 36 h. The mixture was cooled to room temperature and isopropanol was evaporated. Sat. NaHCO$_3$ (30 mL) was added to the residue and the mixture was extracted with CH$_2$Cl$_2$ (3×75 mL). The combined organic extracts were washed with brine, dried (MgSO$_4$), and concentrated.

The above crude compound was dissolved in ethanol (10 mL) and 10% HCl (20 mL) and stirred at room temperature for 2 h. The mixture was made basic with 10% NaOH, and extracted with CH$_2$Cl$_2$ (3×75 mL). The combined organic layers were washed with water and brine, dried (MgSO$_4$) and concentrated. Purification by chromatography (SiO$_2$, 94:6:0.5 dichloromethane/methanol/conc. NH$_4$OH) yielded 508 mg (22%) of the desired compound. MS 659 (M+H)$^+$.

EXAMPLE 124

Compound 121 (Compound 1m' from Scheme 14)

A solution of the compound from example 123 (500 mg, 0.76 mmol), triethylamine (233 µL, 1.52 mmol), and acetic anhydride (158 µL, 1.52 mmol) in CH$_2$Cl$_2$ (10 mL) was stirred at room temperature for 24 h. The solution was diluted with CH$_2$Cl$_2$ (20 mL) and washed with sat. NaHCO$_3$ and brine. The organic layer was dried and concentrated. The material was used without further purification.

EDCI (0.65 g, 3.23 mmol) was added to a solution of the above compound (340 mg, 0.46 mmol) and DMSO (0.62 mL, 8.74 mmol) in dichloromethane (2 mL) at 0° C. A solution of pyridinium trifluoroacatate (0.65 g, 3.37 mmol) in dichloromethane (2 mL) was added dropwise and the resulting solution was stirred at room temperature for 2 h. The mixture was diluted with dichloromethane (30 mL), washed with water and brine, dried and concentrated. Purification by chromatography (SiO$_2$, 98:2:0.5 dichloromethane/methanol/conc. NH$_4$OH) yielded 310 mg (55%) of the desired compound. MS 741 (M+H)$^+$.

EXAMPLE 125

Compound 122 (Compound 1n' from Scheme 14)

Sodium hexamethyidisilazide (1.0 M in THF, 200 µL, 0.2 mmol) was added dropwise to a solution of the product from example 124 (98 mg, 0.13 mmol) in DMF (3 mL) at −60° C. The mixture was stirred for 20 min and then SELECT-FLUOR™ (60 mg, 0.16 mmol) was added. The reaction mixture was slowly warm up to 10° C. (about 1.5 h), diluted with EtOAc, washed with water and brine, dried and concentrated. This material was directly used in the next step without further purification. MS 759 (M+H)$^+$.

EXAMPLE 126

Compound 123 (Compound of Formula 1r' from Scheme 14: RCH$_2$— is (2E)-3-[4-(2-pyrimidinyl)phenyl]-2-propenyl)

A solution of the compound from Example 125 (50 mg, 0.066 mmol), triethylsilane (120 μL, 0.75 mmol), trifluoroacetic acid (60 μL, 0.75 mmol), and the compound from Reference Example 29 (69 mg, 0.33 mmol) in CH$_3$CN (0.5 mL) was heated at 60° C. for 12 h. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 35 mg (61%) of the desired compound. MS 869 (M+H)$^+$.

EXAMPLE 127

Compound 124 (Compound of Formula 1r' from Scheme 14: RCH$_2$— is (2E)-3-[1-(2-pyrimidinyl)-1H-imidazol-4-yl]-2-propenyl)

A solution of the compound from Example 125 (35 mg, 0.046 mmol), triethylsilane (42 μL, 0.26 mmol), trifluoroacetic acid (42 μL, 0.53 mmol), and the compound from Reference Example 62 (46 mg, 0.23 mmol) in CH$_3$CN (0.5 mL) was heated at 60° C. for 24 h. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 6.2 mg (16%) of the desired compound. MS 859 (M+H)$^+$.

EXAMPLE 128

Compound 125 (Compound of Formula 1r' from Scheme 14: RCH$_2$— is (2E)-3-[4-(3-pyridazinyl)phenyl]-2-propenyl)

A solution of the compound from Example 125 (30 mg, 0.04 mmol), triethylsilane (80 μL, 0.5 mmol), trifluoroacetic acid (40 μL, 0.5 mmol), and the compound from Reference Example 61 (42 mg, 0.20 mmol) in CH$_3$CN (0.5 mL) was heated at 60° C. overnight. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 17 mg (49%) of the desired compound. MS 869 (M+H)$^+$.

EXAMPLE 129

Compound 126 (Compound of Formula 1r' from Scheme 14: RCH$_2$— is [4-(2-pyrimidinyloxy)phenyl]methyl)

A solution of the compound from Example 125 (30 mg, 0.04 mmol), triethylsilane (80 μL, 0.5 mmol), trifluoroacetic acid (40 μL, 0.5 mmol), and the compound from Reference Example 9 (45 mg, 0.20 mmol) in CH$_3$CN (0.5 mL) was stirred at room temperature for 24 h. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 16 mg (46%) of the desired compound. MS 887 (M+H)$^+$.

EXAMPLE 130

Compound 127 (Compound of Formula 1r' from Scheme 14: RCH$_2$— is (2E)-3-(3-quinolinyl)-2-propenyl)

A solution of the compound from Example 125 (30 mg, 0.04 mmol), triethylsilane (80 μL, 0.5 mmol), trifluoroacetic acid (40 μL, 0.5 mmol), and the compound from Reference Example 69 (37 mg, 0.20 mmol) in CH$_3$CN (0.5 mL) was heated at 60° C. overnight. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 17 mg (52%) of the desired compound. MS 842 (M+H)$^+$.

EXAMPLE 131

Compound 128 (Compound of Formula 1r' from Scheme 14: RCH$_2$— is [4-(2-pyrimidinyl)phenyl]methyl)

A solution of the compound from Example 125 (30 mg, 0.04 mmol), triethylsilane (80 μL, 0.5 mmol), trifluoroacetic acid (40 μL, 0.5 mmol), and 4-(2-pyrimidinyl)-benzaldehyde (37 mg, 0.20 mmol) in CH$_3$CN (0.5 mL) was heated at 60° C. for 24 h. The reaction mixture was diluted with ethyl acetate (15 mL), washed with water and brine, dried and concentrated.

To the above crude product in methanol (5 mL) was added sat. NaHCO$_3$ (0.5 mL). The mixture was stirred overnight at room temperature. The reaction mixture was concentrated, diluted with methylene chloride, washed with water and brine, dried and concentrated. Purification by chromatography (SiO$_2$, 95:5:0.5 dichloromethane/methanol/conc. NH$_4$OH) yielded 6 mg (18%) of the desired compound. MS 843 (M+H)$^+$.

EXAMPLE 132

Compound 129 (Compound of Formula 1r' from Scheme 14: $RCH_2$— is (2E)-3-phenyl-2-propenyl)

A solution of the compound from Example 125 (30 mg, 0.04 mmol), triethylsilane (80 µL, 0.5 mmol), trifluoroacetic acid (40 µL, 0.5 mmol), and cinnamaldehyde (27 mg, 0.20 mmol) in $CH_3CN$ (0.5 mL) was heated at 60° C. for 18 h. The reaction mixture was diluted with ethyl acetate (15 mL), washed with water and brine, dried and concentrated.

To the above crude product in methanol (5 mL) was added sat. $NaHCO_3$ (0.5 mL). The mixture was stirred overnight at room temperature. The reaction mixture was concentrated, diluted with methylene chloride, washed with water and brine, dried and concentrated. Purification by chromatography ($SiO_2$, 95:5:0.5 dichloromethane/methanol/conc. $NH_4OH$) yielded 8 mg (26%) of the desired compound. MS 791 $(M+H)^+$.

EXAMPLE 133

Compound 130 (Compound of Formula 1r' from Scheme 14: $RCH_2$— is (2E)-4-(2-bromopyridinyl)-2-propenyl)

A solution of the compound from Example 125 (30 mg, 0.04 mmol), triethylsilane (80 µL, 0.5 mmol), trifluoroacetic acid (40 µL, 0.5 mmol), and the compound from Reference Example 23 (45 mg, 0.20 mmol) in $CH_3CN$ (0.5 mL) was heated at 60° C. for 24 h. The reaction mixture was diluted with ethyl acetate (15 mL), washed with water and brine, dried and concentrated.

To the above crude product in methanol (5 mL) was added sat. $NaHCO_3$ (0.5 mL). The mixture was stirred overnight at room temperature. The reaction mixture was concentrated, diluted with methylene chloride, washed with water and brine, dried and concentrated. Purification by chromatography ($SiO_2$, 95:5:0.5 dichloromethane/methanol/conc. $NH_4OH$) yielded 16 mg (34%) of the desired compound. MS 870 $(M+H)^+$.

EXAMPLE 134

Compound 131 (Compound of Formula 1p' from Scheme 14: $RCH_2$— is (2E)-3-pyridinyl-2-propenyl)

A solution of the compound from Example 125 (30 mg, 0.04 mmol), triethylsilane (80 µL, 0.5 mmol), trifluoroacetic acid (40 µL, 0.5 mmol), and the compound from Reference Example 70 (27 mg, 0.20 mmol) in $CH_3CN$ (0.5 mL) was heated at 60° C. for 36 h. The reaction mixture was diluted with ethyl acetate (15 mL), washed with water and brine, dried and concentrated. Purification by chromatography ($SiO_2$, 95:5:0.5 dichloromethane/methanol/conc. $NH_4OH$) yielded 16 mg (46%) of the desired compound. MS 876 $(M+H)^+$.

EXAMPLE 135

Compound 132 (Compound of Formula 1r' from Scheme 14: $RCH_2$— is (2E)-3-pyridinyl-2-propenyl)

The compound from Example 134 (8 mg) was dissolved in methanol (2 mL). The reaction mixture was heated at 60° C. for 2 h. Methanol was concentrated to give the desired product (7 mg). MS 792 $(M+H)^+$.

EXAMPLE 136

Compound 133 (Compound of Formula 1q' from Scheme 14: $RCH_2$— is (2E)-3-[4-(2-pyrimidinyl)phenyl]-2-propenyl)

A solution of the compound from Example 124 (37 mg, 0.05 mmol), triethylsilane (80 µL, 0.5 mmol), trifluoroacetic acid (40 µL, 0.5 mmol), and the compound from the Reference Example 29 (53 mg, 0.25 mmol) in $CH_3CN$ (1 mL) was heated at 60° C. for 24 h. The reaction mixture was diluted with ethyl acetate (15 mL), washed with water and brine, dried and concentrated.

To the above crude product in methanol (5 mL) was added sat. $NaHCO_3$ (0.5 mL). The mixture was stirred overnight at room temperature. The reaction mixture was concentrated, diluted with methylene chloride, washed with water and brine, dried and concentrated. Purification by chromatography ($SiO_2$, 95:5:0.5 dichloromethane/methanol/conc. $NH_4OH$) yielded 36 mg (86%) of the desired compound. MS 852 $(M+H)^+$.

EXAMPLE 137

Compound 134 (Compound of Formula 1s' from Scheme 15: $RCH_2$— is (2E)-3-[4-(2-pyrimidinyl)phenyl]-2-propenyl)

50% aqueous methoxylamine (0.24 ml, 1.2 mmol) was added to a stirred mixture of the compound from Example 75 (200 mg, 0.24 mmol) in ethanol (2 mL). The reaction mixture was refluxed for 48 h. The mixture was cooled to room temperature and ethanol was evaporated. Sat. $NaHCO_3$ (10 mL) was added to the residue and the mixture was extracted with $CH_2Cl_2$ (3×10 mL). The combined organic extracts were washed with brine, dried ($MgSO_4$), and concentrated. The desired compound was obtained by HPLC separation. MS 894 $(M+H)^+$.

EXAMPLE 138

Compound 135 (Formula 1': $R_1$ is [3-[4-(2-pyrimidinyl)phenyl]cyclobutyl]methyl, $R_2$ is H, $R_3$ is H, $R_4$ is H)

A solution of the compound from Reference Example 67 (20 mg, 0.028 mmol) and the compound from Reference Example 71 (8 mg, 0.033 mmol) in DMSO (0.2 mL) was stirred at room temperature overnight. The mixture was diluted with ethyl acetate, washed with water and brine, dried and concentrated. Purification by chromatography ($SiO_2$, 95:5:0.5 dichloromethane/methanol/conc. $NH_4OH$) yielded 8.0 mg (33%) of the title compound. MS 864 $(M+H)^+$.

EXAMPLE 139

Compound 136 (Formula 1': $R_1$ is 3-[4-(2-pyrimidinyl)phenyl]cyclobutyl, $R_2$ is H, $R_3$ is H, $R_4$ is H)

A solution of the compound from Example 67 (26 mg, 0.037 mmol) and the compound from Reference Example 72 (10 mg, 0.044 mmol) in DMSO (0.3 mL) was stirred at room temperature overnight. The mixture was diluted with ethyl acetate, washed with water and brine, dried and concentrated. Purification by chromatography ($SiO_2$, 95:5:0.5 dichloromethane/methanol/conc. $NH_4OH$) yielded 5.3 mg (18%) of the title compound. MS 850 $(M+H)^+$.

EXAMPLE 140

Compound 137 (Formula 1': $NR_1R_2$ is 1-(4-phenylpiperidinyl), $R_3$ is H, $R_4$ is H)

A solution of the compound from example 1, step G (50 mg, 0.078 mmol), triethylsilane (125 µL, 0.78 mmol), trifluoroacetic acid (60 μL, 0.78 mmol), and the compound from Reference Example 66 (90 mg, 0.39 mmol) in $CH_3CN$ (0.5 mL) was stirred at room temperature for 40 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.2 dichloromethane/methanol/conc. $NH_4OH$) yielded 17 mg (28%) of the title compound. MS 786 $(M+H)^+$.

EXAMPLE 141

Compound 138 (Formula 1': $NR_1R_2$ is 1.3-dihydro-2H-isoindol-2-yl, $R_3$ is H, $R_4$ is H)

A solution of the compound from example 1, step G (100 mg, 0.16 mmol), triethylsilane (250 μL, 1.57 mmol), trifluoroacetic acid (120 μL, 0.78 mmol), and phthalaldehyde (105 mg, 0.78 mmol) in $CH_3CN$ (0.5 mL) was stirred at room temperature for 4 h. The reaction mixture was diluted with ethyl acetate (30 mL), washed with sat. aq. $NaHCO_3$ (10 mL) and brine (10 mL), dried ($Na_2SO_4$), and concentrated. Purification by chromatography ($SiO_2$, 96:4:0.2 dichloromethane/methanol/conc. $NH_4OH$) followed by HPLC (C18 column, 30–50% $CH_3CN/H_2O$+0.1% TFA) yielded 12 mg (10%) of the title compound. MS 744 $(M+H)^+$.

Reference Example 1
Preparation of 4-phenylbutanal

4-Phenylbutanol (700 mg, 4.66 mmol) was added to a solution of the Dess-Martin reagent (2.40 g, 5.66 mol) in dichloromethane (35 mL). After 30 min at RT, the solution was quenched with 10% aq. $Na_2S_2O_3$, washed with sat. aq. $NaHCO_3$ and brine, dried ($Na_2SO_4$), and concentrated. Purification by chromatography ($SiO_2$, 9:1 hexane/ethyl acetate) yielded the title compound. MS 149 $(M+H)^+$.

Reference Example 2
Preparation of 4-pyridinepropanal 4-pyridinepropanol (0.60 mL, 4.65 mmol) was added to a solution of the Dess-Martin reagent (2.37 g, 5.58 mol) in dichloromethane (30 mL). After 60 min at RT, the solution was quenched with 10% aq. $Na_2S_2O_3$, washed with sat. aq. $NaHCO_3$ and brine, dried ($Na_2SO_4$), and concentrated. Purification by chromatography ($SiO_2$, 4:1 hexane/ethyl acetate) yielded the title compound. MS 136 $(M+H)^+$.

Reference Example 3
3-(1H-pyrazol-1-yl)benzaldehyde

A mixture of 3-formylphenylboronic acid (2.00 g, 13.34 mmol), pyrazole (0.46 g, 6.67 mmol), copper(II) acetate (1.82 g, 10.01 mmol), pyridine (1.10 mL, 13.34 mmol), and powdered 4A molecular sieves (2.5 g) in dichloromethane (20 mL) was stirred under an air atmosphere for 24 h. The mixture was then filtered through Celite, the filtered solids were washed with MeOH, and the combined filtrate was concentrated. Purification by chromatography ($SiO_2$, 3:1 hexane/ethyl acetate) yielded the title compound. MS 173 $(M+H)^+$.

Reference Example 4
4-(4-methyl-1H-pyrazol-1-yl)benzaldehyde

A solution of 4-methylpyrazole (1.98 g, 24.11 mmol) in DMF (8 mL) was added to sodium hydride (60% in oil, 0.97 g, 24.25 mmol) in DMF (6 mL) and the resulting mixture was stirred 2 h at RT. 4-Fluorobenzaldehyde (1.26 g, 7.45 mmol) was added dropwise and the resulting mixture heated to 80° C. for 3 h. The reaction mixture was poured into ice-water and extracted with ethyl acetate. The combined organic layers were washed with water and brine, dried ($MgSO_4$), and concentrated. Purification by chromatography ($SiO_2$, 4:1 hexane/ethyl acetate) followed by recrystallization from hexane yielded the title compound. MS 187 $(M+H)^+$.

Reference Example 5
3-Methoxy-4-(1H-pyrazol-1-yl)benzaldehyde

A mixture of 4-fluoro-3-methoxybenzaldehyde (2.00 g, 12.98 mmol), pyrazole (1.32 g, 19.39 mmol), and powdered $K_2CO_3$ (2.68 g, 19.39 mmol) in DMF (20 mL) was heated to 120° C. for 20 h. The cooled reaction mixture was diluted with ethyl acetate (200 mL), washed with water (3×200 mL), dried ($Na_2SO_4$), and concentrated. Purification by chromatography ($SiO_2$, 4:1 hexane/ethyl acetate) yielded 1.52 g (58%) of the title compound as a yellow oil. MS 203 $(M+H)^+$.

Reference Example 6
3-Fluoro-4-(1H-pyrazol-1-yl)benzaldehyde

The title compound was prepared by a procedure analogous to Reference Example 5 by substituting 3,4-difluorobenzaldehyde for the 4-fluoro-3-methoxybenzaldehyde of Reference Example 5. MS 191 $(M+H)^+$.

Reference Example 7
3-Fluoro-4-(1H-1,2,4-triazol-1-yl)benzaldehyde

The title compound was prepared by a procedure analogous to Reference Example 5 by substituting 3,4-difluorobenzaldehyde and 1,2,4-triazole, respectively, for the 4-fluoro-3-methoxybenzaldehyde and pyrazole of Reference Example 5. MS 192 $(M+H)^+$.

Reference Example 8
2-Fluoro-4-(1H-pyrazol-1-yl)benzaldehyde
Step A: 2-Fluoro-4-(1H-pyrazol-1-yl)benzonitrile A mixture of 2-fluoro-4-hydrazinobenzonitrile (3.03 g, 20.05 mmol, prepared as described in U.S. Pat. No. 5,006, 148), malonaldehyde bis(diethyl)acetal (4.80 mL, 20.02 mmol), and conc. HCl (1 mL) in ethanol (20 mL) was heated to reflux for 1 h. Upon cooling to RT, the reaction mixture solidified. Water (40 mL) was added and the mixture was cooled to 0° C. and made basic with 10% NaOH. The solids were removed by filtration, washed with water, and dried in vacuo to yield 3.59 g (96%) of the title compound as a light brown solid.

Step B: 2-Fluoro-4-(1H-pyrazol-1-yl)benzaldehyde

Diisobutylaluminum hydride (1.0 M in toluene, 11.00 mL, 11.00 mol) was added dropwise over 10 min to a vigorously stirred suspension of the compound from step A (1.88 g, 10.04 mmol) in toluene (100 mL) at −78° C. After 1 h at −78° C., MeOH (1 mL) was added, the mixture was stirred for 5 min, and then poured into a stirred, cold (0° C.) mixture of 1.2 N HCl (100 mL) and ethyl acetate (100 mL). After stirring for 30 min at RT, the layers were separated and the aqueous layer was extracted with additional ethyl acetate (100 mL). The combined organic layers were washed with sat. aq. $NaHCO_3$ (100 mL) and brine (100 mL), dried ($MgSO_4$), and concentrated. Recrystallization from IPA followed by chromatography ($SiO_2$, dichloromethane) provided 1.25 g (65%) of the title compound as a colorless solid. MS 191 $(M+H)^+$.

Reference Example 9
4-(2-pyrimidinyloxy)benzaldehyde

Sodium hydride (60% in oil, 1.44 g, 36.00 mmol) was added to a 0° C. solution of 4-hydroxybenzaldehyde (4.40 g, 36.03 mmol) in DMF (16 mL). After stirring for 20 min at 0° C., the mixture was allowed to warm to RT and a solution of 2-chloropyrimidine (4.12 g, 35.97 mmol) in DMF (8 mL) was added. The resulting mixture was heated to 100° C. for 18 h. The solvent was evaporated, the residue was dissolved in ethyl acetate, washed with water and brine, dried ($MgSO_4$), and concentrated to provide 6.20 g (86%) of the title compound. MS 201 $(M+H)^+$.

Reference Example 10
1-(2-pyrimidinyl)-1H-imidazole-4-carboxaldehyde

The title compound was prepared by a procedure analogous to Reference Example 9 by substituting 1H-imidazole-4-carboxaldehyde for the 4-hydroxybenzaldehyde of Reference Example 9. MS 175 $(M+H)^+$.

Reference Example 11
3-(2-pyridinyl)benzaldehyde 2M aq. $Na_2CO_3$ (5 mL) and a solution of 3-formylphenylboronic acid (1.14 g, 7.60 mmol) in methanol (5 mL) were added to a solution of 2-bromopyridine (1.00 g, 6.33 mmol) and tetrakis(triphenylphosphine)palladium(0) (0.22 g, 0.19 mmol) in toluene (10 mL) and the mixture was heated to reflux for 18 h. The cooled reaction mixture was diluted with dichloromethane, washed with sat. aq. $NaHCO_3$ and brine, dried ($MgSO_4$), and concentrated. Purification by chromatography ($SiO_2$, 4:1 hexane/ethyl acetate) yielded 1.03 g (89%) of the title compound. MS 184 $(M+H)^+$.

Reference Example 12
3-(2-pyrimidinyl)benzaldehyde

A mixture of $Na_2CO_3$ (4.74 g, 44.72 mmol) and 3-formylphenylboronic acid (3.40 g, 22.67 mmol) in water (15 mL) were added to a solution of 2-bromopyrimidine (3.00 g, 18.87 mmol) and tetrakis(triphenylphosphine)palladium(0) (0.72 g, 0.62 mmol) in DME (30 mL) and the mixture was heated to reflux for 24 h. The cooled reaction mixture was diluted with dichloromethane, washed with sat. aq. $NaHCO_3$ and brine, dried ($MgSO_4$), and concentrated. Purification by chromatography ($SiO_2$, 1:1 hexane/ethyl acetate) yielded 2.20 g (63%) of the title compound. MS 185 $(M+H)^+$.

Reference Example 13
4-(4-methoxy-2-pyrimidinyl)benzaldehyde

1 M aq. $Na_2CO_3$ (20 mL) and ethanol (10 mL) were added to a solution of 2-chloro-4-methoxypyrimidine (2.90 g, 20.06 mmol, prepared as described in *Tetrahedron* 1997, 53, 11595), 4-formylphenylboronic acid (3.90 g, 26.01 mmol) and [1,4-bis(diphenylphosphino)butane]palladium(II) dichloride (0.60 g, 0.99 mmol) in toluene (40 mL) and the mixture was heated to reflux for 18 h. The cooled reaction mixture was diluted with ethyl acetate, washed with sat. aq. $NaHCO_3$ and brine, dried ($MgSO_4$), and concentrated. Purification by chromatography ($SiO_2$, 4:1 hexane/ethyl acetate) yielded 1.80 g (42%) of the title compound. MS 215 $(M+H)^+$.

Reference Example 14
4-(4-methyl-2-pyrimidinyl)benzaldehyde

The title compound was prepared by a procedure analogous to Reference Example 12 by substituting 4-formylphenylboronic acid and 2-bromo-4-methylpyrimidine (prepared as described in *Helv. Chim. Acta* 1992, 75, 1621) for the 3-formylphenylboronic acid and 2-bromopyridine, respectively, of Reference Example 12. MS 199 $(M+H)^+$.

Reference Example 15
2-fluoro-4-(2-pyrimidinyl)benzaldehyde

Step A:

Dimethyl sulfoxide (70 mL) and 4-bromo-2-fluorobenzaldehyde (2.44 g, 12.02 mmol) were added to a mixture of potassium acetate (3.54 g, 36.07 mmol), bis(pinacolato)diboron (3.36 g, 13.23 mmol), and [1,1'-bis(diphenylphosphino)ferrocene]dichloropalladium(II) (294 mg, 0.36 mmol). The mixture was heated to 80° C. for 18 h. The cooled reaction mixture was diluted with benzene, washed with water, dried ($MgSO_4$), and concentrated. The material was used in the next step without further purification.

Step B:

The title compound was prepared by a procedure analogous to Reference Example 12 by substituting the product of step A for the 3-formylphenylboronic acid of Reference Example 12. MS 203 $(M+H)^+$.

Reference Example 16
4-(3-pyridazinyl)benzaldehyde

The title compound was prepared by a procedure analogous to Reference Example 13 by substituting 3-chloropyridazine (prepared as described in WO 9724124) for the 2-chloro-4-methoxypyrimidine of Reference Example 13. MS 185 $(M+H)^+$.

Reference Example 17
4-pyrazinylbenzaldehyde

The title compound was prepared by a procedure analogous to Reference Example 13 by substituting chloropyrazine for the 2-chloro-4-methoxypyrimidine of Reference Example 13. MS 185 $(M+H)^+$.

Reference Example 18
4-(4-pyrimidinyl)benzaldehyde

The title compound was prepared by a procedure analogous to Reference Example 13 by substituting 4-chloropyrimidine hydrochloride (prepared as described in WO 9821188) for the 2-chloro-4-methoxypyrimidine of Reference Example 13. MS 185 $(M+H)^+$.

Reference Example 19
4-(5-nitro-2-pyridinyl)benzaldehyde

The title compound was prepared by a procedure analogous to Reference Example 11 by substituting 4-formylphenylboronic acid and 2-bromo-5-nitropyridine for the 3-formylphenylboronic acid and 2-bromopyridine, respectively, of Reference Example 11. MS 229 $(M+H)^+$.

Reference Example 20
3-[4-(1H-pyrazol-1-yl)phenyl]-2-propynal

Step A: 3-[4-(1H-pyrazol-1-yl)phenyl]-2-propyn-1-ol

A mixture of 1-(4-bromophenyl)-1H-pyrazole (prepared as described in *Bull. Soc. Chim. Fr.* 1966, 2832) (2.24 g, 10.04 mmol), $Pd(Ph_3P)_2Cl_2$ (180 mg, 0.26 mmol), and copper(I) iodide (95 mg, 0.50 mmol) in TEA (20 mL) was stirred for 5 min, propargyl alcohol (0.70 mL, 12.02 mmol) was added, and the mixture was heated to 80° C. for 48 h. The volatiles were evaporated, ethyl acetate (50 mL) and water (50 mL) were added to the residue, and the mixture was filtered through a pad of Celite. The organic layer from the filtrate was washed with brine (50 mL), dried ($Na_2SO_4$), and concentrated. Purification by chromatography (SiO$_2$, 3:2 hexane/ethyl acetate) yielded 0.73 g (37%) of the title compound as a brown solid. MS 199 (M+H)$^+$.

Step B: 3-[4-(1H-pyrazol-1-yl)phenyl]-2-propynal

A mixture of the compound from step A (0.71 g, 3.58 mmol) and MnO$_2$ (3.10 g, 35.66 mmol) in acetone (40 mL) was heated to reflux for 3 h. The cooled reaction mixture was filtered through Celite and the filtrate was concentrated. Purification by chromatography (SiO$_2$, 6:1 hexane/ethyl acetate) yielded 0.19 g (27%) of the title compound as an off-white solid. MS 197 (M+H)$^+$.

Reference Example 21
3-(3-quinolinyl)-2-propynal

A mixture of 3-(3-quinolinyl)-2-propyn-1-ol (prepared as described in J. Med Chem. 1996, 39, 3179) (360 mg, 1.96 mmol) and the Dess-Martin reagent (1.00 g, 2.36 mmol) in dichloromethane (10 mL) was stirred at RT for 1.5 h. The solution was washed with sat. aq. NaHCO$_3$ and brine, dried (MgSO$_4$), and concentrated. Purification by chromatography (SiO$_2$, 1:4 hexane/ethyl acetate) yielded 258 mg (72%) of the title compound. MS 182 (M+H)$^+$.

Reference Example 22
3-[6-(1H-pyrazol-1-yl)-3-pyridinyl]-2-propenal
Step A: 5-Bromo-2-(1H-pyrazol-1-yl)pyridine Pyrazole (2.05 g, 30.11 mol) was added in portions to sodium hydride (60% in oil, 1.20 g, 30.00 mmol) in DMF (40 mL) and the resulting mixture was stirred for 1 h at RT. 2,5-Dibromopyridine (4.75 g, 20.05 mmol) was added and the mixture was heated to 100° C. for 2 h. Ice-water (100 mL) was added to the cooled reaction mixture and the precipitated solids were removed by filtration and allowed to air-dry. Recrystallization from hexane provided 3.31 g (74%) of the title compound as a tan solid. MS 224 (M+H)$^+$.

Step B: Methyl 3-([6-(1H-pyrazol-1-yl)pyridin-3-yl]-2-propenoate

A solution of the compound from step A (450 mg, 2.01 mmol) and tri(o-tolyl)phosphine (123 mg, 0.40 mmol) in DMF (8 mL) was cooled to 0° C. and purged with nitrogen for 15 min. TEA (0.56 mL, 4.02 mmol) and methyl acrylate (0.36 mL, 4.00 mmol) were added and purging was continued for 5 min. Palladium acetate (45 mg, 0.20 mmol) was added and the flask was stoppered and heated to 120° C. for 24 h. The cooled reaction mixture was diluted with ether (50 mL) and washed with water (2×25 mL) and brine (25 mL), dried (MgSO$_4$), and concentrated. Purification by chromatography (SiO$_2$, 4:1 hexane/ethyl acetate) yielded 356 mg (77%) of the title compound. MS 230 (M+H)$^+$.

Step C: 3-[6-(1H-pyrazol-1-yl)-3-pyridinyl]-2-propen-1-ol

DIBAL (1.0 M solution in toluene, 3.10 mL, 3.10 mmol) was added dropwise to a suspension of the compound from step B (350 mg, 1.53 mmol) in toluene (10 mL) and dichloromethane (4 mL) at −78° C. and the mixture was stirred for 2 h at that temperature. MeOH (1 mL) was added and the mixture was poured into a stirring mixture of ethyl acetate (20 mL) and 10% aq. potassium sodium tartrate (20 mL) and stirred for 1 h at RT. The organic layer was washed with brine (20 mL), dried (Na$_2$SO$_4$), and concentrated. Purification by chromatography (SiO$_2$, 1:1 hexane/ethyl acetate) yielded 185 mg (59%) of the title compound. MS 202 (M+H)$^+$.

Step D: 3-[6-(1H-pyrazol-1-yl)-3-pyridinyl]-2-propenal

A mixture of the compound from step C (185 mg, 0.92 mmol) and MnO$_2$ (1.60 g, 18.40 mmol) in acetone (15 mL) was heated to reflux for 1 h. The cooled reaction mixture was filtered through Celite and the filtrate was concentrated. Purification by chromatography (SiO$_2$, 2:1 hexane/ethyl acetate) yielded 78 mg (43%) of the title compound. MS 200 (M+H)$^+$.

Reference Example 23
3-(6-Bromo-3-pyridinyl)-2-propenal

2-Propylmagnesium chloride (2.0 M in THF, 5.00 mL 10.00 mmol) was added to a solution of 2,5-dibromopyridine (2.37 g, 10.00 mmol) in THF (5.0 mL) at RT. The resulting brown suspension was stirred for 1 h and then cooled to 0° C. 3-Dimethylaminoacrolein (95%, 1.30 mL, 12.36 mmol) was added and the mixture was warmed to RT and stirred for 2 h. 2 N HCl was added and after 5 min the mixture was cooled to 0° C. The precipitated solids were removed by filtration and partitioned between ethyl acetate (75 mL) and 10% NaOH (25 mL). The ethyl acetate layer was washed with brine (25 mL), dried (MgSO$_4$), and concentrated. Recrystallization from ethyl acetate provided 550 mg (26%) of the title compound as shiny brown flakes. MS 211 (M+H)$^+$.

Reference Example 24
3-[4-(3-pyridinyl)phenyl]-2-propenal 2M aq. Na$_2$CO$_3$ (1 mL) and a solution of 3-pyridinylboronic acid (148 mg, 1.20 mmol) in methanol (1 mL) were added to a solution of 4-bromocinnamaldehyde (211 mg, 1.00 mmol, prepared as described in Tetrahedron 1998, 54, 10761) and tetrakis(triphenylphosphine)palladium (0) (35 mg, 0.030 mmol) in toluene (2 mL) and the mixture was heated to reflux for 36 h. The cooled reaction mixture was diluted with dichloromethane, washed with sat. aq. NaHCO$_3$ and brine, dried (MgSO$_4$), and concentrated. Purification by chromatography (SiO$_2$, 1:1 hexane/ethyl acetate) yielded the title compound. MS 210 (M+H)$^+$.

Reference Example 25
3-[2-Fluoro-4-(1H-pyrazol-1-yl)phenyl]-2-propenal

A mixture of 2-fluoro-4-(1H-pyrazol-1-yl)benzaldehyde (1.06 g, 5.57 mmol, prepared as described in Reference Example 8), (1,3-dioxolan-2-ylmethyl)triphenylphosphonium bromide (3.60 g, 8.39 mmol), and TDA-1 (1.80 mL, 5.63 mmol) in dichloromethane (30 mL) and sat. aq. K$_2$CO$_3$ (30 mL) was heated to reflux for 20 h. The layers were separated and the aqueous layer was extracted with dichloromethane (2×15 mL). The combined organic layers were washed with water (30 mL) and brine (30 mL), dried (Na$_2$SO$_4$), and concentrated. THF (15 mL) and 10% HCl (15 mL) were added and the mixture was stirred for 1 h at rt. The mixture was cooled to 0° C., the precipitated solids were removed by filtration, washed with water and dried in vacuo. Recrystallization from IPA provided 0.84 g (70%) of the title compound as tan needles. MS 217 (M+H)$^+$.

Reference Example 26
3-[3-Methoxy-4-(1H-pyrazol-1-yl)phenyl]-2-propenal

A mixture of 3-methoxy-4-(1H-pyrazol-1-yl)benzaldehyde (1.52 g, 7.52 mmol, prepared as described in Reference Example 5), (1,3-dioxolan-2-ylmethyl)triphenylphosphonium bromide (4.85 g, 11.30 mmol), and TDA-1 (2.40 mL, 7.50 mmol) in dichloromethane (35 mL) and sat. aq. K$_2$CO$_3$ (35 mL) was heated to reflux for 18 h. The layers were separated and the aqueous layer was extracted with dichloromethane (2×20 mL). The combined organic layers were washed with water (50 mL) and brine (50 mL), dried (MgSO$_4$), and concentrated. THF (20 mL) and 10% HCl (20 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried (MgSO$_4$), and concentrated. Purification by chromatography (SiO$_2$, 2:1 hexane/ethyl acetate) provided 1.47 g (86%) of the title compound as a yellow solid. MS 229 (M+H)$^+$.

Reference Example 27
3-(6-Quinoxalinyl)-2-propenal

A mixture of 6-quinoxalinecarboxaldehyde (0.62 g, 3.92 mmol, prepared as described in *Photochem. Photobiol.* 1991, 54, 7), (1,3-dioxolan-2-ylmethyl)triphenylphosphonium bromide (2.50 g, 5.82 mmol), and TDA-1 (1.20 mL, 3.75 mmol) in dichloromethane (20 mL) and sat. aq. K$_2$CO$_3$ (20 mL) was heated to reflux for 4 h. The layers were separated and the aqueous layer was extracted with dichloromethane (2×20 mL). The combined organic layers were washed with water (50 mL) and brine (50 mL), dried (Na$_2$SO$_4$), and concentrated. THF (10 mL) and 10% HCl (10 mL) were added and the mixture was stirred for 1 h at rt. The mixture was cooled to 0° C., the precipitated solids were removed by filtration, washed with water and dried in vacuo to give 0.47 g (65%) of the title compound as a tan solid. MS 185 (M+H)$^+$.

Reference Example 28
3-(6-Quinolinyl)-2-propenal

A mixture of 6-quinolinecarboxaldehyde (1.58 g, 10.05 mmol, prepared as described in U.S. Pat. No. 5,559,256), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. K$_2$CO$_3$ (50 mL) was heated to reflux for 5 h. The layers were separated and the aqueous layer was extracted with dichloromethane (2×25 mL). The combined organic layers were washed with water (50 mL) and brine (50 mL), dried (MgSO$_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried (MgSO$_4$), and concentrated. Chromatography (SiO$_2$, 1:1 hexane/ethyl acetate+0.2% triethylamine) provided a yellow solid that was partioned between ethyl acetate (20 mL) and 10% HCl (15 mL). The aqueous layer was washed with ethyl acetate (2×20 mL) and then made basic with 10% NaOH. The precipitated solids were collected by filtration, washed with water, and dried in vacuo to give 1.20 g (65%) of the title compound as a light yellow solid. MS 184 (M+H)$^+$.

Reference Example 29
3-[4-(2-pyrimidinyl)phenyl]-2-propenal

A mixture of 4-(2-pyrimidinyl)-benzaldehyde (1.83 g, 9.94 mmol, prepared as described in WO 9828264), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. K$_2$CO$_3$ (50 mL) was heated to reflux for 20 h. The layers were separated and the aqueous layer was extracted with dichloromethane (2×25 mL). The combined organic layers were washed with water (50 mL) and brine (50 mL), dried (MgSO$_4$), and concentrated. THF (25 mL) and 10% HCl (25 mL) were added and the mixture was stirred for 1 h at rt. The mixture was cooled to 0° C., the precipitated solids were removed by filtration, washed with water and air-dried. Recrystallization from 2-propanol provided 1.20 g (57%) of the title compound as a light yellow solid. MS 211 (M+H)$^+$.

Reference Example 30
3-[4-(1H-pyrazol-1-yl)phenyl]-2-propenal

A mixture of 4-(1H-pyrazol-1-yl)-benzaldehyde (prepared as described in *J. Med Chem.* 1998, 41, 2390) (1.65 g, 9.58 mmol), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. K$_2$CO$_3$ (50 mL) was heated to reflux for 20 h. The layers were separated and the aqueous layer was extracted with dichloromethane (2×25 mL). The combined organic layers were washed with water (50 mL) and brine (50 mL), dried (MgSO$_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried (MgSO$_4$), and concentrated. Purification by chromatography (SiO$_2$, 3:1 hexane/ethyl acetate) provided 1.69 g (89%) of the title compound as a yellow solid. MS 199 (M+H)$^+$.

Reference Example 31
3-[6-(1H-1,2,4-triazol-1-yl)-2-pyridinyl]-2-propenal and 5-[6-(1H-1,2,4-triazol-1-yl)-2-pyridinyl]-2,4-pentadienal Step A:

A solution of 1,2,4-triazole (1.55 g, 22.35 mmol) in DMF (7 mL) was added to sodium hydride (60% in oil, 0.90 g, 22.50 mmol) in DMF (7 mL) and the resulting mixture was stirred 2 h at RT. 2-(1,3-Dioxolan-2-yl)-6-fluoropyridine (1.26 g, 7.45 mmol, prepared as described in *J. Med. Chem.* 1998, 41, 5070) was added dropwise and the resulting mixture heated to 80° C. for 3 h. The reaction mixture was poured into ice-water and extracted with ethyl acetate. The combined organic layers were washed with water and brine, dried (MgSO$_4$), and concentrated. The residue obtained was dissolved in a mixture of formic acid (12 mL) and water (3 mL), CuSO$_4$5H$_2$O (0.19 g, 0.76 mmol) was added, and the mixture was heated to 65° C. for 5 h. The reaction mixture was concentrated, diluted with 10% aq. NaOH to pH>10, and extracted with ethyl acetate. The combined organic extracts were washed with dilute aq. ammonium hydroxide and brine, dried (MgSO$_4$), and concentrated. The material was used in the next step without further purification.

Step B:

A mixture of the product from step A (0.80 g, 4.59 mmol), (1,3-dioxolan-2-ylmethyl)triphenylphosphonium bromide (3.00 g, 6.99 mmol), and TDA-1 (2.00 mL, 6.25 mmol) in dichloromethane (20 mL) and sat. aq. K$_2$CO$_3$ (20 mL) was heated to reflux for 20 h. The layers were separated and the aqueous layer was extracted with dichloromethane (2×20 mL). The combined organic layers were washed with water (50 mL) and brine (50 mL), dried (Na$_2$SO$_4$), and concentrated. THF (10 mL) and 10% HCl (10 mL) were added and the mixture was stirred for 1 h at rt. The reaction mixture was cooled to 0° C., made basic with 10% NaOH, and extracted with ethyl acetate (3×15 mL). The combined organic layers were washed with water (20 mL) and brine (20 mL), dried (MgSO$_4$), and concentrated. Purification by chromatography (SiO$_2$, 2:1 hexane/ethyl acetate) provided 0.40 g (43%) of an inseparable mixture of 3-[6-(1H-1,2,4-triazol-1-yl)-2-pyridinyl]-2-propenal [MS 201 (M+H)$^+$] and 5-[6-(1H-1,2,4-triazol-1-yl)-2-pyridinyl]-2,4-pentadienal [MS 227 (M+H)$^+$].

Reference Example 32
3-[4-(2-pyridinyl)phenyl]-2-propenal

The title compound was prepared by a procedure analogous to Reference Example 30 by substituting 4-(2-pyridinyl)-benzaldehyde for the 4-(1H-pyrazol-1-yl)-benzaldehyde of Reference Example 30. MS 210 (M+H)$^+$.

Reference Example 33
3-[4-(4-pyridinyl)phenyl]-2-propenal

The title compound was prepared by a procedure analogous to Reference Example 30 by substituting 4-(4-pyridinyl)-benzaldehyde (prepared as described in WO 9828264) for the 4-(1H-pyrazol-1-yl)-benzaldehyde of Reference Example 30. MS 210 (M+H)$^+$.

Reference Example 34
3-[4-(5-pyrimidinyl)phenyl]-2-propenal

The title compound was prepared by a procedure analogous to Reference Example 30 by substituting 4-(5-pyrimidinyl)-benzaldehyde (prepared as described in WO 9828264) for the 4-(1H-pyrazol-1-yl)-benzaldehyde of Reference Example 30. MS 211 (M+H)$^+$.

Reference Example 35
3-[4-(1H-1.2.4-triazol-1-yl)phenyl]-2-propenal

The title compound was prepared by a procedure analogous to Reference Example 30 by substituting 4-(1H-1,2,4-triazol-1-yl)-benzaldehyde (prepared as described in *J. Med Chem.* 1998, 41, 2390) for the 4-(1H-pyrazol-1-yl)-benzaldehyde of Reference Example 30. MS 200 (M+H)$^+$.

Reference Example 36
3-[4-(1H-1,2,3-triazol-1-yl)phenyl]-2-propenal

The title compound was prepared by a procedure analogous to Reference Example 30 by substituting 4-(1H-1,2,3-triazol-1-yl)-benzaldehyde (prepared as described in *J. Med Chem.* 1998, 41, 2390) for the 4-(1H-pyrazol-1-yl)-benzaldehyde of Reference Example 30. MS 200 (M+H)$^+$.

Reference Example 37
3-[4-(1H-imidazol-1-yl)phenyl]-2-propenal

The title compound was prepared by a procedure analogous to Reference Example 30 by substituting 4-(1H-imidazol-1-yl)-benzaldehyde (prepared as described in *J. Med Chem.* 1998, 41, 2390) for the 4-(1H-pyrazol-1-yl)-benzaldehyde of Reference Example 30. MS 199 (M+H)$^+$.

Reference Example 38
3-(4-quinolinyl)-2-propenal

The title compound was prepared by a procedure analogous to Reference Example 30 by substituting 4-quinolinecarboxaldehyde for the 4-(1H-pyrazol-1-yl)-benzaldehyde of Reference Example 30. MS 184 (M+H)$^+$.

Reference Example 39
3-[3-(2-pyridinyl)phenyl]-2-propenal

The title compound was prepared by a procedure analogous to Reference Example 30 by substituting 3-(2-pyridinyl)benzaldehyde (prepared as described in Reference Example 11) for the 4-(1H-pyrazol-1-yl)-benzaldehyde of Reference Example 30. MS 210 (M+H)$^+$.

Reference Example 40
3-[3-(2-pyrimidinyl)phenyl]-2-propenal

The title compound was prepared by a procedure analogous to Reference Example 30 by substituting 3-(2-pyrimidinyl)benzaldehyde (prepared as described in Reference Example 12) for the 4-(1H-pyrazol-1-yl)-benzaldehyde of Reference Example 30. MS 211 (M+H)$^+$.

Reference Example 41
3-[4-(4-methyl-2-pyrimidinyl)phenyl]-2-propenal

The title compound was prepared by a procedure analogous to Reference Example 30 by substituting 4-(4-methyl-2-pyrimidinyl)benzaldehyde (prepared as described in Reference Example 14) for the 4-(1H-pyrazol-1-yl)-benzaldehyde of Reference Example 30. MS 225 (M+H)$^+$.

Reference Example 42
3-[3-(1H-pyrazol-1-yl)phenyl]-2-propenal

The title compound was prepared by a procedure analogous to Reference Example 30 by substituting 3-(1H-pyrazol-1-yl)-benzaldehyde (prepared as described in Reference Example 3) for the 4-(1H-pyrazol-1-yl)-benzaldehyde of Reference Example 30. MS 199 (M+H)$^+$.

Reference Example 43
3-[4-(1-methyl-1H-pyrazol-3-yl)phenyl]-2-propenal

The title compound was prepared by a procedure analogous to Reference Example 30 by substituting 4-(1-methyl-1H-pyrazol-3-yl)benzaldehyde (prepared as described in *J. Med. Chem.* 1998, 41, 2390) for the 4-(1H-pyrazol-1-yl)-benzaldehyde of Reference Example 30. MS 213 (M+H)$^+$.

Reference Example 44
3-[4-(1-methyl-1H-pyrazol-5-yl)phenyl]-2-propenal

The title compound was prepared by a procedure analogous to Reference Example 30 by substituting 4-(1-methyl-1H-pyrazol-5-yl)benzaldehyde (prepared as described in *J. Med. Chem.* 1998, 41, 2390) for the 4-(1H-pyrazol-1-yl)-benzaldehyde of Reference Example 30. MS 213 (M+H)$^+$.

Reference Example 45
3-[4-(5-nitro-2-pyridinyl)phenyl]-2-propenal

The title compound was prepared by a procedure analogous to Reference Example 30 by substituting 4-(5-nitro-2-pyridinyl)benzaldehyde (prepared as described in Reference Example 19) for the 4-(1H-pyrazol-1-yl)-benzaldehyde of Reference Example 30. MS 255 (M+H)$^+$.

Reference Example 46
3-(8-Quinolinyl)-2-propenal

The title compound was prepared by a procedure analogous to Reference Example 30 by substituting 8-quinolinecarboxaldehyde (prepared as described in *J. Am. Chem. Soc.* 1997, 119, 8891) for the 4-(1H-pyrazol-1-yl)-benzaldehyde of Reference Example 30. MS 184 (M+H)$^+$.

Reference Example 47
3-(7-Quinolinyl)-2-propenal

The title compound was prepared by a procedure analogous to Reference Example 30 by substituting 7-quinolinecarboxaldehyde (prepared as described in *J. Med. Chem.* 1993, 36, 3308) for the 4-(1H-pyrazol-1-yl)-benzaldehyde of Reference Example 30. MS 184 (M+H)$^+$.

Reference Example 48
3-[6-(1H-pyrazol-1-yl)-2-pyridinyl]-2-propenal

The title compound was prepared by a procedure analogous to Reference Example 30 by substituting 6-(1H-pyrazol-1-yl)-2-pyridinecarboxaldehyde (prepared as described in *J. Med. Chem.* 1998, 41, 5070) for the 4-(1H-pyrazol-1-yl)-benzaldehyde of Reference Example 30. MS 200 (M+H)$^+$.

Reference Example 49
3-(4-Isoquinolinyl)-2-propenal

The title compound was prepared by a procedure analogous to Reference Example 30 by substituting 4-isoquinolinecarboxaldehyde for the 4-(1H-pyrazol-1-yl)-benzaldehyde of Reference Example 30. MS 184 (M+H)$^+$.

Reference Example 50
3-[3-Fluoro-4-(1H-pyrazol-1-yl)phenyl]-2-propenal

The title compound was prepared by a procedure analogous to Reference Example 30 by substituting 3-fluoro-4-(1H-pyrazol-1-yl)benzaldehyde (prepared as described in Reference Example 6) for the 4-(1H-pyrazol-1-yl)-benzaldehyde of Reference Example 30. MS 217 (M+H)$^+$.

Reference Example 51
3-[3-Fluoro-4-(1H-1,2,4-triazol-1-yl)phenyl]-2-propenal The title compound was prepared by a procedure analogous to Reference Example 30 by substituting 3-fluoro-4-(1H-1,2,4-triazol-1-yl)benzaldehyde (prepared as described in Reference Example 7) for the 4-(1H-pyrazol-1-yl)-benzaldehyde of Reference Example 30. MS 218 (M+H)$^+$.

Reference Example 52
3-[5-(2-pyridinyl)-2-thienyl]-2-propenal

The title compound was prepared by a procedure analogous to Reference Example 30 by substituting 5-(2-pyridinyl)-2-thiophenecarboxaldehyde (prepared as described in *J. Chem Soc., Perkin Trans.* 2 1998, 437) for the 4-(1H-pyrazol-1-yl)-benzaldehyde of Reference Example 30. MS 216 (M+H)$^+$.

Reference Example 53
5-[4-(1H-pyrazol-1-yl)phenyl]-2,4-pentadienal

The title compound was prepared by a procedure analogous to Reference Example 30 by substituting 3-[4-(1H-pyrazol-1-yl)phenyl]-2-propenal (prepared as described in Reference Example 30) for the 4-(1H-pyrazol-1-yl)-benzaldehyde of Reference Example 30. MS 225 (M+H)$^+$.

Reference Example 54
3-(1-phenyl-1H-pyrazol-4-yl)-2-propenal

The title compound was prepared by a procedure analogous to Reference Example 30 by substituting 1-phenyl-1H-pyrazol-4-ylcarboxaldehyde (prepared as described in *Synth. Commun.* 1998, 28, 1299) for the 4-(1H-pyrazol-1-yl)-benzaldehyde of Reference Example 30. MS 199 (M+H)$^+$.

Reference Example 55
3-[4-(4-methyl-1H-pyrazol-1-yl)phenyl]-2-propenal

The title compound was prepared by a procedure analogous to Reference Example 30 by substituting 4-(4-methyl-1H-pyrazol-1-yl)-benzaldehyde (prepared as described in Reference Example 4) for the 4-(1H-pyrazol-1-yl)-benzaldehyde of Reference Example 30. MS 213 (M+H)$^+$.

Reference Example 56
3-[4-(4-methoxy-2-pyrimidinyl)phenyl]-2-propenal

The title compound was prepared by a procedure analogous to Reference Example 30 by substituting 4-(4-methoxy-2-pyrimidinyl)benzaldehyde (prepared as described in Reference Example 13) for the 4-(1H-pyrazol-1-yl)-benzaldehyde of Reference Example 30. MS 241 (M+H)$^+$.

Reference Example 57
3-(4-pyrazinylphenyl)-2-propenal

The title compound was prepared by a procedure analogous to Reference Example 30 by substituting 4-pyrazinylbenzaldehyde (prepared as described in Reference Example 17) for the 4-(1H-pyrazol-1-yl)-benzaldehyde of Reference Example 30. MS 211 (M+H)$^+$.

Reference Example 58
3-[4-(4-pyrimidinyl)phenyl]-2-propenal

The title compound was prepared by a procedure analogous to Reference Example 30 by substituting 4-(4-pyrimidinyl)benzaldehyde (prepared as described in Reference Example 18) for the 4-(1H-pyrazol-1-yl)-benzaldehyde of Reference Example 30. MS 211 (M+H)$^+$.

Reference Example 59
3-[4-(2-pyrimidinyloxy)phenyl]-2-propenal

The title compound was prepared by a procedure analogous to Reference Example 30 by substituting 4-(2-pyrimidinyloxy)benzaldehyde (prepared as described in Reference Example 9) for the 4-(1H-pyrazol-1-yl)-benzaldehyde of Reference Example 30. MS 227 (M+H)$^+$.

Reference Example 60
3-[2-fluoro-4-(2-pyrimidinyl)phenyl]-2-propenal

The title compound was prepared by a procedure analogous to Reference Example 30 by substituting 2-fluoro-4-(2-pyrimidinyl)benzaldehyde (prepared as described in Reference Example 15) for the 4-(1H-pyrazol-1-yl)-benzaldehyde of Reference Example 30. MS 229 (M+H)$^+$.

Reference Example 61
3-[4-(3-pyridazinyl)phenyl]-2-propenal

The title compound was prepared by a procedure analogous to Reference Example 30 by substituting 4-(3-pyridazinyl)benzaldehyde (prepared as described in Reference Example 16) for the 4-(1H-pyrazol-1-yl)-benzaldehyde of Reference Example 30. MS 211 (M+H)$^+$.

Reference Example 62
3-[1-(2-pyrimidinyl)-1H-imidazol-4-yl]-2-propenal

The title compound was prepared by a procedure analogous to Reference Example 30 by substituting 1-(2-pyrimidinyl)-1H-imidazole-4-carboxaldehyde (prepared as described in Reference Example 10) for the 4-(1H-pyrazol-1-yl)-benzaldehyde of Reference Example 30. MS 201 (M+H)$^+$.

Reference Example 63
[[4-(2-pyrimidinyl)phenyl]methoxy]acetaldehyde

Step A: 4-(2-pyrimidinyl)benzenemethanol

The title compound was prepared by a procedure analogous to Reference Example 12 by substituting 4-(hydroxymethyl)phenylboronic acid for the 3-formylphenylboronic acid of Reference Example 12. MS 187 (M+H)$^+$.

Step B: [[4-(2-pyrimidinyl)phenyl]methoxy]acetaldehyde

A solution of the product from step A (559 mg, 3.00 mmol) in DMF (4 mL) was added dropwise to a suspension of sodium hydride (60% in mineral oil, 144 mg, 3.60 mmol) at 0° C. The solution was stirred for 30 min at 0° C., bromoacetaldehyde diethyl acetal (0.55 mL, 3.66 mmol) and tetrabutylammonium iodide (111 mg, 0.30 mmol) were added, and the resulting mixture was stirred at 70° C. for 12 h. Additional sodium hydride (60% in mineral oil, 70 mg, 1.75 mmol) and bromoacetaldehyde diethyl acetal (0.55 mL, 3.66 mmol) were added and heating at 70° C. was continued for 12 h. The reaction mixture was concentrated, the residue was diluted with water and extracted with ethyl acetate, the combined organic layers were dried (MgSO$_4$), and concentrated. Purification by chromatography (SiO$_2$, 1:1 hexane/ethyl acetate) gave material which was taken up in ethanol (2 mL) and 10% aq. HCl (10 mL) and stirred for 12 h. The reaction mixture was made basic with aq. NaOH, extracted with ethyl acetate, dried (MgSO$_4$), and concentrated. Purification by chromatography (SiO$_2$, 1:1 hexane/ethyl acetate) provided 80 mg (12%) of the title compound. MS 229 (M+H)$^+$.

Reference Example 64
1,3-dihydro-1,3-dioxo-2H-isoindole-2-acetaldehyde

To a solution of N-(2-hydroxyethyl)phthalimide (1.92 g, 10 mmol) and triethylamine (7 mL, 50 mmol) in DMSO (25 mL) was added solid pyridine sulfur trioxide (4.8 g, 30 mmol) by portions. The resulting mixture was stirred at room temperature for 1 h. The reaction mixture is poured into a mixture of $CH_2Cl_2$ and 0.5N aq. citric acid. The layers were separated and the organic layer was washed with water and brine. The organic phase was dried ($Na_2SO_4$), and the solvent was removed in vacuo. The resultant residue was purified by flash chromatography ($SiO_2$, 1:1 ethyl acetate/hexane) to provide the title compound (0.6 g, 32%). MS 190 $(M+H)^+$.

Reference Example 65
3-quinolinecarbonyl Chloride

To a suspension of 3-quinolinecarboxylic acid (580 mg, 3.35 mmol) in dichloromethane (25 mL) was added oxalyl chloride (2M in $CH_2Cl_2$, 3.4 mL, 6.7 mmol) dropwise at room temperature. DMF (1 drop) was added, resulting in immediate gas formation. The reaction mixture was stirred at room temperature for 2 h. Dichloromethane was evaporated. Additional dichloromethane (20 mL) was added to the residue. Concentration of the organic solvent gave the crude product. (640 mg, 99%).

Reference Example 66
2-butoxy-3,4-dihydro-4-phenyl-2H-pyran

A neat mixture of cinnamaldehyde (0.66 g, 4.99 mmol), butyl vinyl ether (1.30 mL, 10.05 mmol), and $Yb(fod)_3$ (265 mg, 0.25 mmol) was stirred at rt for 72 h and then heated to 50° C. for 18 h. Purification by chromatography ($SiO_2$, 95:5 hexane/ethyl acetate) yielded 0.89 g (77%) of the title compound. MS 233 $(M+H)^+$.

Reference Example 67
Compound 1t' of Scheme 16 ($R_d$ is CN, $R_e$ is H)

A solution of the compound from Example 1, step G (5.00 g, 7.79 mmol), 2-formyl-4,4-dimethoxybutanenitrile, (5.40 g, 34.36 mmol, prepared as described in Reference Example 68), and trifluoroacetic acid (6.0 mL, 77.88 mmol) in $CH_3CN$ (40 mL) was heated to 60° C. for 24 h. The reaction mixture was diluted with ethyl acetate (250 mL), washed with sat. aq. $NaHCO_3$ (250 mL), water (250 mL), and brine (250 mL), dried ($Na_2SO_4$), and concentrated. Purification by chromatography ($SiO_2$, 95:5:0.5 dichloromethane/methanol/conc. $NH_4OH$) yielded 3.00 g (54%) of the title compound. MS 717 $(M+H)^+$.

Reference Example 68
2-formyl-4,4-dimethoxybutanenitrile

Lithium diisopropylamide mono(tetrahydrofuran) (1.5 M in cyclohexane, 22.0 mL, 33.00 mmol) was added to THF (100 mL) at −30° C. and the resulting solution was stirred for 10 min before 3-cyanopropionaldehyde dimethyl acetal (3.90 mL, 29.90 mmol) was added dropwise over 5 min. After 15 min, methyl formate (2.80 mmol, 45.42 mmol) was added and the resulting solution was stirred at −20° C. to −15° C. for 2 h. The reaction mixture was quenched with water (100 mL) and washed with ether (2×50 mL, discarded). The aqueous layer was acidified with 10% HCl and extracted with ether (3×50 mL). The combined ether extracts were washed with brine (3×50 mL), dried ($MgSO_4$), and concentrated. The residue was dissolved in dichloromethane and concentrated to remove traces of THF and provide 2.28 g (49%) of the title compound as a pale yellow oil.

Reference Example 69
3-(3-quinolinyl)-2-propenal

The title compound was prepared by a procedure analogous to Reference Example 30 by substituting 3-quinolinecarboxaldehyde for the 4-(1H-pyrazol-1-yl)-benzaldehyde of Reference Example 30. MS 184 $(M+H)^+$.

Reference Example 70
3-(3-pyridinyl)-2-propenal

The title compound was prepared by a procedure analogous to Reference Example 23 by substituting 3-bromopyridine for the 2,5-dibromopyridine of Reference Example 23. MS 134 $(M+H)^+$.

Reference Example 71
3-[4-(2-pyrimidinyl)phenyl]cyclobutanemethanamine

Step A. 3-[4-(2-pyrimidinyl)phenyl]cyclobutanone

A mixture of $Na_2CO_3$ (1.58 g, 14.9 mmol) and 3-(4-boronophenyl)-cyclobutanone ethylene ketal (1.6 g, 6.8 mmol, prepared as described in *J. Org. Chem.* 1999, 64, 8495) in water (10 mL) were added to a solution of 2-bromopyrimidine (1.1 g, 6.8 mmol) and tetrakis (triphenylphosphine)palladium(0) (0.24 g, 0.21 mmol) in DME (15 mL) and the mixture was heated to reflux for 24 h. The cooled reaction mixture was diluted with ethyl acetate, washed with sat. $NaHCO_3$ and brine, dried ($MgSO_4$) and concentrated.

The above crude product was dissolved in methanol (30 ML) along with concentrated HCl (2 mL). The reaction mixture was stirred at room temperature for 24 h. The solvent was removed under reduced pressure and the residue was dissolved in ethyl acetate and washed with 10% NaOH and brine, dried ($MgSO_4$) and concentrated. Purification by chromatography ($SiO_2$, 1:1 hexane/ethyl acetate) yielded 1.1 g (72%) of the title compound. MS 225 $(M+H)^+$.

Step B. 3-[4-(2-pyrimidinyl)phenyl]cyclobutanol

To a solution of the compound from Step A (370 mg, 1.65 mmol) in THF (10 mL) was added $LiAlH_4$ (1 M in THF, 3.3 mL, 3.3 mmol) dropwise. The reaction mixture was stirred at room temperature for 30 min. and Sat. $NH_4Cl$ was added. The mixture was extracted with ethyl acetate, washed with brine, dried ($MgSO_4$) and concentrated. This material was directly used in the next step without further purification. MS 227 $(M+H)^+$.

Step C. 3-[4-(2-pyrimidinyl)phenyl]cyclobutanol, methanesulfonate (ester)

To an ice-cooled solution of the compound from Step B (360 mg, 1.6 mmol) in methylene chloride (40 mL), triethylamine (0.34 mL, 2.4 mmol) and methanesulfonyl chloride (0.19 mL, 2.4 mmol) were added dropwise. The reaction mixture was stirred at 0° C. for 1 h. The mixture was diluted with dichloromethane (40 mL), washed with water and brine, dried and concentrated. Purification by chromatography ($SiO_2$, 2:1 hexane/ethyl acetate) yielded 330 mg (68%) of the title compound. MS 305 $(M+H)^+$.

Step D. 3-[4-(2-pyrimidinyl)phenyl]cyclobutanecarbonitrile

To a solution of the compound from Step C (150 mg, 0.49 mmol) in DMSO (1 mL) was added potassium cyanide (160 mg, 2.45 mmol) and 18-crown-6 (130 mg, 0.49 mmol). The reaction mixture was heated for 72 h. at 80° C. The cooled reaction mixture was diluted with ethyl acetate, washed with water and brine, dried ($MgSO_4$) and concentrated. This material was directly used in the next step without further purification. MS 236 $(M+H)^+$.

Step E. 3-[4-(2-pyrimidinyl)phenyl]cyclobutanemethanamine

To a solution of the compound from Step D (80 mg, 0.34 mmol) in methanol (5 mL) was added nickel chloride hexahydrate (82 mg, 0.35 mmol) followed by sodium borohydride (84 mg, 2.2 mmol). The reaction mixture was stirred at room temperature for 15 min. The precipitate was filtered off and methanol was evaporated. The residue was dissolved in ethyl acetate, washed with water and brine, dried (MgSO$_4$) and concentrated. Purification by chromatography (SiO$_2$, 93:7:0.5 dichloromethane/methanol/conc. NH$_4$OH) yielded 10 mg (12%) of the title compound. MS 240 (M+H)$^+$.

Reference Example 72
3-[4-(2-pyrimidinyl)phenyl]cyclobutanamine

To a solution of the compound from Reference Example 71, Step C (80 mg, 0.26 mmol) in DMSO (1 mL) was added sodium azide (34 mg, 0.52 mmol). The reaction mixture was heated overnight at 60° C. The cooled reaction mixture was diluted with ethyl acetate, washed with water and brine, dried (MgSO$_4$) and concentrated. This material was directly used in the next step without further purification.

To a solution of the above compound in THF (2 mL) was added lithium aluminium hydride (1 M in THF, 0.52 mL, 0.52 mmol) dropwise. The reaction mixture was stirred at room temperature for 15 min. and Sat. NH$_4$Cl was added. The mixture was extracted with ethyl acetate, washed with brine, dried (MgSO$_4$) and concentrated. Purification by chromatography (SiO$_2$, 95:5:0.5 dichloromethane/methanol/conc. NH$_4$OH) yielded 16 mg (27%) of the title compound. MS 226 (M+H)$^+$.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula 1

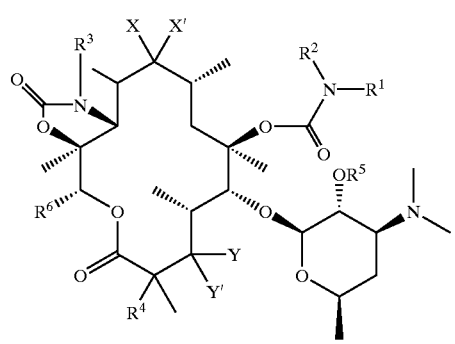

Formula 1 wherein
R$^1$ and R$^2$ are independently selected from hydrogen, optionally substituted —CR$_f$R$_g$(C$_1$–C$_8$)alkyl, optionally substituted —CR$_f$R$_g$(C$_2$–C$_8$)alkenyl, optionally substituted —CR$_f$R$_g$(C$_2$–C$_8$)alkynyl, optionally substituted cycloalkyl, and optionally substituted (C$_5$–C$_7$)-cycloalkenyl, provided that R$^1$ and R$^2$ are not both hydrogen, wherein the substituents are selected from halogen, alkyl, alkenyl, alkynyl, cycloalkyl, oxo, aryl, heteroaryl, heterocyclo, CN, nitro, —COOR$_a$, —OCOR$_a$, —OR$_a$, —SR$_a$, —SOR$_a$, —SO$_2$R$_a$, —NR$_a$R$_b$, —CON$_a$R$_b$, —OCONR$_a$R$_b$, —NHCOR$_a$, —NHCOOR$_a$, and —NHCONR$_a$R$_b$, wherein R$_a$ and R$_b$ are independently selected from hydrogen, alkyl, alkenyl, alkynyl, cycloalkyl, aryl, heteroaryl, heterocyclo, aralkyl, heteroaralkyl, and heterocycloalkyl; and
R$_f$ and R$_g$ are independently selected from the group consisting of hydrogen, alkyl, alkenyl, alkynyl, cycloalkyl, aryl, heteroaryl, heterocyclo, COOR$_a$, and CONR$_a$R$_b$;
or R$^1$ and R$^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —COOR$_a$, —OCOR$_a$, —OR$_a$, —SR$_a$, —SOR$_a$, —SO$_2$R$_a$, —NR$_a$R$_b$, —CON$_a$R$_b$, —OCONR$_a$R$_b$, —NHCOR$_a$, —NHCOOR$_a$, and —NHCONR$_a$R$_b$;
R$^3$ is hydrogen or —W—V, wherein
W is selected from the group consisting of (a) —NH—(CH$_2$)$_p$—, (b) —(CH$_2$)$_q$—, (c) —O—(CH$_2$)$_r$—, (d) —NH—C$_1$–C$_6$alkenyl-, (e) —C$_1$–C$_6$alkenyl-, (f) —O—C$_1$–C$_6$alkenyl-, (g) —NH—C$_1$–C$_6$alkynyl-, (h) —C$_1$–C$_6$alkynyl-, and (i) —O—C$_1$–C$_6$alkynyl-;
p is 0 to 5;
q is 0 to 5; and
r is 0 to 5; and
V is selected from the group consisting of (a) hydrogen, (b) aryl, (c) substituted aryl, (d) heteroaryl, (e) substituted heteroaryl, and (f) Ar$_1$–Ar$_2$, wherein Ar$_1$ and Ar$_2$ are independently selected from the group consisting of (i) aryl, (ii) substituted aryl, (iii) heteroaryl, and (iv) substituted heteroaryl;
R$^4$ is selected from hydrogen, halogen, and hydroxy;
R$^5$ is hydrogen or a hydroxy protecting group;
R$^6$ is selected from hydrogen, alkyl, C$_2$–C$_{10}$-alkenyl, C$_2$–C$_{10}$-alkynyl, aryl, heteroaryl, heterocyclo, aryl (C$_1$–C$_{10}$)alkyl, aryl(C$_2$–C$_{10}$)alkenyl, aryl(C$_2$–C$_{10}$)alkynyl, heterocyclo(C$_1$–C$_{10}$)alkyl, heterocyclo(C$_2$–C$_{10}$)alkenyl, and heterocyclo(C$_2$–C$_{10}$)alkynyl, C$_3$–C$_6$-cycloalkyl, C$_5$–C$_8$-cycloalkenyl, alkoxyalkyl containing 1–6 carbon atoms in each alkyl or alkoxy group, and alkylthioalkyl containing 1–6 carbon atoms in each alkyl or thioalkyl group;
X and X', together with the carbon atom to which they are attached, form C=O, C=NR$_c$, or C=NOR$_c$, wherein R$_c$ is independently selected from hydrogen, alkyl, alkenyl and alkynyl; and
Y and Y', together with the carbon atom to which they are attached, form C=O, —CHOH, C=NR$_c$, or C=NOR$_c$, wherein R$_c$ is independently selected from hydrogen, alkyl, alkenyl and alkynyl;
or an optical isomer, enantiomer, diastereomer, racemate or racemic mixture thereof, or a pharmaceutically acceptable salt, esters or pro-drugs thereof.

2. The compound of claim 1 wherein:
R$^1$ and R$^2$ are independently selected from hydrogen, optionally substituted C$_1$–C$_8$-alkyl, optionally substituted —CH$_2$C$_2$–C$_8$-alkenyl, optionally substituted —CH$_2$C$_2$–C$_8$-alkynyl, wherein the substituents are selected from halogen, alkyl, alkenyl, alkynyl, cycloalkyl, oxo, aryl, heteroaryl, heterocyclo, CN, nitro, —COOR$_a$, —OCOR$_a$, —OR$_a$, —SR$_a$, —SOR$_a$, —SO$_2$R$_a$, —NR$_a$R$_b$, —CON$_a$R$_b$, —OCONR$_a$R$_b$, —NHCOR$_a$, —NHCOOR$_a$, and —NHCONR$_a$R$_b$, wherein R$_a$ and R$_b$ are independently selected from hydrogen, alkyl, alkenyl, alkynyl, cycloalkyl, aryl, heteroaryl, heterocyclo, aralkyl, heteroaralkyl, and heterocycloalkyl, provided that R$^1$ and R$^2$ are not both hydrogen; and
R$^3$ is hydrogen.

3. The compound of claim 1 wherein R$^3$ is hydrogen.

4. The compound of claim 2 wherein:

$R^1$ and $R^2$ are independently selected from hydrogen, substituted $C_1$–$C_8$-alkyl, substituted —$CH_2C_2$–$C_8$-alkenyl, and substituted —$CH_2C_2$–$C_8$-alkynyl, wherein the substituents are selected from CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl; provided that $R^1$ and $R^2$ are not both hydrogen;

$R^3$ is hydrogen;

$R^4$ is selected from hydrogen, halogen, and hydroxy;

$R^5$ is hydrogen or a hydroxy protecting group;

$R^6$ is selected from hydrogen, alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$)alkenyl, aryl($C_2$–$C_{10}$)alkynyl, heterocyclo($C_1$–$C_{10}$)alkyl, heterocyclo($C_2$–$C_{10}$)alkenyl, and heterocyclo($C_2$–$C_{10}$)alkynyl, $C_3$–$C_6$-cycloalkyl, $C_1$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

X and X', together with the carbon atom to which they are attached, form C=O, C=$NR_c$, or C=$NOR_c$, wherein $R_c$ is independently selected from hydrogen, alkyl, alkenyl and alkynyl; and Y and Y', together with the carbon atom to which they are attached, form C=O, —CHOH, C=$NR_c$, or C=$NOR_c$, wherein $R_c$ is independently selected from hydrogen, alkyl, alkenyl and alkynyl.

5. The compound of claim 1 wherein $R^1$ and $R^2$ are selected from the group consisting of hydrogen, $C_1$–$C_8$-alkyl, —$CH_2C_2$–$C_8$-alkenyl, and —$CH_2C_2$–$C_8$-alkynyl, said $C_1$–$C_8$-alkyl, —$CH_2C_2$–$C_8$-alkenyl, and —$CH_2C_2$–$C_8$-alkynyl being substituted with one or more members selected from the group consisting of —$OR_a$ wherein $R_a$ is selected from H, alkyl, alkenyl, alkynyl, cycloalkyl, aryl, heteroaryl, heterocyclo, aralkyl, heteroaralkyl, and heterocycloalkyl, provided that $R^1$ and $R^2$ are not both hydrogen.

6. The compound of claim 1 wherein $R^4$ is hydrogen, X and X' form C=O together with the carbon atom to which they are attached, and Y and Y' form C=O together with the carbon atom to which they are attached.

7. The compound of claim 1 wherein $R^4$ is fluorine.

8. The compound of claim 7 wherein X and X' form C=O together with the carbon atom to which they are attached, and Y and Y' form C=O together with the carbon atom to which they are attached.

9. The compound of claim 7 wherein $R^1$ and $R^2$ are independently selected from hydrogen, substituted $C_1$–$C_8$-alkyl, substituted —$CH_2C_2$–$C_8$-alkenyl, and substituted —$CH_2C_2$–$C_8$-alkynyl, wherein the substituents are selected from CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl; provided that $R^1$ and $R^2$ are not both hydrogen;

$R^3$ is selected from hydrogen;

$R^5$ is hydrogen or a hydroxy protecting group;

$R^6$ is selected from hydrogen, alkyl, $C_2$–$C_{10}$-alkenyl, $C_2$–$C_{10}$-alkynyl, aryl, heteroaryl, heterocyclo, aryl ($C_1$–$C_{10}$)alkyl, aryl($C_2$–$C_{10}$)alkenyl, aryl($C_2$–$C_{10}$) alkynyl, heterocyclo($C_1$–$C_{10}$)alkyl, heterocyclo ($C_2$–$C_{10}$)alkenyl, and heterocyclo($C_2$–$C_{10}$)alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group.

10. The compound of claim 7 wherein $R^3$ is hydrogen.

11. The compound of claim 9 wherein X and X' form C=O together with the carbon atom to which they are attached, and Y and Y' form C=O together with the carbon atom to which they are attached.

12. The compound of claim 10 wherein X and X' form C=O together with the carbon atom to which they are attached, and Y and Y' form C=O together with the carbon atom to which they are attached.

13. The compound of claim 1 wherein $R^5$ is selected from acyl and aroyl.

14. The compound of claim 1 wherein $R^6$ is ethyl.

15. The compound of claim 2 wherein $R^6$ is ethyl.

16. The compound of claim 3 wherein $R^6$ is ethyl.

17. The compound of claim 4 wherein $R^6$ is ethyl.

18. The compound of claim 5 wherein $R^6$ is ethyl.

19. The compound of claim 6 wherein $R^6$ is ethyl.

20. The compound of claim 7 wherein $R^6$ is ethyl.

21. The compound of claim 8 wherein $R^6$ is ethyl.

22. The compound of claim 9 wherein $R^6$ is ethyl.

23. The compound of claim 10 wherein $R^6$ is ethyl.

24. The compound of claim 11 wherein $R^6$ is ethyl.

25. The compound of claim 12 wherein $R^6$ is ethyl.

26. The compound of claim 13 wherein $R^6$ is ethyl.

27. A compound selected from those of the formula 1' or 1":

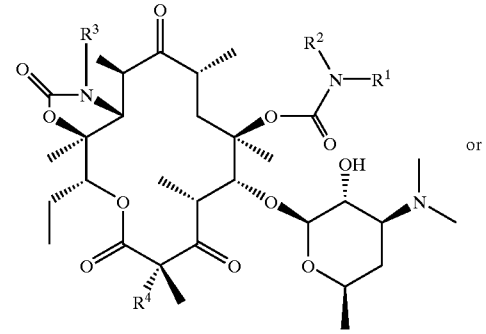

Formula 1' or

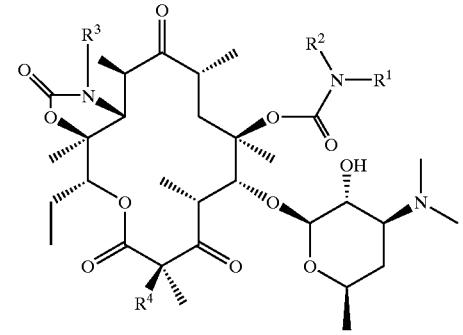

Formula 1"

wherein $R^1$ and $R^2$ are independently selected from hydrogen, optionally substituted —$CR_fR_g(C_1$–C8)alkyl, optionally substituted —$CR_fR_g(C_2$–$C_8$)alkenyl, optionally substituted —$CR_fR_g(C_2$–$C_8$)alkynyl, optionally substituted cycloalkyl, and optionally substituted ($C_5$–$C_7$)- cycloalkenyl, provided that $R^1$ and $R^2$ are not both hydrogen, wherein the substituents are selected from CN, nitro, —$COOR_a$, —$OCOR_a$, —$OR_a$, —$SR_a$, —$SOR_a$, —$SO_2R_a$, —$NR_aR_b$, —$CON_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;

$R_f$ and $R_g$ are independently selected from the group consisting of hydrogen, alkyl, alkenyl, alkynyl, cycloalkyl, aryl, heteroaryl, heterocyclo, $COOR_a$, and $CONR_aR_b$;

or $R^1$ and $R^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CON_aR_b$, —$OCONR_aR_b$, —$NHCOR_a$, —$NHCOOR_a$, and —$NHCONR_aR_b$;

$R^3$ is hydrogen or —W—V, wherein

W is selected from the group consisting of (a) —NH—$(CH_2)_p$—, (b) —$(CH_2)_q$—, (c) —O—$(CH_2)_r$—, (d) —NH—$C_1$-$C_6$alkenyl-, (e) —$C_1$-$C_6$alkenyl-, (f) —O—$C_1$-$C_6$alkenyl-, (g) —NH—$C_1$-$C_6$alkynyl-, (h) —$C_1$-$C_6$alkynyl-, and (i) —O—$C_1$-$C_6$alkynyl-;

p is 0 to 5;
q is 0 to 5; and
r is 0 to 5; and

V is selected from the group consisting of (a) hydrogen, (b) aryl, (c) substituted aryl, (d) heteroaryl, (e) substituted heteroaryl, and (f) $Ar_1$-$Ar_2$, wherein $Ar_1$ and $Ar_2$ are independently selected from the group consisting of (i) aryl, (ii) substituted aryl, (iii) heteroaryl, and (iv) substituted heteroaryl;

$R^4$ is selected from hydrogen, halogen, and hydroxy; or an optical isomer, enantiomer, diastereomer, racemate or racemic mixture thereof, or a pharmaceutically acceptable salt, ester or pro-drugs thereof.

28. A compound of claim 27 wherein:

$R^1$ and $R^2$ are independently selected from hydrogen, substituted $C_1$-$C_8$-alkyl, substituted —$CH_2C_2$-$C_8$-alkenyl, and substituted —$CH_2C_2$-$C_8$-alkynyl, wherein the substituents are selected from CN, nitro, —$COOR_a$, —$OCOR_a$, —$OR_a$, —$SR_a$, —$SOR_a$, —$SO_2R_a$, —$NR_aR_b$, —$CON_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl; provided that $R^1$ and $R^2$ are not both hydrogen;

$R^3$ is hydrogen or —W—V, wherein

W is selected from the group consisting of (a) —NH—$(CH_2)_p$—, (b) —$(CH_2)_q$—, (c) —O—$(CH_2)_r$—, (d) —NH—$C_1$-$C_6$alkenyl-, (e) —$C_1$-$C_6$alkenyl-, (f) —O—$C_1$-$C_6$alkenyl-, (g) —NH—$C_1$-$C_6$alkynyl-, (h) —$C_1$-$C_6$alkynyl-, and (i) —O—$C_1$-$C_6$alkynyl-;

p is 0 to 5;
q is 0 to 5; and
r is 0 to 5; and

V is selected from the group consisting of (a) hydrogen, (b) aryl, (c) substituted aryl, (d) heteroaryl, (e) substituted heteroaryl, and (e $Ar_1$-$Ar_2$, wherein $Ar_1$ and $Ar_2$ are independently selected from the group consisting of (i) aryl, (ii) substituted aryl, (iii) heteroaryl and (iv) substituted heteroaryl;

$R^4$ is selected from hydrogen, halogen, and hydroxy; or an optical isomer, enantiomer, diastereomer, racemate or racemic mixture thereof, or a pharmaceutically acceptable salt, ester or pro-drugs thereof.

29. A compound of claim 27 wherein $R^3$ is hydrogen.

30. The compound of claim 28 wherein $R^3$ is hydrogen.

31. The compound of claim 30 wherein $R^1$ and $R^2$ are selected from the group consisting of $C_1$-$C_8$-alkyl, —$CH_2C_2$-$C_8$-alkenyl, and —$CH_2C_2$-$C_8$-alkynyl, said $C_1$-$C_8$-alkyl, —$CH_2C_2$-$C_8$-alkenyl, and —$CH_2C_2$-$C_8$-alkynyl being optionally substituted with one or more members selected from the group consisting of —$OR_a$ wherein $R_a$ is selected from H, alkyl, alkenyl, alkynyl, cycloalkyl, aryl, heteroaryl, heterocyclo, aralkyl, heteroaralkyl, and heterocycloalkyl.

32. The compound of claim 31 wherein $R^4$ is fluoro.

33. The compound of claim 30 wherein $R^4$ is fluoro.

34. The compound of claim 29 wherein $R^4$ is fluoro.

35. A pharmaceutical composition comprising a compound of claim 1 and a pharmaceutically acceptable carrier.

36. A method of treating a subject having a condition caused by or contributed to by bacterial infection, which comprises administering to said subject a therapeutically effective amount of the compound of Formula I as defined in claim 1.

37. A method of preventing a subject from suffering from a condition caused by or contributed to by bacterial infection, which comprises administering to the subject a prophylactically effective amount of the compound of Formula 1 as defined in claim 1.

38. The method of claim 36 wherein said condition is selected from community-acquired pneumonia, upper and lower respiratory tract infections, skin and soft tissue infections, meningitis, hospital-acquired lung infections, and bone and joint infections.

39. The method of claim 36 wherein said bacterium is selected from *S. aureus, S. epidermidis, S. pneumoniae,* Enterococcus spp., *Moraxella catarrhalis* and *H. influenzae.*

40. The method of claim 36 wherein said bacterium is a Gram-positive coccus.

41. The method of claim 36 wherein said Gram-positive coccus is antibiotic-resistant.

42. The method of claim 41 wherein said Gram-positive coccus is erythromycin-resistant.

43. A process for preparation of a compound having the formula:

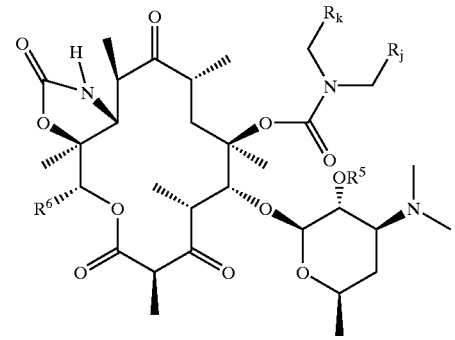

wherein $R_j$ and $R_k$ taken together with the atoms to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CON_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl;

$R^5$ is hydrogen or a hydroxy protecting group; and $R^6$ is selected from hydrogen, alkyl, $C_2$-$C_{10}$-alkenyl, $C_2$-$C_{10}$-alkynyl, aryl, heteroaryl, heterocyclo, aryl($C_1$-$C_{10}$)alkyl, aryl($C_2$-$C_{10}$)alkenyl, aryl($C_2$-$C_{10}$)alkynyl, heterocyclo($C_1$-$C_{10}$)alkyl, heterocyclo($C_2$-$C_{10}$)alkenyl, and heterocyclo($C_2$-$C_{10}$)alkynyl, $C_3$-$C_6$-cycloalkyl, $C_5$-$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

said method comprising:

a) treating a compound having the formula:

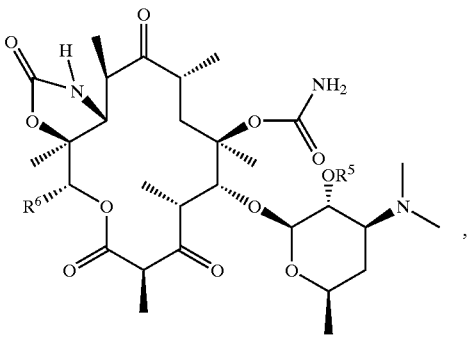

wherein $R^5$ and $R^6$ are as previously defined, with a suitably substituted dialdehyde or dialdehyde equivalent in the presence of a reducing agent and acid; and b) when $R^5$ is a hydroxy protecting group, optionally deprotecting the 2'-hydroxy group.

44. A process for preparation of a compound having the formula

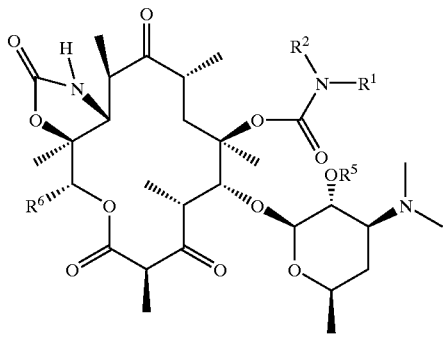

wherein $R^1$ is hydrogen and $R^2$ is selected from optionally substituted —$CR_fR_g$($C_1$-$C_8$)alkyl, optionally substituted —$CR_fR_g$($C_2$-$C_8$)alkenyl, optionally substituted —$CR_fR_g$($C_2$-$C_8$)alkynyl, optionally substituted cycloalkyl, and optionally substituted ($C_5$-$C_7$)-cycloalkenyl, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl; and $R_f$ and $R_g$ are independently selected from the group consisting of hydrogen, alkyl, alkenyl, alkynyl, cycloalkyl, aryl, heteroaryl, heterocyclo, $COOR_a$, and $CONR_aR_b$;

or $R^1$ and $R^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_3R_b$, —$CON_aR_b$, —$OCONR_aR_b$, —$NHCOR_a$, —$NHCOOR_a$, and —$NHCONR_aR_b$;

$R^5$ is hydrogen or a hydroxy protecting group;

$R^6$ is selected from hydrogen, alkyl, $C_2$-$C_{10}$-alkenyl, $C_2$-$C_{10}$-alkynyl, aryl, heteroaryl, heterocyclo, aryl($C_1$-$C_{10}$)alkyl, aryl($C_2$-$C_{10}$)alkenyl, aryl($C_2$-$C_{10}$)alkynyl, heterocyclo($C_1$-$C_{10}$)alkyl, heterocyclo($C_2$-$C_{10}$)alkenyl, and heterocyclo($C_2$-$C_{10}$)alkynyl, $C_3$-$C_6$-cycloalkyl, $C_5$-$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

said process comprising:

a) treating a compound having the formula:

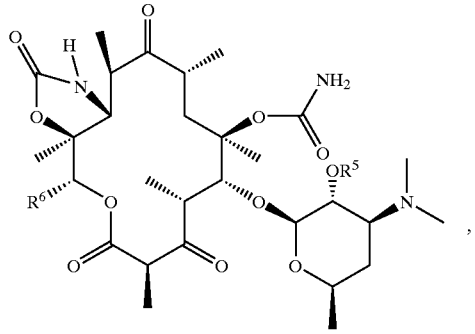

wherein $R^5$ and $R^6$ are as previously defined, with a suitably substituted 1,4-dialdehyde or 1,4-dialdehyde equivalent and an acid to give a compound having the formula:

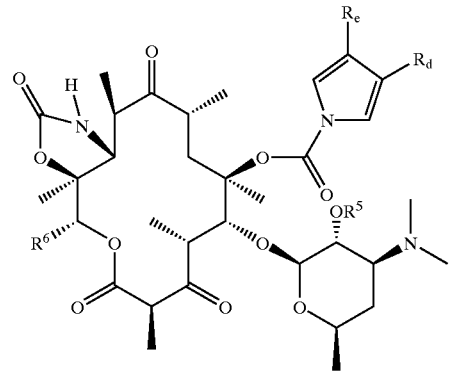

wherein $R^5$ and $R^6$ are as previously defined, and $R_d$ and $R_e$ are independently selected from the group consisting of hydrogen, CN, nitro, —C(O)$R_h$, —C(O)O$R_h$, —C(O)N$R_hR_i$, —SO$_2R_h$, optionally substituted $C_1$-$C_8$-alkyl, optionally substituted aryl, and optionally substituted heteroaryl, where $R_h$ and $R_i$ are independently selected from the group consisting of hydrogen, alkyl, aryl, and heteroaryl;

b) treating the compound obtained in step (a) with an amine of formula $R^1R^2NH$, wherein $R^1$ and $R^2$ are as previously defined; and c) when $R^5$ is a hydroxy protecting group, optionally deprotecting the 2'-hydroxy group.

45. A process for preparation of a compound having the formula:

[Chemical structure]

wherein $R^1$ is hydrogen and $R^2$ is selected from optionally substituted —$CR_fR_g(C_1-C_8)$alkyl, optionally substituted —$CR_fR_g(C_2-C_8)$alkenyl, optionally substituted —$CR_fR_g(C_2-C_8)$alkynyl, optionally substituted cycloalkyl, and optionally substituted $(C_5-C_7)$-cycloalkenyl, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from hydrogen, alkyl, alkenyl, alkynyl, cycloalkyl, aryl, heteroaryl, heterocyclo, aralkyl, heteroaralkyl, and heterocycloalkyl; and $R_f$ and $R_g$ are independently selected from the group consisting of hydrogen, alkyl, alkenyl, alkynyl, cycloalkyl, aryl, heteroaryl, heterocyclo, $COOR_a$, and $CONR_aR_b$;

or $R^1$ and $R^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CON_aR_b$, —$OCONR_aR_b$, —$NHCOR_a$, —$NHCOOR_a$, and —$NHCONR_aR_b$;

$R^5$ is hydrogen or a hydroxy protecting group;

$R^6$ is selected from hydrogen, alkyl, $C_2-C_{10}$-alkenyl, $C_2-C_{10}$-alkynyl, aryl, heteroaryl, heterocyclo, aryl$(C_1-C_{10})$alkyl, aryl$(C_2-C_{10})$alkenyl, aryl$(C_2-C_{10})$alkynyl, heterocyclo$(C_1-C_{10})$alkyl, heterocyclo$(C_2-C_{10})$alkenyl, and heterocyclo$(C_2-C_{10})$alkynyl, $C_3-C_6$-cycloalkyl, $C_5-C_8$-cycloalkenyl, alkoxyalkyl containing 1–6 carbon atoms in each alkyl or alkoxy group, and alkylthioalkyl containing 1–6 carbon atoms in each alkyl or thioalkyl group;

said process comprising:

a) treating a compound having the formula:

[Chemical structure]

wherein $R^5$ and $R^6$ are as previously defined, and $R_d$ and $R_e$ are independently selected from the group consisting of hydrogen, CN, nitro, —$C(O)R_h$, —$C(O)OR_h$, —$C(O)NR_hR_i$, —$SO_2R_h$, optionally substituted $C_1-C_8$-alkyl, optionally substituted aryl, and optionally substituted heteroaryl, where $R_h$ and $R_i$ are independently selected from the group consisting of hydrogen, alkyl, aryl, and heteroaryl, with an amine of formula $R^1R^2NH$, wherein $R^1$ and $R^2$ are as previously defined; and b) when $R^5$ is a hydroxy protecting group, optionally deprotecting the 2'-hydroxy group.

46. The compound of claim 27 wherein $R^2$ is hydrogen.
47. The compound of claim 28 wherein $R^2$ is hydrogen.
48. The compound of claim 29 wherein $R^2$ is hydrogen.
49. The compound of claim 30 wherein $R^2$ is hydrogen.
50. The compound of claim 48 wherein $R^4$ is fluoro.
51. The compound of claim 49 wherein $R^4$ is fluoro.
52. The compound of claim 31 wherein $R^2$ is hydrogen.
53. The compound of claim 32 wherein $R^2$ is hydrogen.
54. The compound of claim 1 wherein $R^1$ is selected from optionally substituted cycloalkyl and optionally substituted $(C_5-C_7)$-cycloalkenyl and $R^2$ is hydrogen, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$, —$CONR_aR_b$, —$OCONR_aR_b$, —$NHCOR_a$, —$NHCOOR_a$, and —$NHCONR_aR_b$;

or $R^1$ and $R^2$, together with the nitrogen atom to which they are attached, form an optionally substituted nitrogen-containing heterocycle, wherein the substituents are selected from halogen, alkyl, alkenyl, alkynyl, cycloalkyl, oxo, aryl, heteroaryl, heterocyclo, CN, nitro, —$COOR_a$, —$OCOR_a$, —$OR_a$, —$SR_a$, —$SOR_a$, —$SO_2R_a$, —$NR_aR_b$,—$CON_aR_b$,—$OCONR_aR_b$, —$NHCOR_a$, —$NHCOOR_a$, and —$NHCONR_aR_b$.

* * * * *